US012653634B2

(12) United States Patent (10) Patent No.: US 12,653,634 B2
Rohr Daniel et al. (45) Date of Patent: Jun. 16, 2026

(54) SYSTEMS AND METHODS FOR POSITIONING MEDICAL INSTRUMENTS

(71) Applicant: INTUITIVE SURGICAL OPERATIONS, INC., Sunnyvale, CA (US)

(72) Inventors: Matthew D. Rohr Daniel, San Francisco, CA (US); David W. Bailey, Portola Valley, CA (US)

(73) Assignee: INTUITIVE SURGICAL OPERATIONS, INC., Sunnyvale, CA (US)

( * ) Notice: Subject to any disclaimer, the term of this patent is extended or adjusted under 35 U.S.C. 154(b) by 139 days.

(21) Appl. No.: 18/600,440

(22) Filed: Mar. 8, 2024

(65) Prior Publication Data

US 2024/0207005 A1 Jun. 27, 2024

Related U.S. Application Data

(63) Continuation of application No. 17/279,208, filed as application No. PCT/US2019/054718 on Oct. 4, 2019, now Pat. No. 11,969,227.

(Continued)

(51) Int. Cl.
*A61B 34/00* (2016.01)
*A61B 90/00* (2016.01)
(Continued)

(52) U.S. Cl.
CPC .............. *A61B 34/71* (2016.02); *A61B 34/25* (2016.02); *A61B 90/37* (2016.02);
(Continued)

(58) Field of Classification Search
CPC ......... A61B 34/00; A61B 34/25; A61B 34/71; A61B 90/37; A61B 2017/1205; A61F 2/95; A61F 2/958
See application file for complete search history.

(56) References Cited

U.S. PATENT DOCUMENTS 6,289,187 B1 9/2001 Swift et al.
7,772,541 B2 8/2010 Froggatt et al.
(Continued)

FOREIGN PATENT DOCUMENTS

WO WO-2011143022 A1 11/2011
WO WO-2015142933 A1 9/2015
(Continued)

OTHER PUBLICATIONS

International Preliminary Report on Patentability for Application No. PCT/US2019/054718, mailed on Apr. 15, 2021, 11 pages.
(Continued)

*Primary Examiner* — Vi X Nguyen
(74) *Attorney, Agent, or Firm* — Haynes & Boone, LLP

(57) ABSTRACT

A medical instrument system is provided. The medical instrument system includes an instrument manipulator configured to control a pose of a medical instrument with respect to a patient anatomy. The medical instrument system further includes a support structure configured to control a pose of the instrument manipulator. The medical instrument system further includes a control system including a processor. The control system is configured to: receive data for determining a shape of a length of the medical instrument; compare the shape of the length of the medical instrument with a threshold value; determine if the shape of the length of the medical instrument is beyond the threshold value; and provide instructions for adjusting a position of the instrument manipulator based on the determination.

20 Claims, 46 Drawing Sheets

Related U.S. Application Data

(60) Provisional application No. 62/819,139, filed on Mar. 15, 2019, provisional application No. 62/741,800, filed on Oct. 5, 2018.

(51) Int. Cl.

| | |
|---|---|
| *A61M 25/01* | (2006.01) |
| *A61B 34/10* | (2016.01) |
| *A61B 34/20* | (2016.01) |
| *A61B 34/30* | (2016.01) |
| *A61B 34/35* | (2016.01) |

(52) U.S. Cl.
CPC .... *A61M 25/0113* (2013.01); *A61B 2034/107* (2016.02); *A61B 2034/2051* (2016.02); *A61B 2034/301* (2016.02); *A61B 34/35* (2016.02); *A61B 2034/715* (2016.02)

(56) References Cited

U.S. PATENT DOCUMENTS

| | | | |
|---|---|---|---|
| 8,900,131 B2 | 12/2014 | Chopra et al. | |
| 10,022,192 B1* | 7/2018 | Ummalaneni | A61B 5/06 |
| 10,512,515 B2 | 12/2019 | Bailey | |
| 2004/0254566 A1 | 12/2004 | Plicchi et al. | |
| 2006/0165841 A1 | 7/2006 | Golz | |
| 2007/0137371 A1 | 6/2007 | Devengenzo et al. | |

| | | | |
|---|---|---|---|
| 2007/0208252 A1* | 9/2007 | Makower | A61B 6/032 606/198 |
| 2008/0046122 A1 | 2/2008 | Manzo et al. | |
| 2014/0107666 A1 | 4/2014 | Madhani et al. | |
| 2018/0092701 A1 | 4/2018 | Fenech | |
| 2018/0110581 A1 | 4/2018 | Kamata et al. | |
| 2022/0008152 A1 | 1/2022 | Rohr Daniel et al. | |

FOREIGN PATENT DOCUMENTS

| | | |
|---|---|---|
| WO | WO-2016018618 A1 | 2/2016 |
| WO | WO-2016191298 A1 | 12/2016 |
| WO | WO-2017160458 A1 | 9/2017 |
| WO | WO-2018005680 A1 | 1/2018 |
| WO | WO-2018009841 A1 | 1/2018 |
| WO | WO-2018132386 A1 | 7/2018 |
| WO | WO-2018145100 A1 | 8/2018 |
| WO | WO-2019018736 A2 | 1/2019 |
| WO | WO-2019027922 A1 | 2/2019 |

OTHER PUBLICATIONS

International Search Report and Written Opinion for Application No. PCT/US2019/054718, mailed Mar. 13, 2020, 17 pages.
Invitation to Pay Additional Fees and Partial International Search Report for PCT/US2019/054718, mailed Jan. 20, 2020, 13 pages.
Vertut, J., and Coiffet, P., "Robot Technology: Teleoperation and Robotics Evolution and Development," English translation, Prentice-Hall, Inc., Inglewood Cliffs, NJ, USA 1986, vol. 3A, 332 pages.

* cited by examiner

406

408

SET-UP

ATTACH ACCESSORIES

① ATTACH CATHETER GUIDE

② ATTACH CATHETER
WAIT FOR CATHETER TESTS TO FINISH.

③ ATTACH VISION PROBE
THREAD VISION PROBE ADAPTER ONTO VISION PROBE.
ATTACH VISION PROBE TO ARM.
INSERT VISION PROBE THROUGH CATHETER.

610

DO NOT TOUCH CATHETER DURING SELF-TESTS

PERFORMING SYSTEM TESTS

SET-UP

LOAD PLAN

① INSERT USB DRIVE INTO CONTROLLER

② CHOOSE PATIENT ON TOUCHSCREEN

③ CHECK PATIENT PLAN AND ID
   CONFIRM ON TOUCHSCREEN

620

621

240

241  245  246

244  243

240

241  246  247

244  245

SYSTEMS AND METHODS FOR POSITIONING MEDICAL INSTRUMENTS

CROSS-REFERENCE TO RELATED APPLICATIONS

This application is a continuation of U.S. patent application Ser. No. 17/279,208, filed Mar. 24, 2021, which is the U.S. national phase of International Application No. PCT/US2019/054718, filed Oct. 4, 2019, which designates the U.S. and claims priority to and the benefit of U.S. Provisional Application 62/741,800, filed Oct. 5, 2018, and U.S. Provisional Application 62/819,139, filed Mar. 15, 2019, all of which are incorporated by reference herein in their entirety.

TECHNICAL FIELD

The present disclosure is directed to systems and methods for controlling medical instruments.

BACKGROUND

Minimally invasive medical techniques are intended to reduce an amount of tissue that is damaged during medical procedures, thereby reducing patient recovery time, discomfort, and harmful side effects. Such minimally invasive techniques may be performed through natural orifices in a patient anatomy or through one or more surgical incisions. Through these natural orifices or incisions, an operator (e.g., a physician) may insert minimally invasive medical instruments (including surgical, diagnostic, therapeutic, or biopsy instruments) to reach a target tissue location. One such minimally invasive technique is to use a flexible and/or steerable elongate device, such as a flexible catheter, that can be inserted into anatomic passageways and navigated toward a region of interest within the patient anatomy. Control of such an elongate device by an operator involves the management of several degrees of freedom including at least the management of insertion and retraction of the elongate device with respect to the patient anatomy, as well as steering of the device. Versatile systems and methods for instrument control are needed to address these and other challenges.

SUMMARY

The embodiments of the invention are best summarized by the claims that follow the description.

Consistent with some embodiments, a medical instrument system comprises an instrument manipulator configured to control a position of a medical instrument with respect to a base. The instrument manipulator comprises an instrument carriage comprising a medical instrument connector configured to engage the medical instrument. The instrument carriage is configured to translate along a linear axis to advance or retract the medical instrument with respect to the base. The medical instrument system also comprises an insertion stage slideably engaged with the instrument carriage along the linear axis. The insertion stage has a drive assembly comprising a drive belt and a drive motor configured to drive the drive belt. The base is fixedly coupled to the drive belt. The medical instrument system also comprises a connecting element having a distal end fixedly coupled to the drive belt and a proximal end fixed to the instrument carriage.

Consistent with some embodiments, a medical instrument system comprises an instrument manipulator configured to control a pose of a medical instrument with respect to a patient anatomy and a support structure configured to control a pose of the instrument manipulator. The medical instrument system also comprises a control system including a processor configured to: receive data for determining a shape of a length of the medical instrument; compare the shape of the length of the medical instrument with a threshold value; determine if the shape of the length of the medical instrument is beyond the threshold value; and provide instructions for adjusting a position of the instrument manipulator based on the determination.

It is to be understood that both the foregoing general description and the following detailed description are illustrative and explanatory in nature and are intended to provide an understanding of the present disclosure without limiting the scope of the present disclosure. In that regard, additional aspects, features, and advantages of the present disclosure will be apparent to one skilled in the art from the following detailed description.

BRIEF DESCRIPTIONS OF THE DRAWINGS

FIG. 1 is a simplified diagram of a teleoperated medical system according to some embodiments.

FIG. 2 illustrates various aspects of a medical system according to an embodiment of the present disclosure. FIG. 2A illustrates a manipulator assembly including an instrument manipulator coupled to a support structure according to an embodiment of the present disclosure. FIG. 2B illustrates a system cart in a stowed configuration according to an embodiment of the present disclosure.

Figure 1:
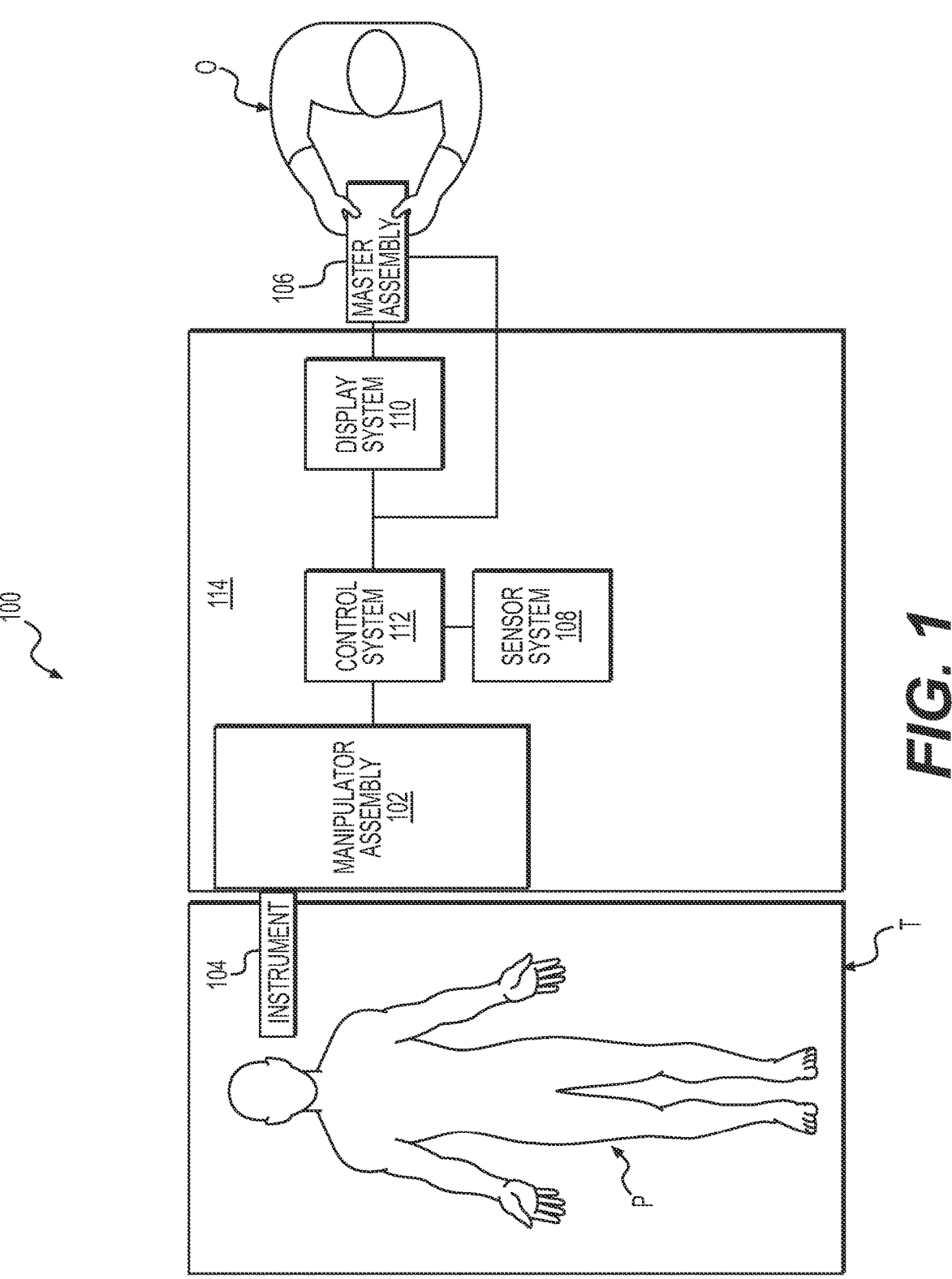

Embodiments of the present disclosure and their advantages are best understood by referring to the detailed description that follows. It should be appreciated that like reference numerals are used to identify like elements illustrated in one or more of the figures, wherein showings therein are for purposes of illustrating embodiments of the present disclosure and not for purposes of limiting the same.

DETAILED DESCRIPTION

In the following description, specific details are set forth describing some embodiments consistent with the present disclosure. Numerous specific details are set forth in order to provide a thorough understanding of the embodiments. It will be apparent, however, to one skilled in the art that some embodiments may be practiced without some or all of these specific details. The specific embodiments disclosed herein are meant to be illustrative but not limiting. One skilled in the art may realize other elements that, although not specifically described here, are within the scope and the spirit of this disclosure. In addition, to avoid unnecessary repetition, one or more features shown and described in association with one embodiment may be incorporated into other embodiments unless specifically described otherwise or if the one or more features would make an embodiment non-functional.

In some instances well known methods, procedures, components, and circuits have not been described in detail so as not to unnecessarily obscure aspects of the embodiments.

This disclosure describes various instruments and portions of instruments in terms of their state in three-dimensional space. As used herein, the term "position" refers to the location of an object or a portion of an object in a three-dimensional space (e.g., three degrees of translational freedom along Cartesian x-, y-, and z-coordinates). As used herein, the term "orientation" refers to the rotational placement of an object or a portion of an object (three degrees of rotational freedom—e.g., roll, pitch, and yaw). As used herein, the term "pose" refers to the position of an object or a portion of an object in at least one degree of translational freedom and to the orientation of that object or portion of the object in at least one degree of rotational freedom (up to six total degrees of freedom). As used herein, the term "shape" refers to a set of poses, positions, or orientations measured along an object.

FIG. 1 is a simplified diagram of a teleoperated medical system 100 according to some embodiments. In some embodiments, teleoperated medical system 100 may be suitable for use in, for example, surgical, diagnostic, therapeutic, or biopsy procedures. While some embodiments are provided herein with respect to such procedures, any reference to medical or surgical instruments and medical or surgical methods is non-limiting. The systems, instruments, and methods described herein may be used for animals, human cadavers, animal cadavers, portions of human or animal anatomy, non-surgical diagnosis, as well as for industrial systems and general robotic or teleoperational systems.

As shown in FIG. 1, teleoperated medical system 100 generally includes a manipulator assembly 102 for operating a medical instrument 104 in performing various procedures on a patient P. The manipulator assembly 102 may be teleoperated, non-teleoperated, or a hybrid teleoperated and non-teleoperated assembly with select degrees of freedom of motion that may be motorized and/or teleoperated and select degrees of freedom of motion that may be non-motorized and/or non-teleoperated. Manipulator assembly 102 can be mounted to an operating table T, or to a main support 114 (e.g. a cart, stand, second table, and or the like). A master assembly 106 allows an operator (e.g., a surgeon, a clinician, or a physician as illustrated in FIG. 1) to view the interventional site and to control manipulator assembly 102.

Master assembly 106 may be located at an operator console which is usually located in the same room as operating table T, such as at the side of a surgical table on which patient P is located. However, it should be understood that operator O can be located in a different room or a completely different building from patient P. Master assembly 106 generally includes one or more control devices for controlling manipulator assembly 102. The control devices may include any number of a variety of input devices, such as joysticks, trackballs, data gloves, trigger-guns, hand-operated controllers, voice recognition devices, body motion or presence sensors, and/or the like. To provide operator O a strong sense of directly controlling instruments 104 the control devices may be provided with the same degrees of freedom as the associated medical instrument 104. In this manner, the control devices provide operator O with telepresence or the perception that the control devices are integral with medical instruments 104.

In some embodiments, the control devices may have more or fewer degrees of freedom than the associated medical instrument 104 and still provide operator O with telepresence. In some embodiments, the control devices may optionally be manual input devices which move with six degrees of freedom, and which may also include an actuatable handle for actuating instruments (for example, for closing grasping jaws, applying an electrical potential to an electrode, delivering a medicinal treatment, and/or the like).

Manipulator assembly 102 supports medical instrument 104, and may include a kinematic structure of one or more non-servo controlled links (e.g., one or more links that may be manually positioned and locked in place, generally referred to as a set-up structure), and/or one or more servo controlled links (e.g., one or more powered links that may be controlled in response to commands from the control system), and a manipulator. Manipulator assembly 102 may optionally include a plurality of actuators or motors that drive inputs on medical instrument 104 in response to commands from the control system (e.g., a control system 112). The actuators may optionally include drive systems that when coupled to medical instrument 104 may advance medical instrument 104 into a naturally or surgically created anatomic orifice. Other drive systems may move the distal end of medical instrument 104 in multiple degrees of freedom, which may include three degrees of linear motion (e.g., linear motion along the X, Y, Z Cartesian axes) and in three degrees of rotational motion (e.g., rotation about the X, Y, Z Cartesian axes). Additionally, the actuators can be used to actuate an articulable end effector of medical instrument 104 for grasping tissue in the jaws of a biopsy device and/or the like. Actuator position sensors such as resolvers, encoders, potentiometers, and other mechanisms may provide sensor data to medical system 100 describing the rotation and orientation of the motor shafts. This position sensor data may be used to determine motion of the objects manipulated by the actuators.

Teleoperated medical system 100 may include a sensor system 108 with one or more sub-systems for receiving information about the instruments of manipulator assembly 102. Such sub-systems may include a position/location sensor system (e.g., an electromagnetic (EM) sensor system); a shape sensor system for determining the position, orientation, speed, velocity, pose, and/or shape of a distal end and/or of one or more segments along a flexible body that may make up medical instrument 104; and/or a visualization system for capturing images from the distal end of medical instrument 104.

Teleoperated medical system 100 also includes a display system 110 for displaying an image or representation of the surgical site and medical instrument 104 generated by sub-systems of sensor system 108, recorded pre-operatively or intra-operatively using image data from imaging technology and/or a real time image such as, computed tomography (CT), magnetic resonance imaging (MRI), fluoroscopy, thermography, ultrasound, optical coherence tomography (OCT), thermal imaging, impedance imaging, laser imaging, nanotube X-ray imaging, endoscopic images, and/or the like. The pre-operative or intra-operative image data may be presented as two-dimensional, three-dimensional, or four-dimensional (including e.g., time based or velocity-based information) images and/or as images from models created from the pre-operative or intra-operative image data sets. Display system 110 and master assembly 106 may be oriented so operator O can control medical instrument 104 and master assembly 106 with the perception of telepresence.

Teleoperated medical system 100 may also include control system 112. Control system 112 includes at least one memory and at least one computer processor (not shown) for effecting control between medical instrument 104, master assembly 106, sensor system 108, and display system 110. Control system 112 also includes programmed instructions (e.g., a non-transitory machine-readable medium storing the instructions) to implement some or all of the methods described in accordance with aspects disclosed herein, including instructions for providing information to display system 110. While control system 112 is shown as a single block in the simplified schematic of FIG. 1, the system may include two or more data processing circuits with one portion of the processing optionally being performed on or adjacent to manipulator assembly 102, another portion of the processing being performed at master assembly 106, and/or the like. The processors of control system 112 may execute instructions comprising instruction corresponding to processes disclosed herein and described in more detail below. Any of a wide variety of centralized or distributed data processing architectures may be employed. Similarly, the programmed instructions may be implemented as a number of separate programs or subroutines, or they may be integrated into a number of other aspects of the teleoperational systems described herein. In one embodiment, control system 112 supports wireless communication protocols such as Bluetooth, IrDA, HomeRF, IEEE 802.11, DECT, and Wireless Telemetry.

In some embodiments, control system 112 may receive force and/or torque feedback from medical instrument 104. Responsive to the feedback, control system 112 may transmit signals to master assembly 106. In some examples, control system 112 may transmit signals instructing one or more actuators of manipulator assembly 102 to move medical instrument 104. Medical instrument 104 may extend into an internal surgical site within the body of patient P via openings in the body of patient P. Any suitable conventional and/or specialized actuators may be used. In some examples, the one or more actuators may be separate from, or integrated with, manipulator assembly 102. In some embodiments, the one or more actuators and manipulator assembly 102 are provided as part of a teleoperational cart positioned adjacent to patient P and operating table T.

Control system 112 may optionally further include a virtual visualization system to provide navigation assistance to operator O when controlling medical instrument 104 during an image-guided surgical procedure. Virtual navigation using the virtual visualization system may be based upon reference to an acquired preoperative or intraoperative dataset of anatomic passageways.

During a virtual navigation procedure, sensor system 108 may be used to compute an approximate location of medical instrument 104 with respect to the anatomy of patient P. The location can be used to produce both macro-level (external) tracking images of the anatomy of patient P and virtual internal images of the anatomy of patient P. The system may implement one or more electromagnetic (EM) sensor, fiber optic sensors, and/or other sensors to register and display a medical implement together with preoperatively recorded surgical images, such as those from a virtual visualization system. For example, PCT Publication WO 2016/191298 (published Dec. 1, 2016) (disclosing "Systems and Methods of Registration for Image Guided Surgery"), which is incorporated by reference herein in its entirety, discloses such one system. Various systems and methods for monitoring the shape and relative position of an optical fiber in three dimensions are described in U.S. patent application Ser. No. 11/180,289 (filed Jul. 12, 2005) (disclosing "Fiber optic position and shape sensing device and method relating thereto"); U.S. patent application Ser. No. 12/047,056 (filed on Jul. 16, 2004) (disclosing "Fiber-optic shape and relative position sensing"); and U.S. Pat. No. 6,289,187 (filed on Jun. 17, 1998) (disclosing "Optical fibre bend sensor"), which are all incorporated by reference herein in their entireties.

Teleoperated medical system 100 may further include optional operations and support systems (not shown) such as illumination systems, steering control systems, irrigation systems, and/or suction systems. In some embodiments, teleoperated medical system 100 may include more than one manipulator assembly and/or more than one master assembly. The exact number of teleoperational manipulator assemblies will depend on the surgical procedure and the space constraints within the operating room, among other factors. Master assembly 106 may be collocated or they may be positioned in separate locations. Multiple master assemblies allow more than one operator to control one or more teleoperational manipulator assemblies in various combinations.

In some embodiments, the manipulator assembly 102, control system 112, sensor system 108, and display system 110 may all be supported by support structure 114 or may be integrated into support structure 114. Alternatively, one or more components (e.g., manipulator assembly 102, control system 112, sensor system 108, and/or display system 110) may be mounted to the operating table T or integrated into the master assembly 106.

Figure 2:
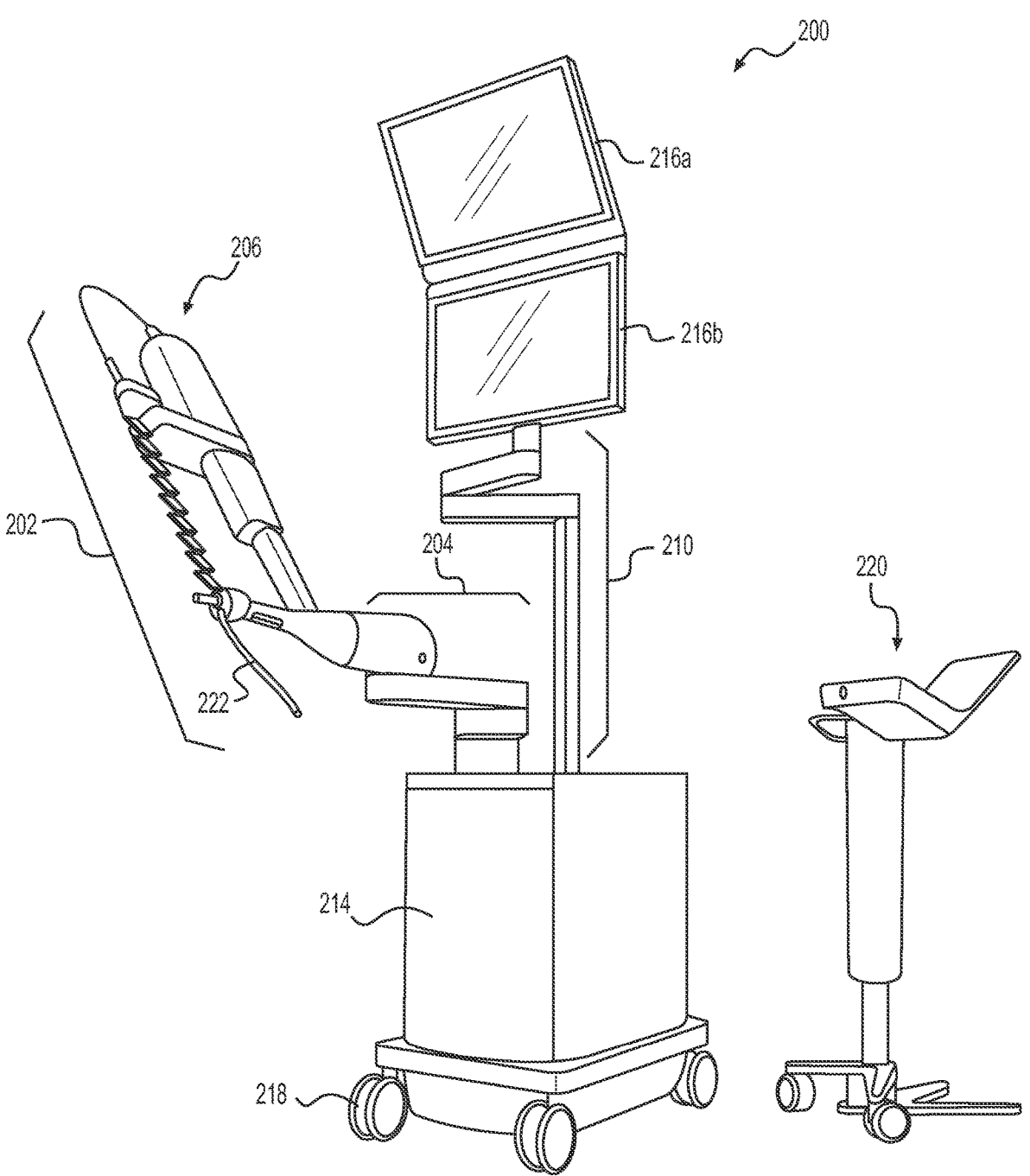

FIG. 2 illustrates, as an example of a teleoperated medical system 100, a medical system 200 according to an embodiment of the present disclosure. Medical system 200 can include a master control 220 and a system cart 214 which supports a manipulator assembly 202 and a display system 216. The manipulator assembly can be configured to support and position an elongate device such as elongate device 222. Various elongate devices are described in PCT/US18/43041 (filed Jul. 20, 2018) (disclosing "Flexible elongate device systems and methods"), which is incorporated by reference herein in its entirety.

The system cart 214 is mounted on a set of wheels 218 to allow positioning of the system cart 214 at a desired location relative to an operating table (e.g., operating table T) and the patient (e.g., patient P). The system cart 214 also supports display system 216 which includes monitor support arm 210, and display monitors 216a, 216b. Monitor support arm 210 includes multiple links and joints which provide adjustable positioning of display monitors 216a and 216b in the vertical and lateral directions, as well as rotationally about a vertical axis relative to the system cart 214, to position either monitor 216a, 216b at a desired viewing angle from the operator's point of view. Display system 216 may provide for up to 360 degree rotation, e.g. 0-180 degrees rotation, of monitor 216a about a horizontal axis allowing monitor 216a to be positioned at a desired viewing angle or be folded and stowed in a collapsed configuration against monitor 216b for storage (see FIG. 2B). Various systems and methods relating to a system cart and monitors are described in PCT/US18/12995 (filed Jan. 9, 2018) (disclosing "Systems and methods for using a robotic medical system"), which is incorporated by reference herein in its entirety. The system cart 214 may include hardware (e.g., processor(s), firmware) and/or or software to perform functions for performing shape-sensing with respect to a flexible elongate device.

The medical system 200 of FIG. 2 also includes a master control 220 according to one embodiment, some aspects of which are discussed above with respect to master assembly 106. The master control 220 may include various input controls for an operator (e.g., operator O, FIG. 1) to use for interactively controlling operations of the manipulator assembly 202, for example functions performed by the instrument manipulator 206. In some embodiments, the master control 220 includes a scroll wheel and a trackball. In an example implementation, the scroll wheel may be rolled forwards or backwards in order to control the advancement or retraction of a medical instrument (e.g., elongate device 222) with respect to the patient anatomy, and the trackball may be rolled in various directions by an operator in order to steer the position of the distal end portion and/or distal tip of the elongate device 222, for example to control bend or articulation. Various systems and methods related to motion control consoles are described in PCT/US18/44419 (filed Jul. 30, 2018) (directed to "Systems and methods for safe operation of a device") and U.S. patent application Ser. No. 16/049,640 (filed Jul. 30, 2018) (disclosing "Systems and methods for steerable elongate device"), which are incorporated by reference herein in their entireties.

Figure 2A:
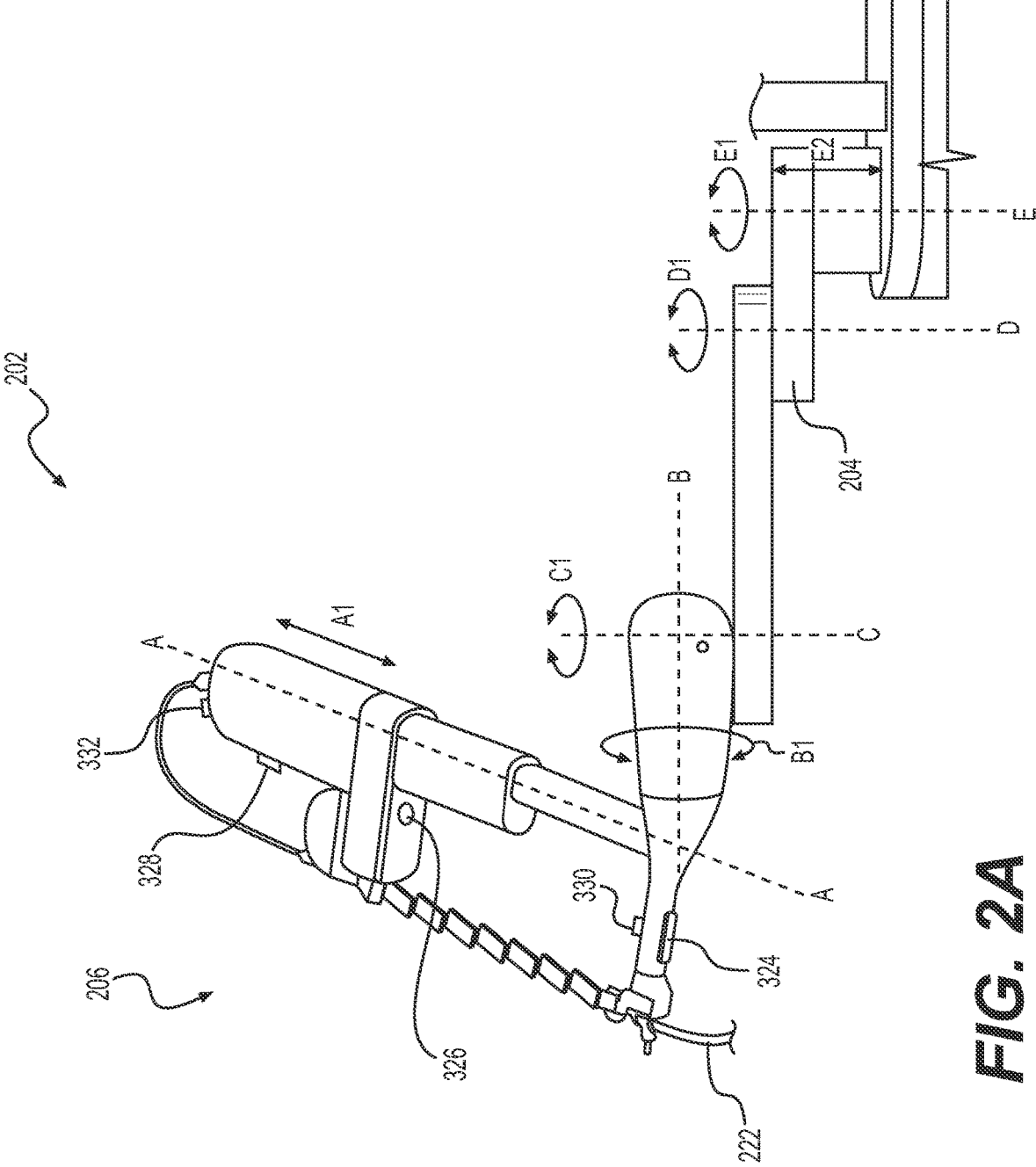

FIG. 2A illustrates manipulator assembly 202 including an instrument manipulator 206 coupled to the support structure 204. The support structure 204 includes multiple coupled links that may be positioned by swiveling about joints, and extending, or retracting vertically, among other possible changes in direction and orientation, in order to place the instrument manipulator 206 at an optimal location and orientation. The links of support structure 204 may include non-servo controlled links (e.g., which may be manually positioned and locked into place) and/or one or more servo-controlled links (e.g., powered links that may be controlled in response to commands from a control system). In some embodiments, the links of the support structure 204 may be positioned using electronic circuitry and controls, including motors, to avoid manual intervention. In some embodiments, the links may be locked in place or unlocked to be manually manipulated by an operator interacting with switches, buttons, or other types of input devices as will be described in more detail below.

As shown in FIG. 2A, the instrument manipulator 206 according to various embodiments is configured to couple to elongate device 222. Support structure provides adjustments to position the instrument manipulator 206 at an optimal position and orientation and/or position elongate device 222 to optimally position the elongate device 222 relative to patient anatomy or other medical devices. For example, support structure 204 may provide for rotation E1 about axis E, extension/retraction E2 along axis E, rotation D1 about axis D, and rotation C1 about axis C, and rotation B1, about axis B, to position instrument manipulator 206 in a desired position relative to table T, medical devices, and/or patient P. In some embodiments, optimal location and orientation can include alignment of the instrument manipulator 206 with respect to the patient anatomy, for example, for optimal positioning of the elongate device 222 to minimize friction of the elongate device 22 positioned within patient anatomy (e.g. anatomical openings, patient vasculature, patient endoluminal passageways, etc.) or within medical devices coupled to patient anatomy (e.g. cannulas, trocars, endotracheal tubes (ETT), laryngeal esophageal masks (LMA), etc.). In other embodiments, optimal location and orientation of the instrument manipulator 206 can additionally or alternatively include optimizing operator (e.g. operator O) ergonomics by providing sufficient operator workspace and/or ergonomic access to elongate device 222 when utilizing various medical tools such as needles, graspers, scalpels, grippers, ablation probes, visualization probes, and/or the like, with the elongate device 222.

Instrument manipulator 206 can be further configured to provide teleoperational, robotic control, or other form of electronic controlled translation or manual translation A1 along axis A to provide for insertion and retraction of elongate device 222 with respect to patient anatomy.

Each adjustment (e.g., A1, B1, C1, D1, E1, and E2) can be actuated by either robotic control or by manual intervention by an operator. For example, in one embodiment, each rotational or linear adjustment may be maintained in a stationary configuration using brakes such that depression of one or more buttons and switches releases one or more corresponding brakes allowing an operator to manually position the instrument manipulator. Additionally or alternatively, one or more adjustments may be controlled by one or more actuators (e.g., motors) such that an operator may use a button or switch to actuate a motor to alter the support structure 204 and/or the instrument manipulator 206 in a desired manner to position the manipulator assembly 202 in a desired configuration to provide an optimal position and orientation of the instrument manipulator 206.

In one example, referring again to FIG. 2A, a handle input device 324 can be manually actuated in order to unlock the support structure 204 for free movement and adjustment of the coupled links to allow for adjustments C1, D1, E1, and/or E2. In another example, an input button 326 unlocks linear adjustment A1 for manual translational movement by an operator, rather than by robotic control. The instrument manipulator 206 may be configured such that when the input button 326 is pressed, the operator may adjust the instrument manipulator 206 along the linear axis A that corresponds to inserting or retracting a medical instrument (e.g., elongate device 222). In some embodiments, for safety purposes, the instrument manipulator 206 may only be manually movable in one direction along the linear axis A, such as retraction and is not manually movable in the direction along the linear axis A that corresponds to insertion of the medical instrument, in order to prevent an operator from inadvertently or undesirably advancing the medical instrument with respect to the patient anatomy, which may result in harm to the patient.

In another example, robotic control of the rotational motion B1 can be actuated by depressing a switch 330, which as shown is a rocker switch, that may be depressed on one lateral side or the other. Depressing a first side of the rocker switch initiates powered rotation of the instrument manipulator 206 in a first direction of rotation about axis B and depressing the other side of the rocker switch initiates powered rotation of the instrument manipulator 206 in the other direction about axis B. In another example, a button 332, when depressed, releases brakes holding the instrument manipulator 206 in a current configuration and allows an operator to manually rotate the orientation of the instrument manipulator 206 about axis B.

In some embodiments buttons or switches on the instrument manipulator 206 may be used to alter display of visual indicators, markers, and or images shown on monitors 216a, 216b, and/or a touchscreen on master control 220. For example, referring again to FIG. 2A, actuating (e.g., pressing) an input button 328 can cause a marker to be placed in a rendered model of patient anatomy displayed on monitor 216a and/or monitor 216b. The marker could correspond to an area within the patient at which a procedure (e.g., biopsy) has been performed, or otherwise indicates an actual location within the patient anatomy where the medical instrument has been. In some embodiments, a virtual navigational marker may be dynamically referenced with a registered preoperative or concurrent images or models. Systems and methods for registration are provided in PCT Publication WO 2016/191298 (published Dec. 1, 2016) (disclosing "Systems and Methods of Registration for Image Guided Surgery"), and in U.S. patent application Ser. No. 13/107, 562, filed May 13, 2011, disclosing, "Medical System Providing Dynamic Registration of a Model of an Anatomic Structure for Image-Guided Surgery," which are incorporated by reference herein in their entireties.

Figure 2B:
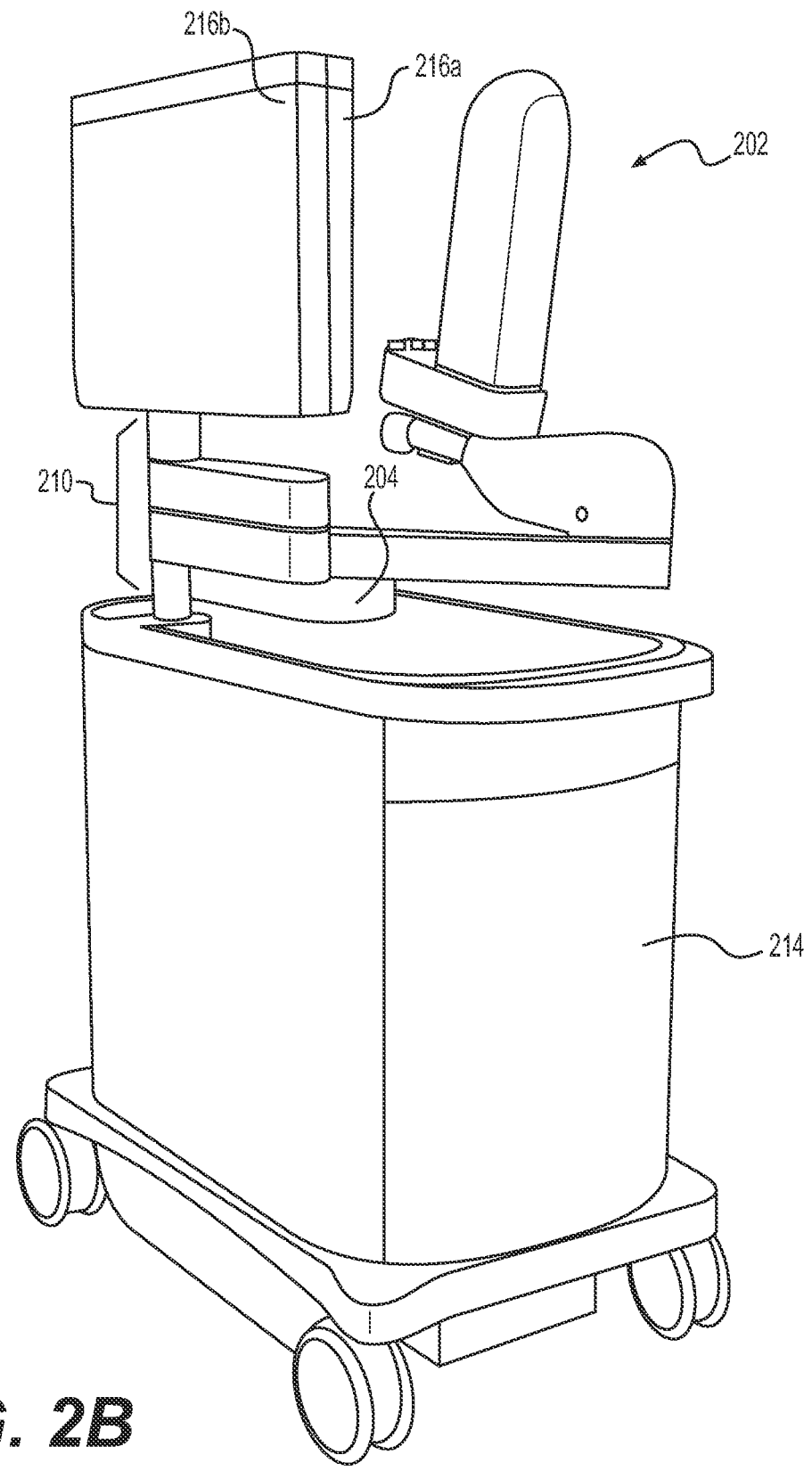

FIG. 2B illustrates system cart 214 in a stowed configuration. As shown, the monitor support arm 210 is vertically retracted, and display monitor 216a is folded and stowed in a collapsed configuration against display monitor 216b. The manipulator assembly 202 has been placed into a stowed configuration by translating portions of the instrument manipulator 206 in a telescoping manner along axis A, for example as will described in further detail with respect to embodiments of FIGS. 3A and 3B. The elongate device 222 and various other detachable accessories of the instrument manipulator 206 configuration shown in FIG. 2 have been removed. The multiple coupled links of the support structure 204 have been adjusted in position relative to each other to place the manipulator assembly 202 into the stowed arrangement.

Figure 3A:
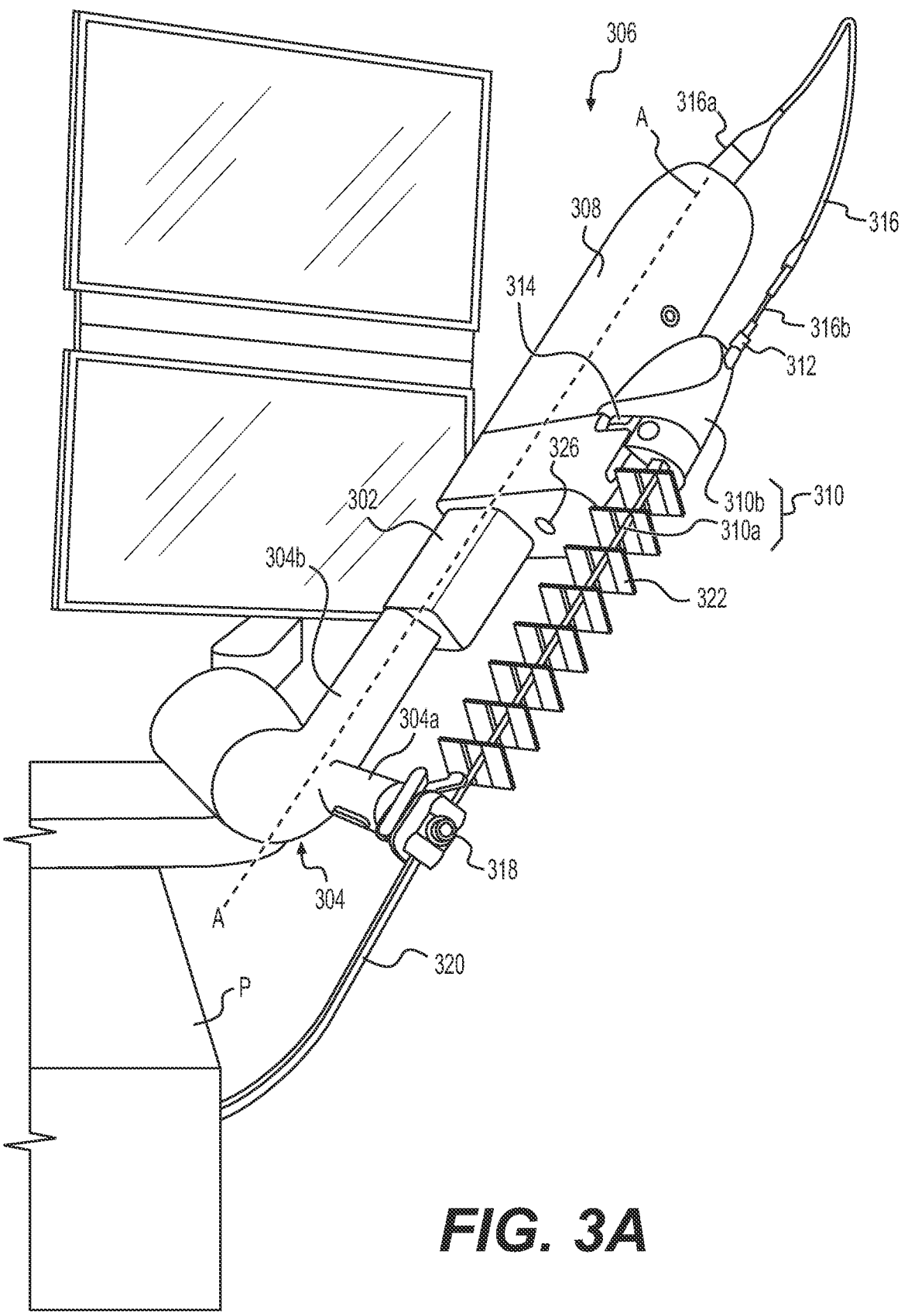
FIGS. 3A and 3B illustrate various aspects of an instrument manipulator according to an embodiment of the present disclosure.
Figure 3B:
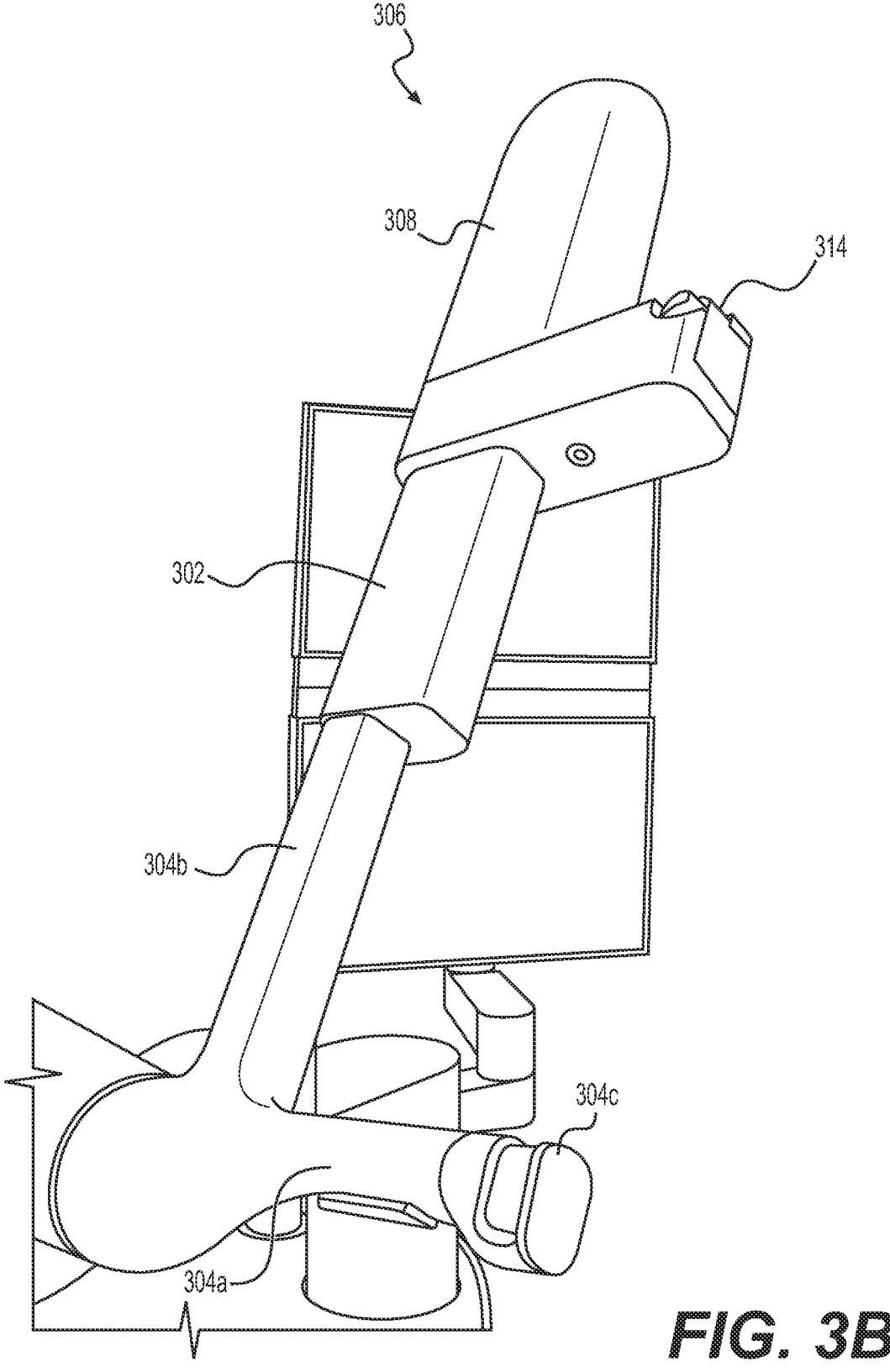

FIGS. 3A and 3B illustrate an example of an instrument manipulator 306, which can be substantially similar to instrument manipulator 206. The instrument manipulator 306 includes a base 304, an insertion stage 302, and an instrument carriage 308 to which an elongate device assembly 310, is coupled. The instrument manipulator 306 provides for insertion and retraction of the elongate device assembly 310, with respect to the patient anatomy, by moving the instrument carriage 308 and insertion stage 302 in a telescoping manner relative to base 304 and along the linear axis A. The base 304 includes a shaft portion 304a and main portion 304b. As will be described in greater detail below, the shaft portion 304a removably couples to a device connector 318 which receives the elongate device 310a. The insertion stage 302 is coupled to the main portion 304b of the base 304 and translates along the main portion 304b. The instrument carriage 308 is coupled to and translates along the insertion stage 302. As shown, the insertion stage 302 and instrument carriage 308 have respective protective coverings and/or and housings, and when the instrument manipulator 306 is moved along the axis A, the respective coverings and/or housings at least partially overlap with each other, thereby effecting a telescoping effect, to facilitate scaling and optimal slidable fit.

The elongate device assembly 310 can include an elongate device 310a and a control assembly 310b. The instrument carriage 308 couples to control assembly 310b at an instrument interface 314 of the instrument carriage 308. Further details of the instrument interface 314, according to some embodiments, are discussed with reference to FIGS. 4A and 4B. The instrument manipulator 306 also couples to a probe assembly 316 which includes a probe 316b and a probe connector 316a. The probe assembly 316 may insert into a working lumen of the elongate device 310a through the connector 312 on the control assembly 310b and may run through the elongate device 310a. The probe 316b may include a viewing scope assembly that records concurrent or real-time images of an interventional site (which may be a surgical site, an internal surgical site, a procedure site, etc.) and provides the images to an operator (e.g., operator O, FIG. 1) through one or more displays (e.g., one or more displays of display system 110 in FIG. 1). The instrument carriage 308 may include electronic and optical components providing probe 316b endoscopic capabilities. In some embodiments, the probe assembly 316 may be detached from the instrument manipulator 306 and elongate device control assembly 310b, and removed from elongate device assembly 310. Alternative instruments such as biopsy needles, ablation tools, and other flexible instruments may be coupled to instrument manipulator 306 and/or elongate device assembly 310, through the elongate device 310 working lumen.

A device connector 318 can include a manipulator interface which can be removeably coupled to distal end portion 304c of base 304, a distal end which can be removeably coupled to a patient medical device 320, and a proximal end which can receive elongate device 310a. The patient medical device 320 (such as an endotracheal tube, a laryngeal mask airway, a cannula, etc.) can be fixed to patient anatomy to facilitate insertion of various medical devices into patient anatomy. For example, the patient medical device 320 may be an endotracheal tube inserted into the mouth and trachea of the patient P to help provide mechanical ventilation for the patient P and to provide a conduit for the elongate device 310*a* to be navigated within the lungs of the patient P to facilitate imaging, biopsy, and/or treatment. Various systems and methods related to device connectors are described in PCT/US2018/017085 (filed Feb. 6, 2018) (disclosing "Systems and methods for coupling components of a medical system"), which is incorporated by reference herein in its entirety. In some embodiments, the elongate device 310*a* runs through an elongate device guide 322, which is a selectively collapsible and extendable device that supports the length of the elongate device 310*a* during movement of the instrument carriage 308. Various systems and methods related to catheter guides such as elongate device guides are described in PCT/US2017/041160 (filed Jul. 7, 2017) (disclosing "Guide apparatus for delivery of an elongate device and methods of use"), which is incorporated by reference herein in its entirety.

In some embodiments, shape-sensing may be used, in conjunction with the rotation of a manipulator assembly as in accordance with embodiments described above, to ensure that the instrument manipulator is positioned at an angle of inclination that is optimal for minimizing the insertion forces, which may be friction forces, on the elongate device. For example, the determination can be performed to assess, based on the sensed shape of the elongate device and the angle of inclination of the manipulator assembly, whether the shape of the elongate device is oriented such that it is in, or is approaching, a problematic configuration that could have negative effects such as creating excessive friction in an endotracheal tube (e.g., endotracheal tube 320) or could cause disengagement of a device connector (e.g., device connector 318). Shape-sensing may be used in any other suitable manner, as needed.

A control system (e.g., control system 112, FIG. 1) with a memory and one or more programmable processors may be implemented to receive shape-sensing data from a shape-sensing system, indicating the shape along the length of the elongate device, and to receive data corresponding to the angle of inclination of the instrument manipulator, in order to make a determination, as described above, whether the shape of the elongate device is in or is approaching a problematic configuration. The shape of the elongate device and/or relative orientation of the instrument manipulator may be processed by comparing corresponding data to a threshold level or value. The control system may also be configured to, in response to the determination, output a visual indicator such as a colored light (e.g., red or green), a numerical value, a visual representation of the bend, or another type of visual indication that corresponds to, for example, whether there is a problematic relative orientation or not. The visual indicator may be displayed on a display system (e.g., display system 110, FIG. 1). The visual indicator may provide guidance for rotating the instrument manipulator based on the comparison of the shape of the elongate device and/or relative orientation of the instrument manipulator to the threshold level or value. The control system 112 may also be configured to provide instructions for automatically adjusting (e.g., rotating) the instrument manipulator based on the comparison of the shape of the elongate device and/or relative orientation of the instrument manipulator to the threshold level or value. In some embodiments, the instructions for adjusting the position of the instrument manipulator include instructions for automatically adjusting the support structure (e.g., support structure 114). Various systems and methods for monitoring the shape and relative position of an optical fiber are described in U.S.

patent application Ser. No. 11/180,289 (filed Jul. 12, 2005) (disclosing "Fiber optic position and shape sensing device and method relating thereto"); U.S. patent application Ser. No. 12/047,056 (filed on Jul. 16, 2004) (disclosing "Fiber-optic shape and relative position sensing"); and U.S. Pat. No. 6,289,187 (filed on Jun. 17, 1998) (disclosing "Optical fibre bend sensor"), which are all incorporated by reference herein in their entireties.

Figure 4A:
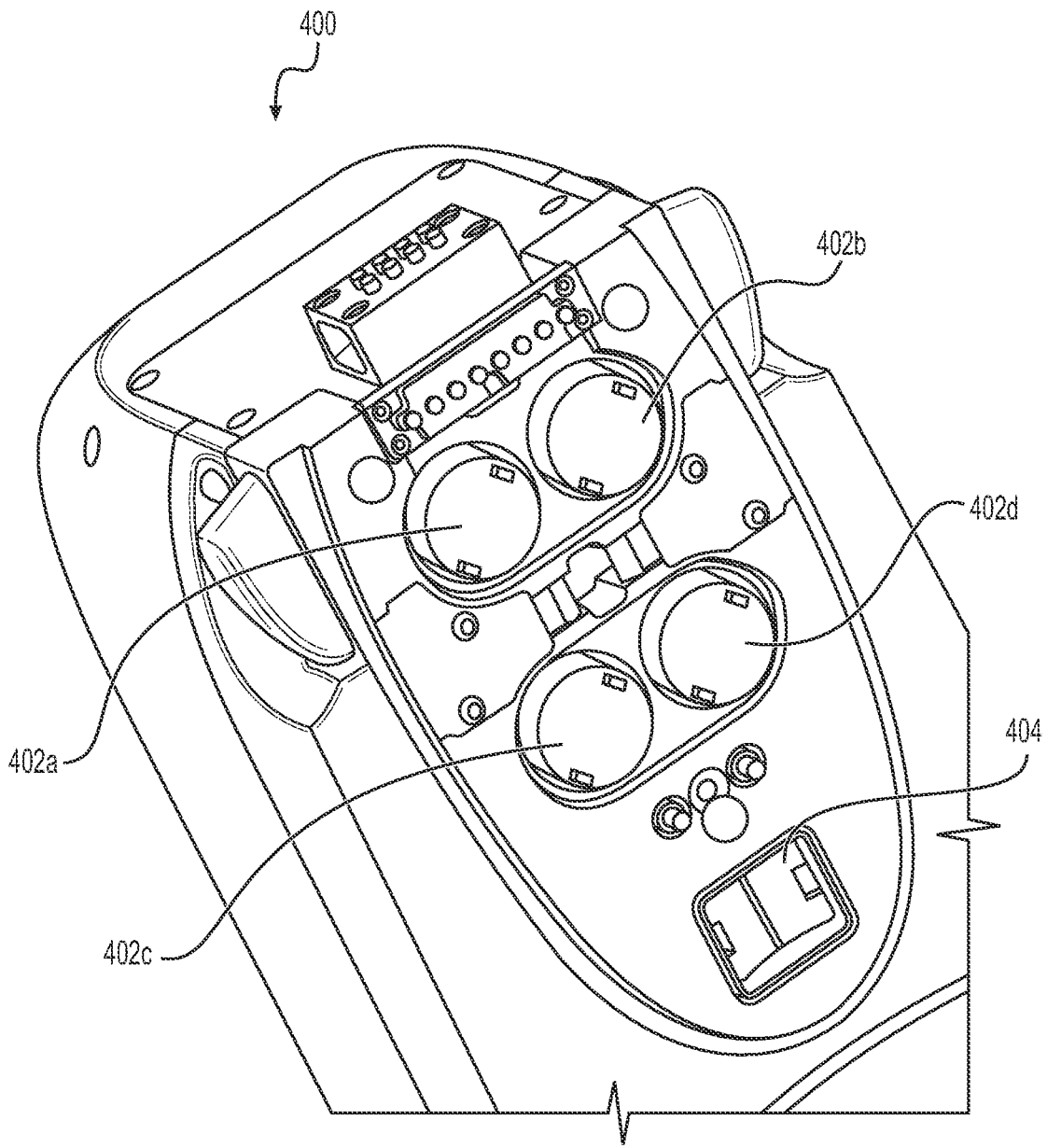
FIGS. 4A and 4B illustrate an instrument interface according to an embodiment of the present disclosure.

Now referring to one embodiment as shown in FIG. 4A, an instrument interface 400 (which may be substantially similar to instrument interface 314), includes a set of rotating input disks 402*a*, 402*b*, 402*c*, 402*d* that mate with corresponding pull wire capstans (not shown) of a control assembly (such as control assembly 310*b*) that may drive pull wires configured to steer the distal end portion of the elongate device. In some embodiments, the pull wires may run along the entire length of an elongate device to the distal end portion or distal tip of the elongate device. More details on control mechanisms for control systems for controlling elongate devices are provided in U.S. Patent Application No. 62/671,758 (disclosing "Control Mechanism of a Catheter Control System"), which is incorporated by reference herein in its entirety.

Figure 4B:
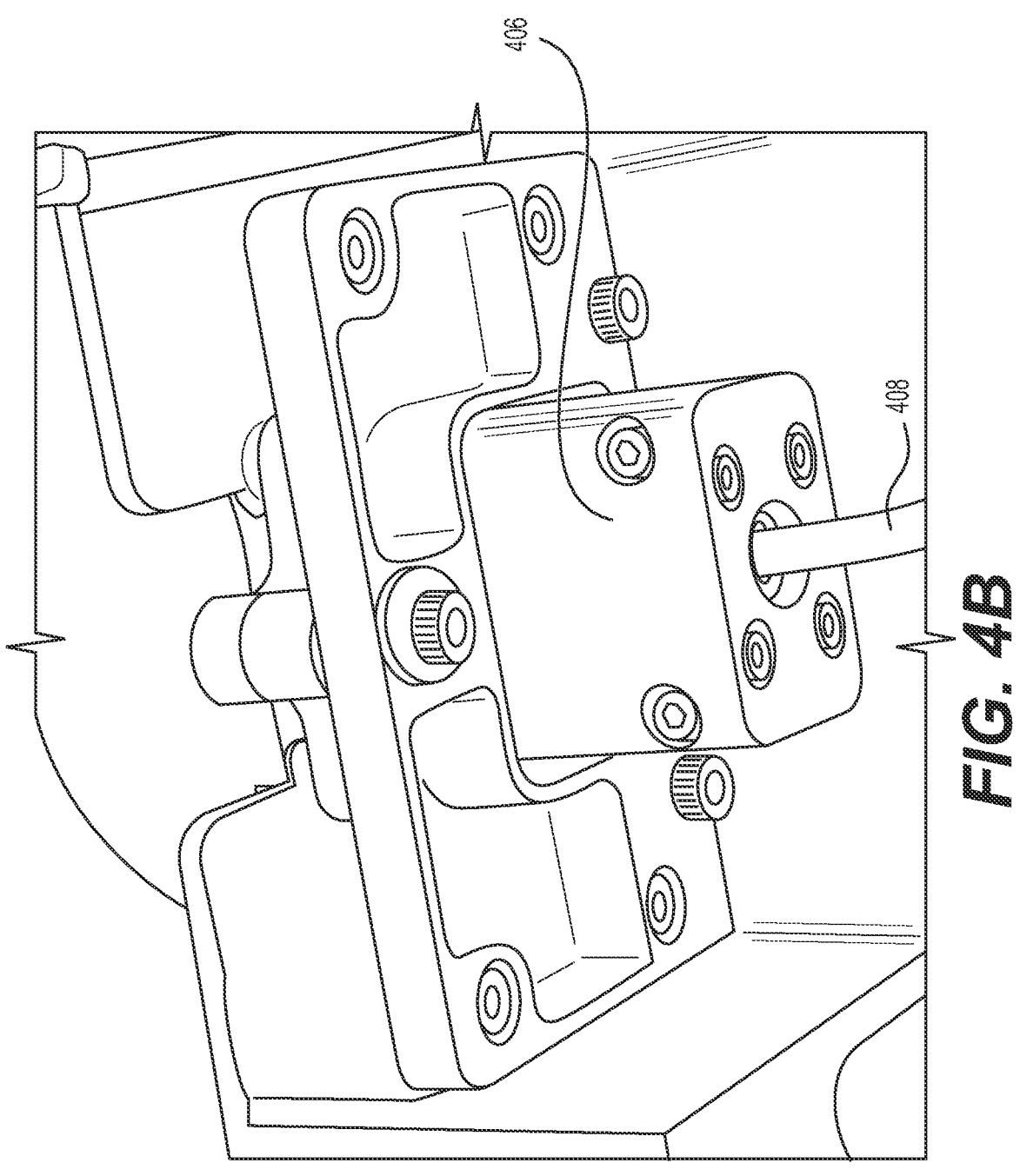

As shown, the instrument interface 400 includes a shuttered shape fiber connector 404. The shape fiber connector 404 connects with the shape fiber connection on a mating assembly. As shown in FIG. 4B, in some embodiments, the shuttered shape fiber connector 404 may be configured as a floating interface to enable easy connection of a fiber with forgiveness in multiple axes. Thus, when a fiber is being inserted into and connected to the shape fiber connector 404 of the instrument interface 400, an operator is not required to perfectly align the end of the fiber as it is moved into position, thereby providing some flexibility to the operator. Additionally, the floating interface prevents misalignment during installation from damaging the fiber and allows the fiber to make a proper and complete connection with the shape fiber connector 404. In this way, the shape fiber connector 404 on the instrument interface 400 may be self-aligning. This may allow the shape fiber connector 404 to connect with the shape fiber connection on the mating assembly without any adjustment and/or additional intervention by the operator O, the surgeon, and/or other personnel. In some embodiments, the shape fiber connector 404 is able to float in x- and y-directions (e.g., an x-y interface). The shape fiber connector 404 may also be able to float and/or pivot in a pitch motion. Therefore, the shape fiber connector 404 may be adjustable in three degrees of freedom. Details of some of the components facilitating the floating interface are shown in FIG. 4B. As shown, a spring-mounted control 406 engages and routes a fiber 408. The spring-mounted control 406 is configured to translate in the multiple directions and axes (e.g., the x- and y-directions and/or the pitch motion).

Figure 5A:
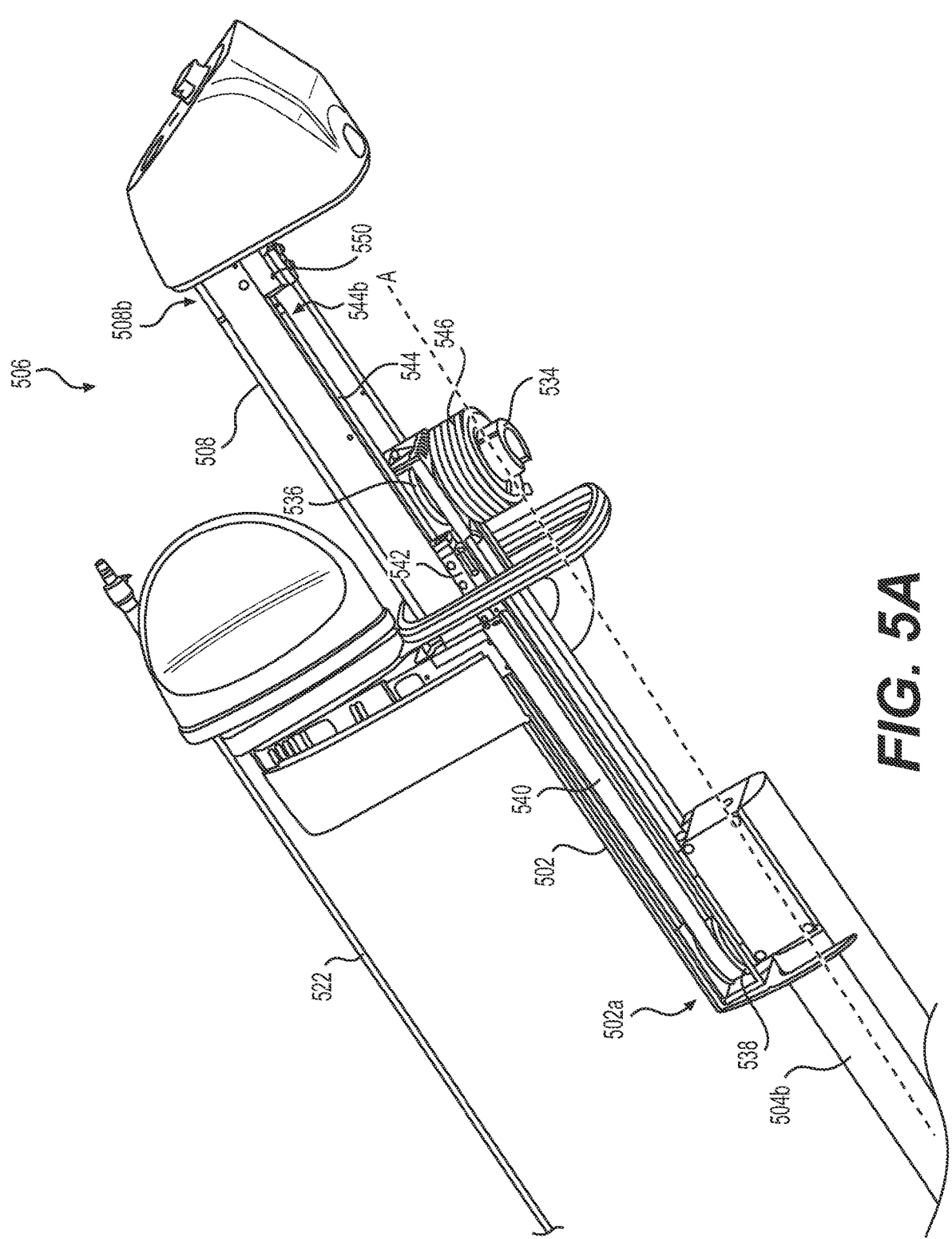
FIGS. 5A-5C illustrate various aspects of an instrument manipulator according to an embodiment of the present disclosure.
Figure 5B:
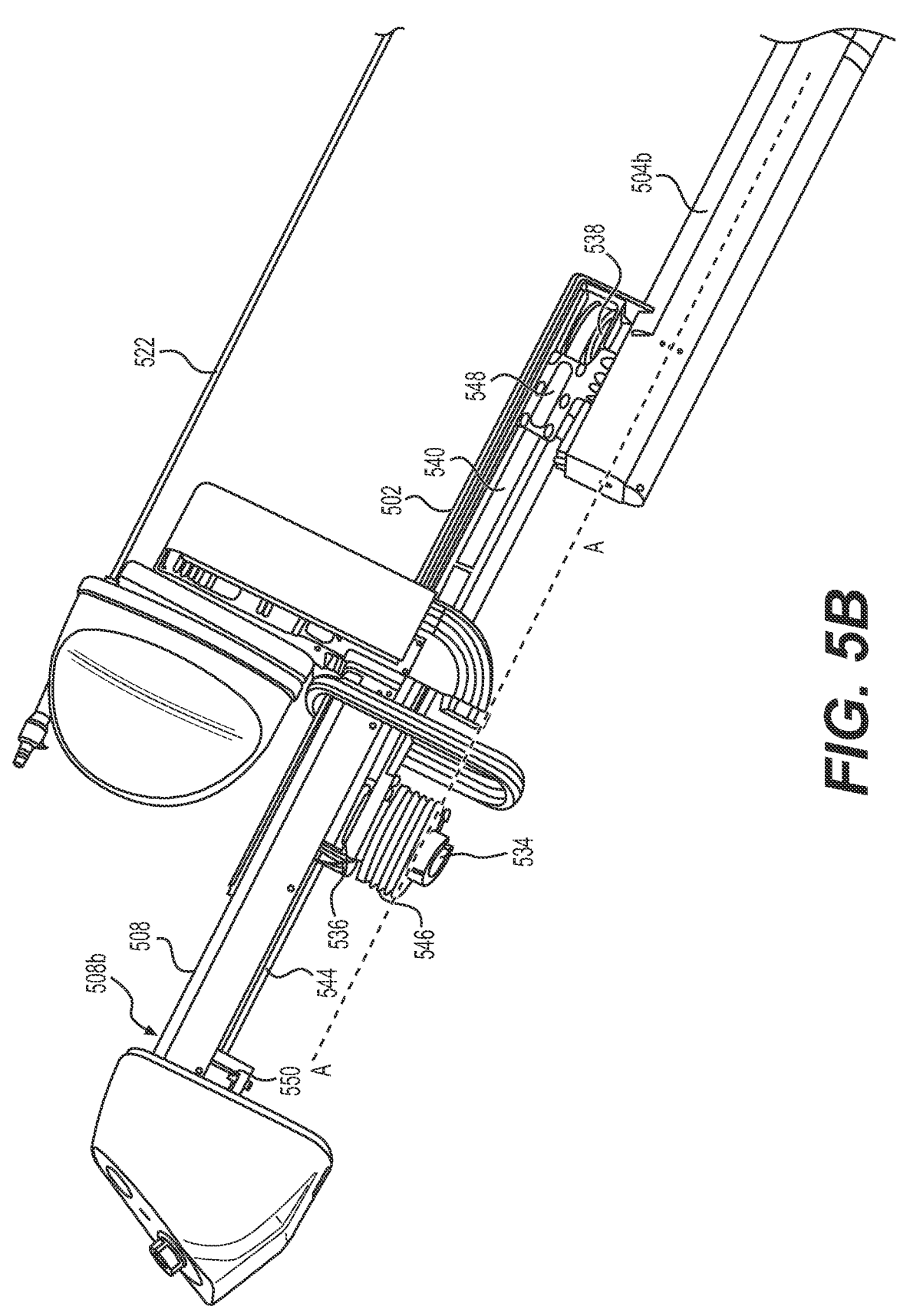
Figure 5C:
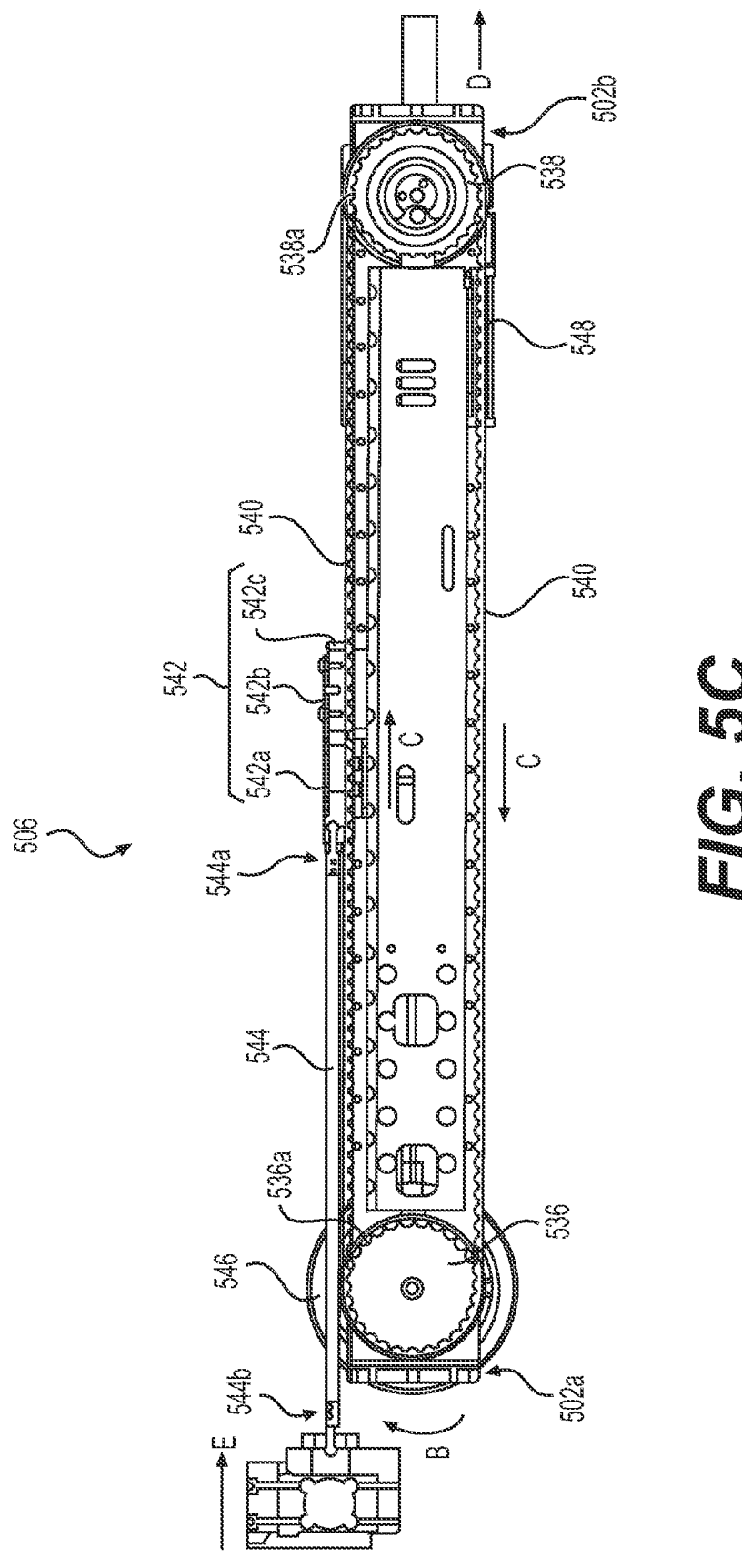

FIGS. 5A, 5B, and 5C illustrate an example of an instrument manipulator 506 according to an embodiment of the present disclosure. Instrument manipulator 506 may be substantially similar to instrument manipulator 206 of FIGS. 2 and 2A and instrument manipulator 306 of FIGS. 3A and 3B, with components hidden (e.g. housings, covers, cables, etc.) for clarity. FIG. 5A is a right isometric view of instrument manipulator 506, FIG. 5B is a left isometric view of the instrument manipulator 506, and FIG. 5C is a top view of the insertion stage 502 coupled to a distal end portion of the main portion 504*b* of the base 504, of the instrument manipulator 506.

As shown, the insertion stage 502 is slidably engaged with the instrument carriage 508 and aligned with the instrument carriage 508 along linear axis A, insert and retract directions. The insertion stage 502 is also slidably engaged with a main portion 504b of the base of the instrument manipulator 506. The insertion stage 502 and instrument carriage 508 are configured to move linearly in a telescoping manner with respect to main portion 504b of base 504. In some embodiments, the insertion stage 502 includes linear bearings that are slidably coupled to linear slide rail portions fixed to the instrument carriage 508, in order to facilitate efficient translational movement of the insertion stage 502 with respect to the instrument carriage 508 and to support the instrument carriage 508 and keep the insertion stage 502 and instrument carriage 508 aligned along the same linear axis A. Additionally, the insertion stage 502 may also include linear slide rail portions that are slidably coupled to linear bearings fixed to the main portion 504b of the base 504 in order to facilitate efficient translational movement of the insertion stage 502 with respect to the main portion 504b of the base 504.

The insertion stage 502 includes an insertion assembly which includes a drive belt 540, an idler pulley, and a drive motor 534 with a drive shaft (not shown) fixedly coupled to a drive pulley 536. The drive pulley 536 and idler pulley 538 are rotatably coupled by the drive belt 540 which wraps around the drive pulley 536 and idler pulley 538. As shown in FIG. 5C, the drive pulley 536 and idler pulley 538 each have teeth 536a, 538a proximate the respective outer circumferences in order to securely grasp toothed, corresponding portions of the drive belt 540. Drive motor 534 actuates drive pulley 536 in a first rotational direction or a second rotational direction, in order to drive the drive belt 540 in a first or second direction, respectively. The first direction may correspond to advancing an elongate device 522 (e.g., flexible catheter with steerable, bendable distal end portion) with respect to the patient anatomy, and the second direction may correspond to retracting the elongate device 522 with respect to the patient anatomy.

In one embodiment, as shown in detail in FIG. 5C, the drive belt 540 includes a non-continuous belt with two clamps 542a, 542b, each coupled to different ends of the non-continuous belt. The non-continuous belt can wrap around the drive pulley 536 and the idler pulley 538 and form a continuous loop by connecting clamp 542a to clamp 542b to form a clamp assembly 542. The clamp assembly 542 can include a tension bolt 542c that runs laterally through both clamps 542a, 542b and can be tightened or loosened in order to decrease or increase the separation of the clamps 542a, 542b to thereby maintain a desired tension on the drive belt 540.

Clamps 542a and 542b can be fixed to a proximal end portion 544a of a connecting element 544 that extends along the length of the instrument carriage 508 to couple at a distal end portion 544b of the connecting element 544 to the instrument carriage 508. Distal end portion 544b of connecting element 544 can be fixed to the instrument carriage 508 at any point along the length of the instrument carriage 508. In one embodiment, distal end portion 544b of connecting element 544 can be fixed near a distal portion 508b of the instrument carriage 508, as shown in FIG. 5A. Thus, as the drive belt 540 is actuated by rotation of the drive motor 534, the connecting element 544 travels with the drive belt 540 to translate the instrument carriage 508 in a linear insert or retract direction based on the direction of rotation of the drive motor 534. The connecting element 544 is movable with the drive belt 540 by a distance that is defined between the first end portion 502a of the insertion stage 502 and the second end portion 502b of the insertion stage 502.

The connecting element 544 has a predetermined length that may be selected according to the length of the instrument carriage 508 along the linear axis A and the distance by which the instrument carriage 508 is selected to travel with respect to the insertion stage 502. Accordingly, the distance by which the instrument carriage 508 is movable with respect to the insertion stage 502 may be defined by the length of the connecting element 544, as well as the distance by which the clamp assembly 542 coupled to the connecting element 544 is able to travel between the first end portion 502a and second end portion 502b of the insertion stage 502. The clamp assembly 542 is configured with respect to the insertion stage 502 such that the clamp assembly 542 (and/or coupled connecting element 544) does not travel around the drive pulley 536 or the idler 538 pulley. For example, the pulleys 536, 538 may be sized and shaped such that one or more of the clamps 542a, 542b only travel along the distance that is defined between the first end portion 502a of the insertion stage 502 and the second end portion 502b of the insertion stage 502 without traveling over either one of the pulleys 536, 538. Additionally, end portions 502a, 502b may be shaped or otherwise configured to block passage of one or more of the clamps 542a, 542b. In other embodiments, hardstops may be placed at any location of the insertion stage 502 along the path of the drive belt 540 to prevent further travel of the clamp assembly 542 (and/or coupled connecting element 544).

The clamp assembly 542 and connecting element 544 are linearly aligned along linear axis A with the drive belt 540 and the respective orientations of the instrument carriage 508 and main portion 504b of the base 504. In some embodiments, for example as can be seen in FIG. 5A, the connecting element 544 may be disposed such that it runs along the length of the instrument carriage 508 on one side and is coupled to a distal end portion 508b of the instrument carriage 508 in order for the connecting element 544 and clamp assembly 542 to be displaced from an area where insertion stage 502 components such as the drive motor 534, cable pulley 546 and/or other components or portions of the insertion stage 502 may extend into the internal space of the instrument carriage 508 defined by the instrument carriage 508 housing.

The instrument carriage 508 is coupled to the insertion stage 502 by the connecting element 544, rather than, for example, by directly connecting the instrument carriage 508 to the drive belt 540 or clamp assembly 542, which allows the instrument carriage 508 to move with respect to the insertion stage 502 without the need for slots or other openings to be defined in the insertion stage 502 housing. Slots or other such openings may disadvantageously allow for the insertion stage 502 or instrument carriage 508 to be more susceptible to leakage of fluids or contamination. Frequently, medical drapes are used to cover such types of openings in order to reduce likelihood of leakage or contamination. Drapes must be frequently cleaned or regularly replaced and many do not provide for adequate scaling. Thus, one advantage provided by the design of these embodiments of the present disclosure is that it aids in maintaining a cleanable and disinfectable procedure environment and allows for easier cleaning of the instrument manipulator 506 components.

Referring to FIGS. 5B and 5C, a mounting plate 548 is shown fixed to the main portion 504b of base 504. The mounting plate 548 is also fixed to the drive belt 540. Thus, as the drive belt 540 is actuated by the drive motor 534 rotation, a portion of the drive belt 540 is fixed to the mounting plate 548, which is fixed to the base 504, causing the insertion stage 502 to translate along the main portion 504*b*. The distance (e.g., amount of linear travel) by which the insertion stage 502 can move along axis A, is defined by the distance the drive belt 540 can move with respect to the fixed mounting plate 548. The particular mounting location and fixation of the mounting plate 548 to the main portion 504*b* of the base 504 prevents the mounting plate 548 from travelling around the drive pulley 536 or the idler pulley 538.

FIG. 5C illustrates an example of telescoping linear motion of the instrument carriage 508 and the insertion stage 502, in one embodiment. Rotation B of the drive motor 534 actuates translation C of the drive belt 540 (or rotation of the drive belt 540 around idler pulley 538). However, since the drive belt 540 is fixed to the base 504 by the mounting plate 548, rotation of the drive belt 540 forces the insertion stage 502 to translate D. As illustrated in FIG. 5A, the clamp assembly 542 is fixed to both the instrument carriage 508 and the drive belt 540. Thus, as the drive belt 540 rotates C, the clamp assembly 542 translates with the drive belt 540 C, and the instrument carriage 508 is forced to linearly translate E. Thus, among other advantages and benefits provided by the particular component configuration that interrelates the instrument carriage 508, insertion stage 502, and base 504, only a single drive motor and a single drive belt are needed to control movement of both the instrument carriage 508 and the insertion stage 502. Extraneous drive motors or other forms of actuation are therefore not required. An additional advantage is that the length of the linear translation E of the instrument carriage 508 may be twice as long as the length of the linear translation D of the insertion stage 502. Further, the linear translation E of the instrument carriage 508 may occur twice as fast as the linear translation D of the insertion stage 502. Another advantage is that the amount of space required to stow the instrument carriage 508 and the insertion stage 502 is reduced due to the telescoping motion of the instrument carriage 508 and the insertion stage 502.

Referring back to FIG. 5B, a force sensor 550 mounted to the instrument carriage 508 can be provided to couple to the connecting element 544. Thus, the force sensor 550 can be configured to measure insertion force experienced by the elongate device 522 as the elongate device 522 is inserted within the patient anatomy. The force sensor 550 can be a strain gauge, piezoelectric sensor, pressure sensor, and/or any other load sensor.

A cable pulley 546 of the insertion stage 502 may be configured to receive and route multiple operational cables (not shown) such as power cables, communication cables, and/or fiber optic cables. The cable pulley 546 may be configured with separate channels or grooves to physically separate the cables at the insertion stage 502 to prevent entanglement. The cable routing is designed such that the cables emerge from the base 504*b*, route around the cable pulley 546 on the insertion stage 502, and terminate in the instrument carriage 508. This is advantageous because the relative motion of these three geometric points in the assembly permit for the length of the cables to be conserved. Therefore, the cables are unlikely to de-rail and become damaged. Sufficient tension should be maintained on all the cables in order to prevent them from collecting together or unraveling, while also preventing over-tensioning on the cables and allowing each cable to rotate freely from the other. In some embodiments, the cable pulley 546 may include roller bearings to assist in tension regulation. In further embodiments, the cable pulley assembly may include multiple independent pulleys, each with one groove. In such embodiments, the multiple independent pulleys are assembled concentrically on a low friction central hub to allow for each cable to move relative to each other cable. This reduces the requirement for equal tension on each cable.

In some embodiments, cable connections between the instrument carriage 508 and the insertion stage 502 may route along the insertion stage 502 itself and be captured and hidden. Cables including fiber can be routed around the cable pulley 546 and then into the instrument carriage 508. Turns with a tight bend or radius may cause breakage of fiber, so this selective routing can prevent fiber pinch or a tight bend.

FIGS. 6A-6J illustrate an example of visual representations providing guidance to a user such as an operator or another individual setting up a medical system (also referred to as "set-up") in accordance with some embodiments of the present disclosure. FIGS. 7A-7H illustrate an example of visual representations providing guidance to a user for taking down the medical system (also referred to as "tear down") in accordance with some embodiments of the present disclosure.

The visual representations may be graphically displayed by implementing aspects of the display system 110 of FIG. 1, for example, which may include displaying the visual representations on a display monitor (e.g., display monitor 216*a* and/or 216*b* of FIG. 2), a display on a master console (e.g. master control 220), and/or computer display, accessible to and viewable by the user as he/she sets up or takes down the medical system. The visual representations shown in each of FIGS. 6A-6J and FIGS. 7A-7H generally have a common layout. The general step to be performed according to the textual guidance provided, e.g., to complete a corresponding part of the set-up or tear down process, is displayed in one section (left side window, as shown) of the visual representation (e.g., "Perform System Tests", FIG. 6A), which includes a list of steps that are to be performed.

The visual representation of each of FIGS. 6A-6J and FIGS. 7A-7H show in another section (right side window, as shown), a diagram of the medical system or select relevant components of the medical system, and may show certain elements of the system that are actively involved in the relevant step in a visually emphasized manner over other elements in the diagram. For example, in the visual representation of FIG. 6D, elements associated with a vision probe are visually emphasized in the diagram in contrast to other depicted surrounding elements, as the current step to be performed is to attach a vision probe (see "Attach Vision Probe").

In some embodiments, coordination of the visual representations for guiding a user through the set-up and/or tear down processes may be implemented using hardware, firmware, software, or a combination thereof which interact with or are otherwise executed by one or more computer processors, which may include the processors of a control system such as a control system 112 in FIG. 1. The control system may include at least one memory and at least one computer processor for executing programmed instructions, and may be coupled to a display system such as display system 110, as shown and described with respect to FIG. 1. A sensor system such as sensor system 108 may be implemented to sense and/or otherwise provide feedback or other information corresponding to the state of systems and/or relevant components for various steps of the guided process(es), such that, for instance, it may be automatically determined that a component has been attached or detached, respectively. A control system and/or sensors as described above may, in some embodiments, be implemented in controlling and/or coordinating automated system checks and initialization steps. In the following description of the guided set-up of FIGS. 6A-6J and guided tear down of FIGS. 7A-7H, numbered elements in FIGS. 6A-6J and FIGS. 7A-7H may be referred to with respect to examples of other similar elements in other Figures.

Figure 6A:
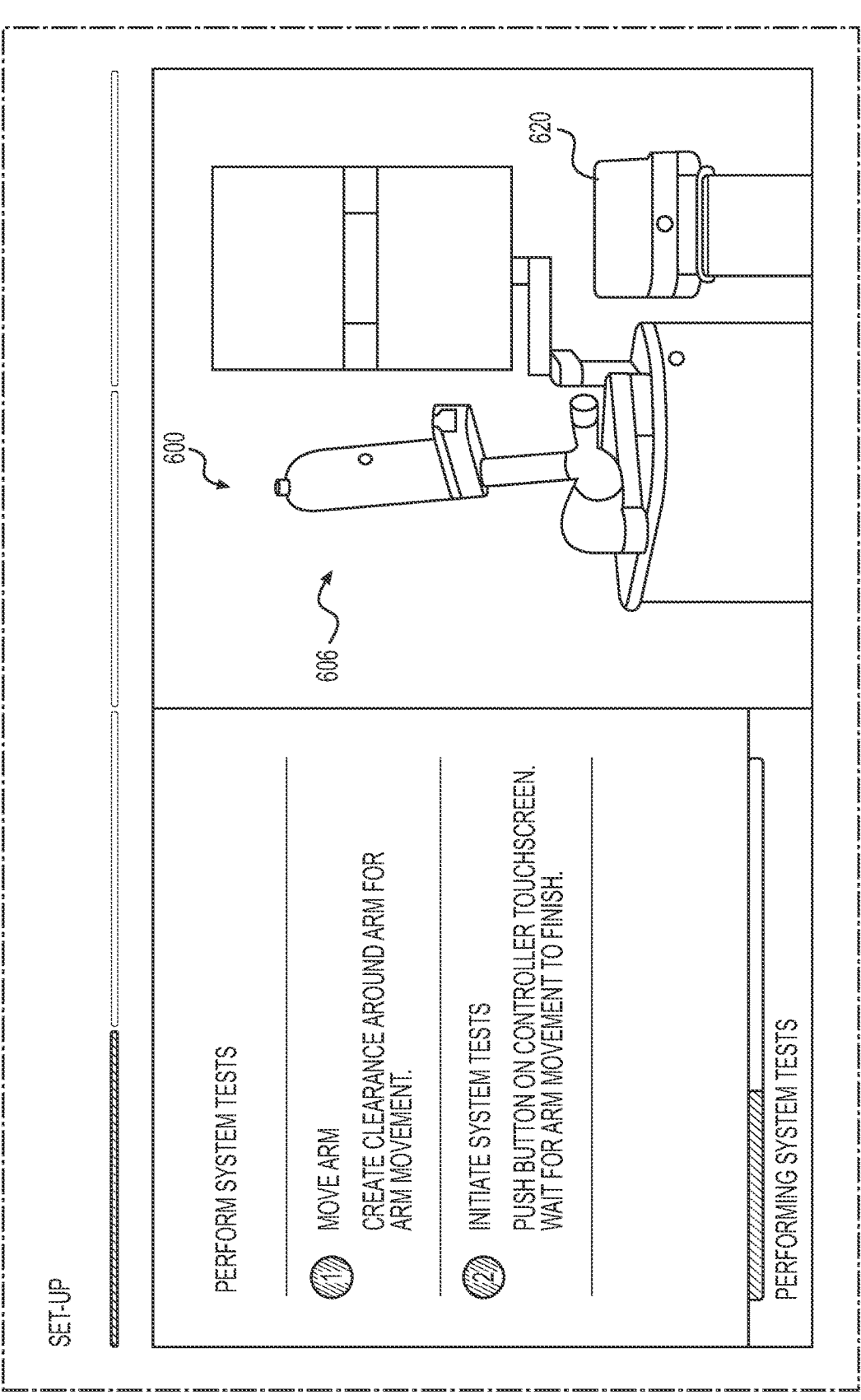
FIGS. 6A-6J illustrate an example of visual representations providing guidance for setting up a medical system in accordance with some embodiments of the present disclosure.

Now specifically referring to FIGS. 6A-6J, these visual representations provide step-by-step guidance to a user such as an operator or another individual for setting up a medical system in accordance with some embodiments of the present disclosure. FIG. 6A visually represents guidance for performing initial system tests for a medical system 600, which includes some of the same or similar components to those shown in the embodiments of FIGS. 2, 2A, 2B, 3A, and 3B. As shown in FIG. 6A, for initial automated system tests ("Perform System Tests"), for example to ensure that elements of the medical system 600 are in proper operational order before the system 600 is to be used in a procedure such as a medical procedure on a patient, first the arm 606 (e.g., manipulator assembly 202, FIG. 2) should be positioned such that clearance is created around the arm 606 for arm movement. Next, to initiate system tests, a button can be pushed on a touchscreen of a controller 620, for example a control console such as master control 220 shown and described with respect to FIG. 2. As the next step indicated in FIG. 6A, the user waits for the arm movement to finish (e.g., finish automated initialization and checking for proper operating condition).

Figure 6B:
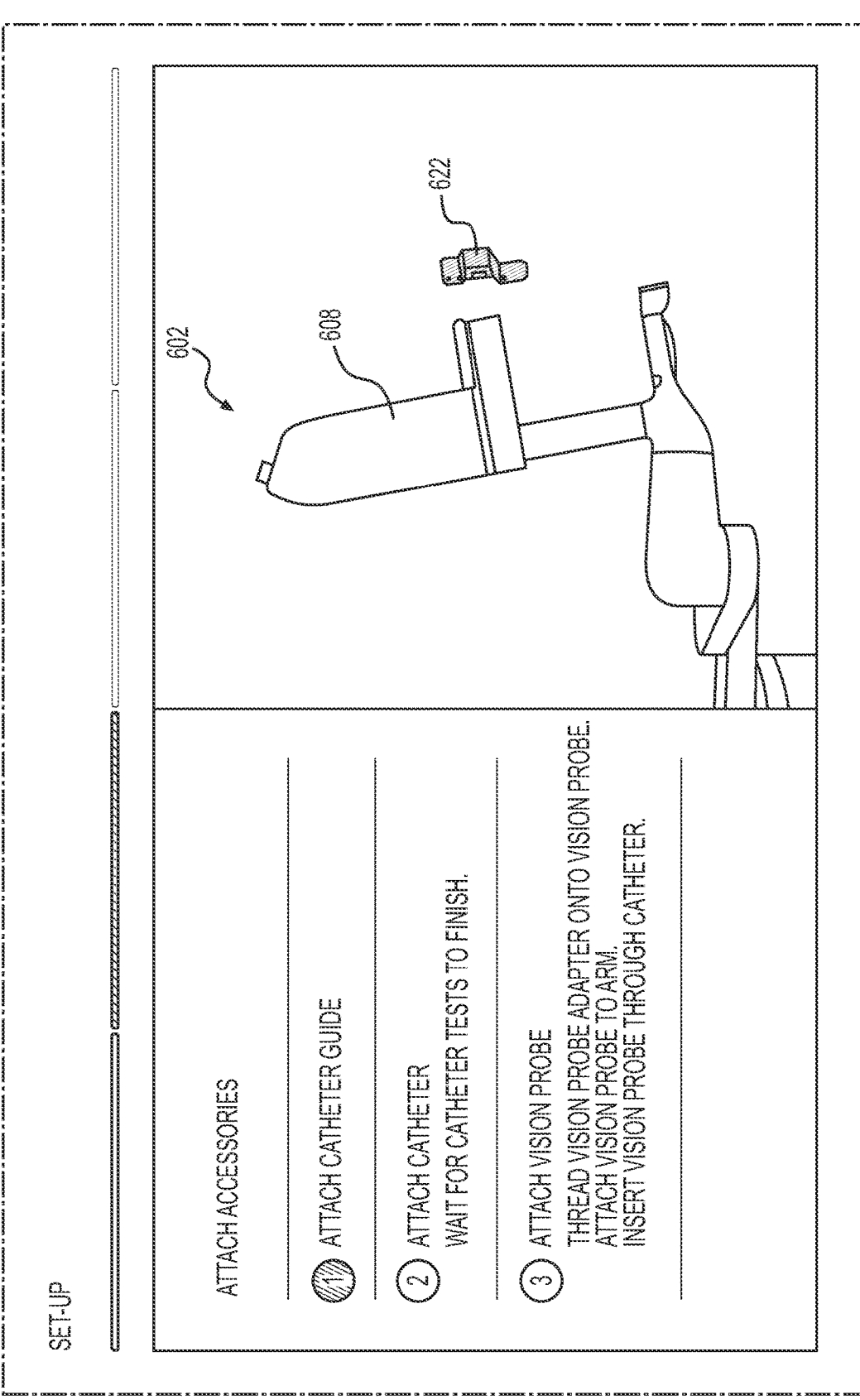
Figure 6C:
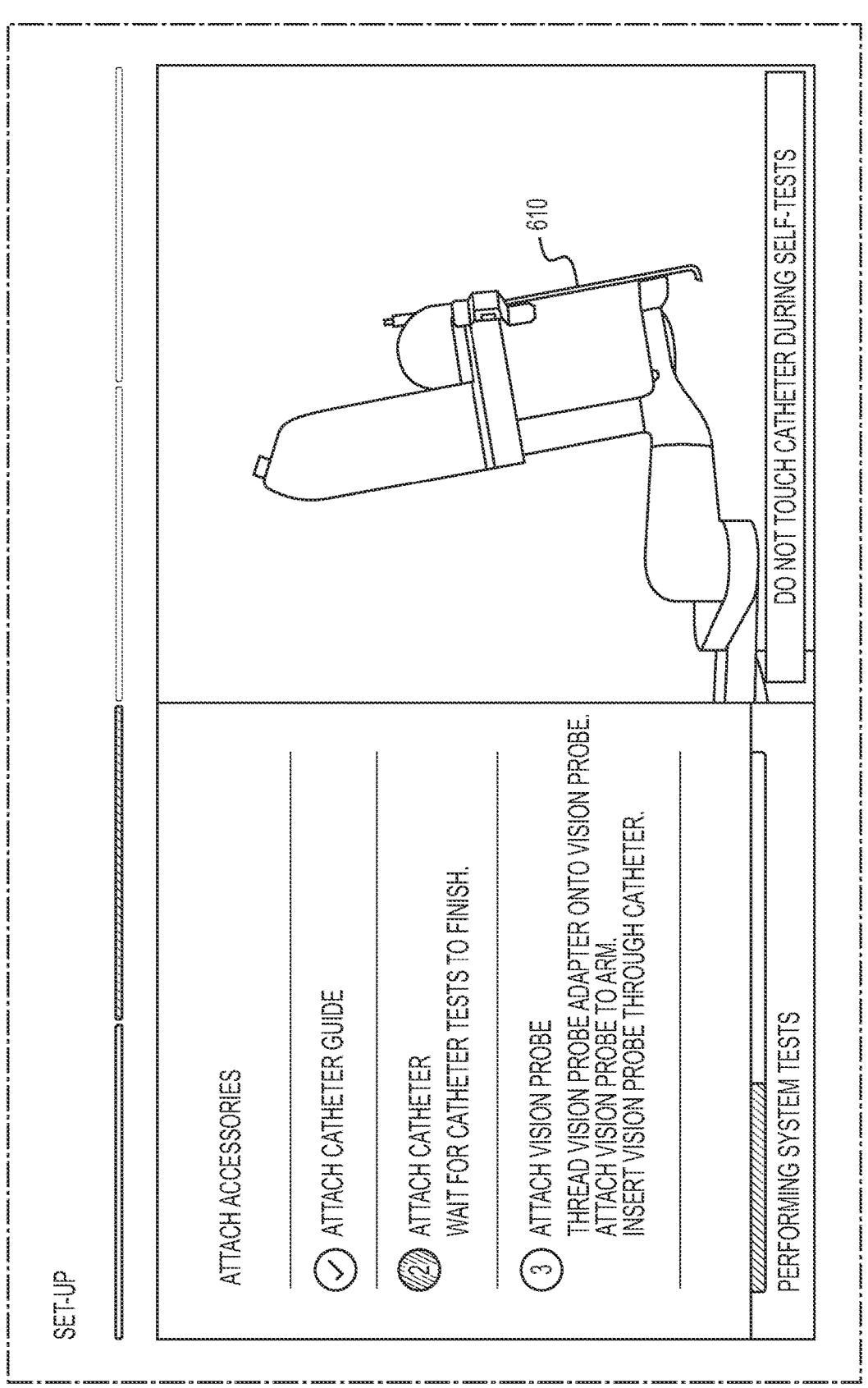
Figure 6D:
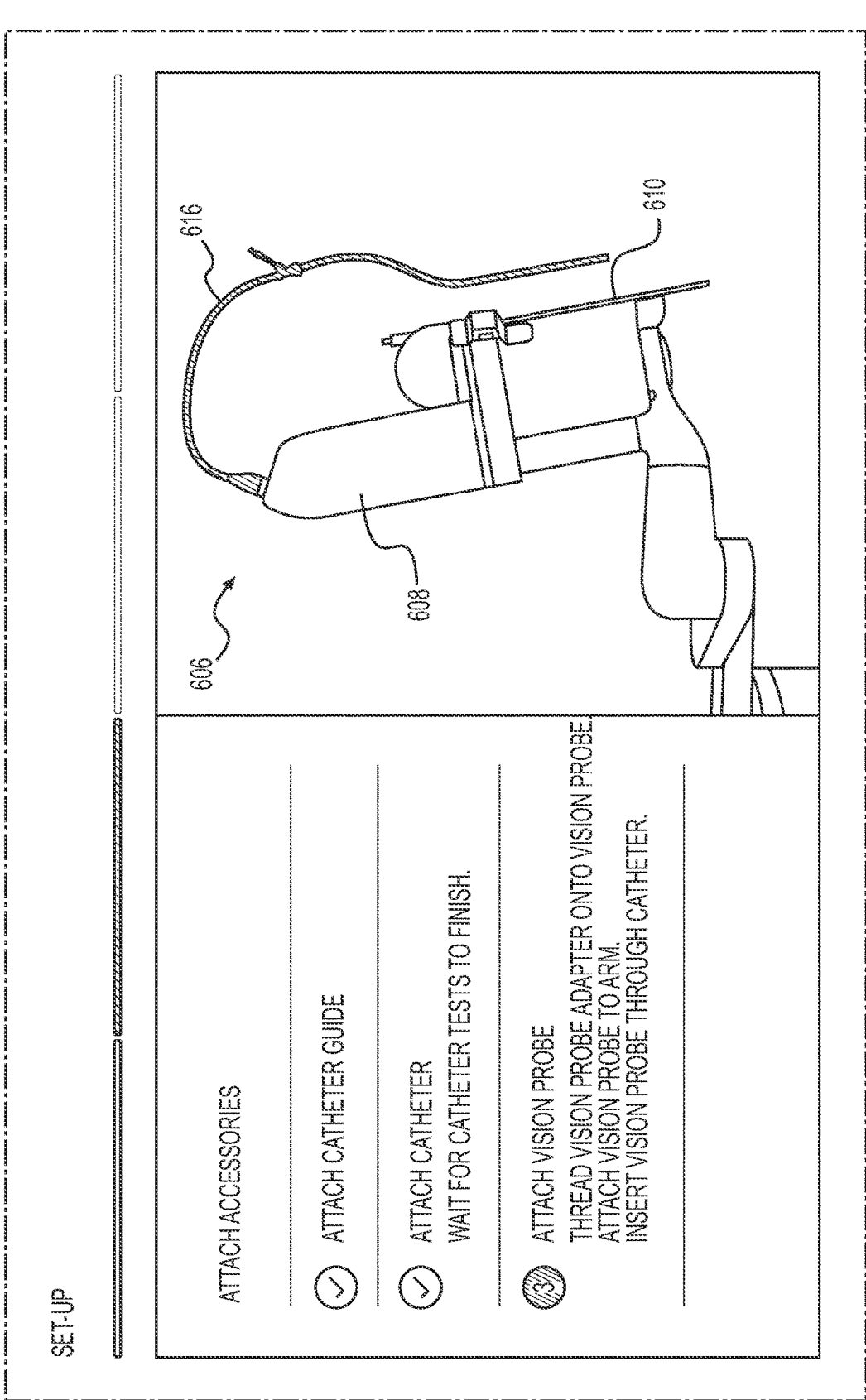
Figure 6E:
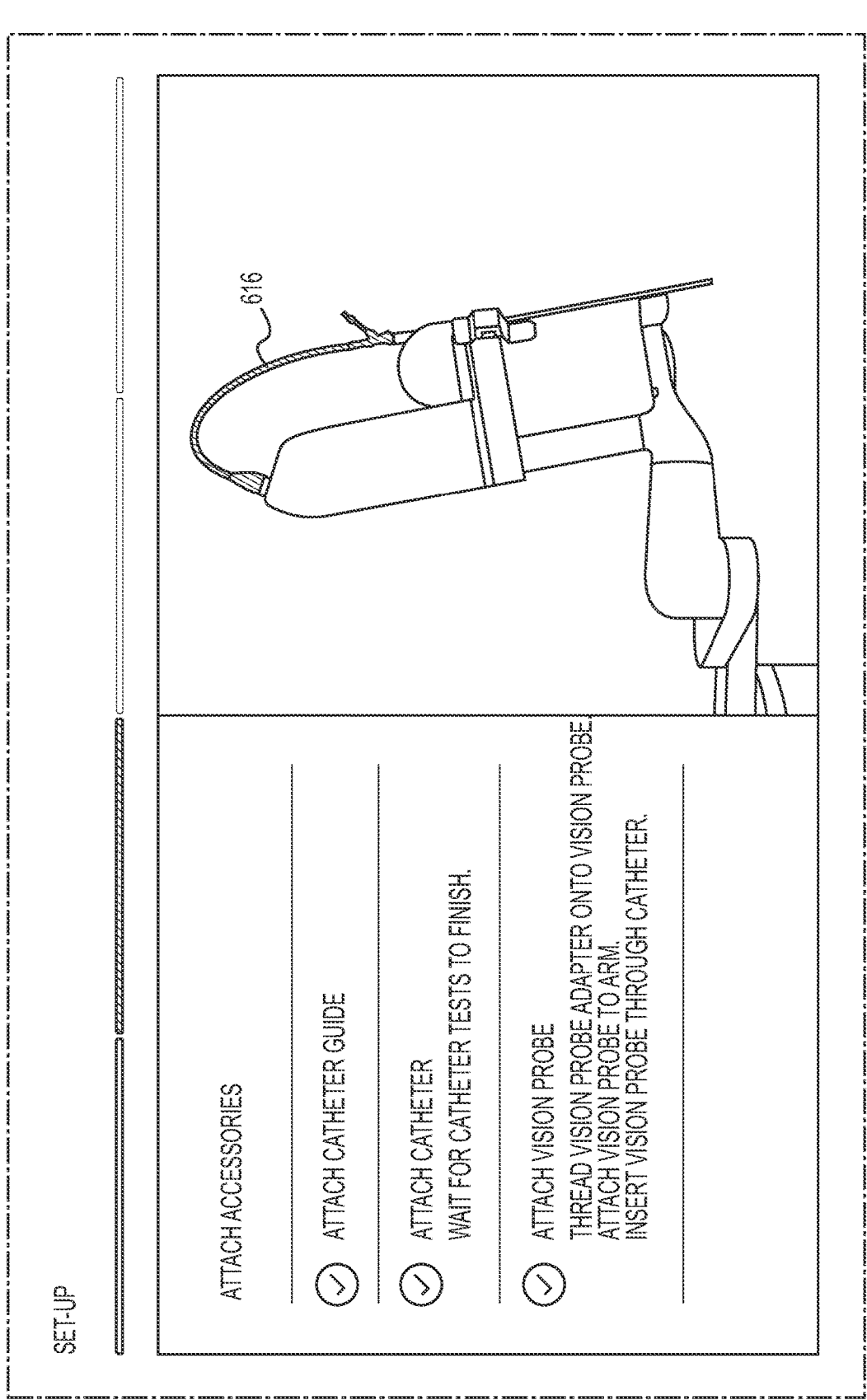

The next guided step for set-up, as shown in FIG. 6B, is attaching accessories ("Attach Accessories"). First, a catheter guide 622 in a retracted state, is attached to a carriage 608 (e.g., catheter guide 322 in FIG. 3A connected to carriage 308). After the catheter guide 622 has been attached, as indicated in FIG. 6C, a catheter 610 is attached (e.g., elongate device assembly 310 in FIG. 3A and attachment discussion in corresponding description). Once the catheter 610 is attached, automated self-tests of the catheter 610 are performed, for example to test articulation operations of the distal end portions and/or distal tip of the catheter). Next, as shown in FIG. 6D, a vision probe 616 is attached (e.g., probe assembly 316, FIG. 3A) which includes threading a vision probe adapter onto the vision probe (see, e.g., probe assembly 316 in FIG. 3A), attaching the vision probe 616 to the arm 606 (see attachment at proximal end of carriage 608 of arm 606), and inserting the vision probe 616 through the catheter 610. An example of a vision probe, attachment, and a vision probe through a catheter is described with reference to the embodiment of FIG. 3A (wherein a probe 316b of a probe assembly 316 may be inserted into a working lumen of elongate device 310a through a connector 316a and may run through the elongate device 310a). After the step of attaching the vision probe 616 as indicated in the visual representation of FIG. 6D, then as indicated in FIG. 6E, each of the steps for attaching accessories ("Attach Accessories") have been completed. Encircled check-marks to the left of each completed, listed step are visually indicated. Also, as shown, the attached vision probe 616 is visually emphasized.

Figure 6F:
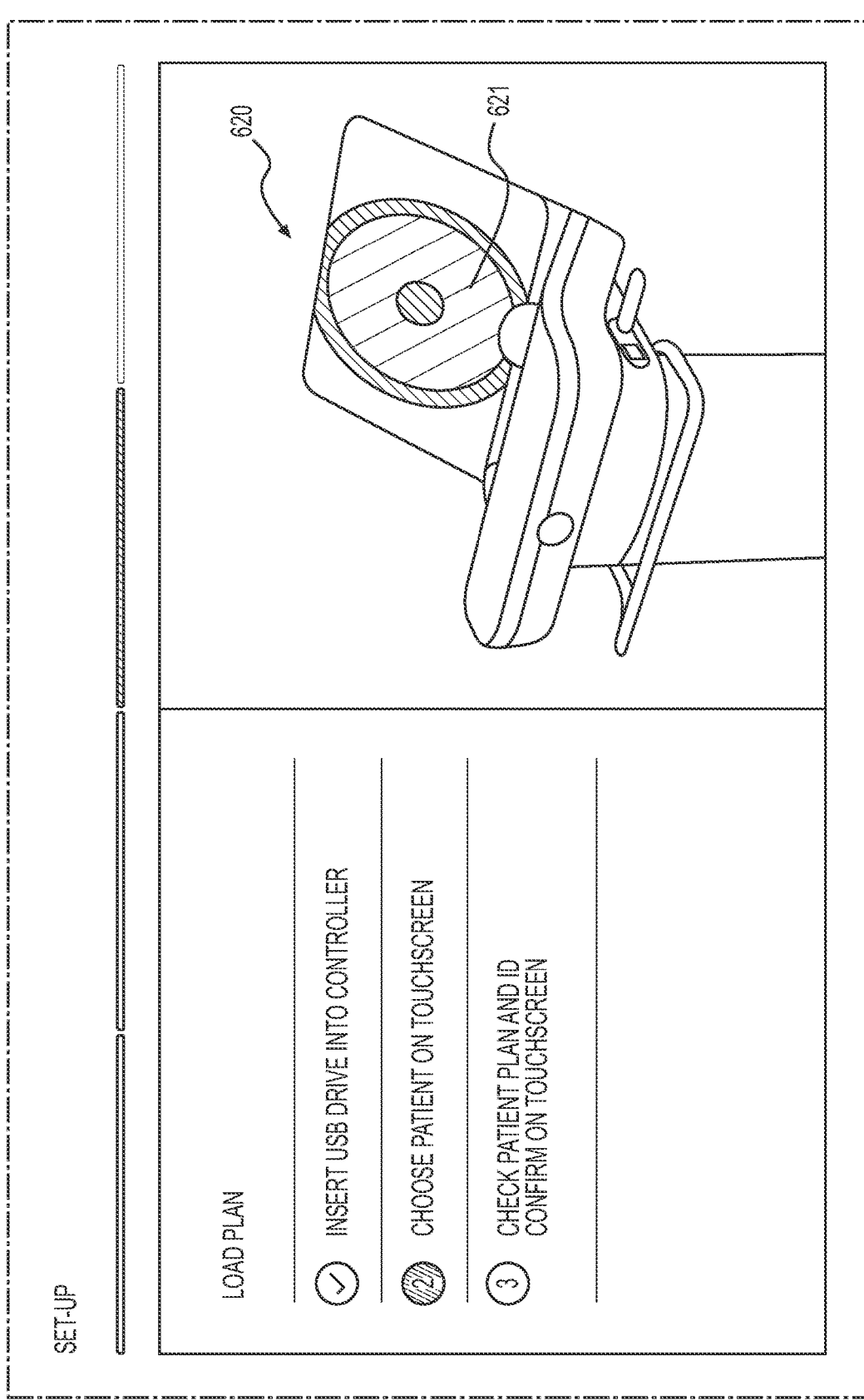

FIG. 6F is a visual representation providing guidance for loading a patient plan into a controller 620 (e.g., master control 220, FIG. 2). As shown, loading the patient plan ("Load Plan") includes the step of inserting a USB drive into the controller 620. This step may include providing the controller 620 with a non-transitory data storage device or other memory device storing patient-specific data for one or more patients, that may include particular health-related for specific patient(s) and/or may include information on what procedure(s) are to be performed on the specific patient(s), pre-operative images of patient anatomy, rendered images of patient anatomy, a planned path to an anatomical target, details of instruments, settings, and/or other information pertaining to particular operation of the medical system for performing the procedure(s), for example. The step of "Load Plan" that is current in FIG. 6F is for a user of the controller 620 to choose a patient from multiple patient representations shown on the touchscreen 621, by interacting with the touchscreen 621 (e.g., pressing on the touchscreen 621 at a particular location) to select the patient.

Figure 6G:
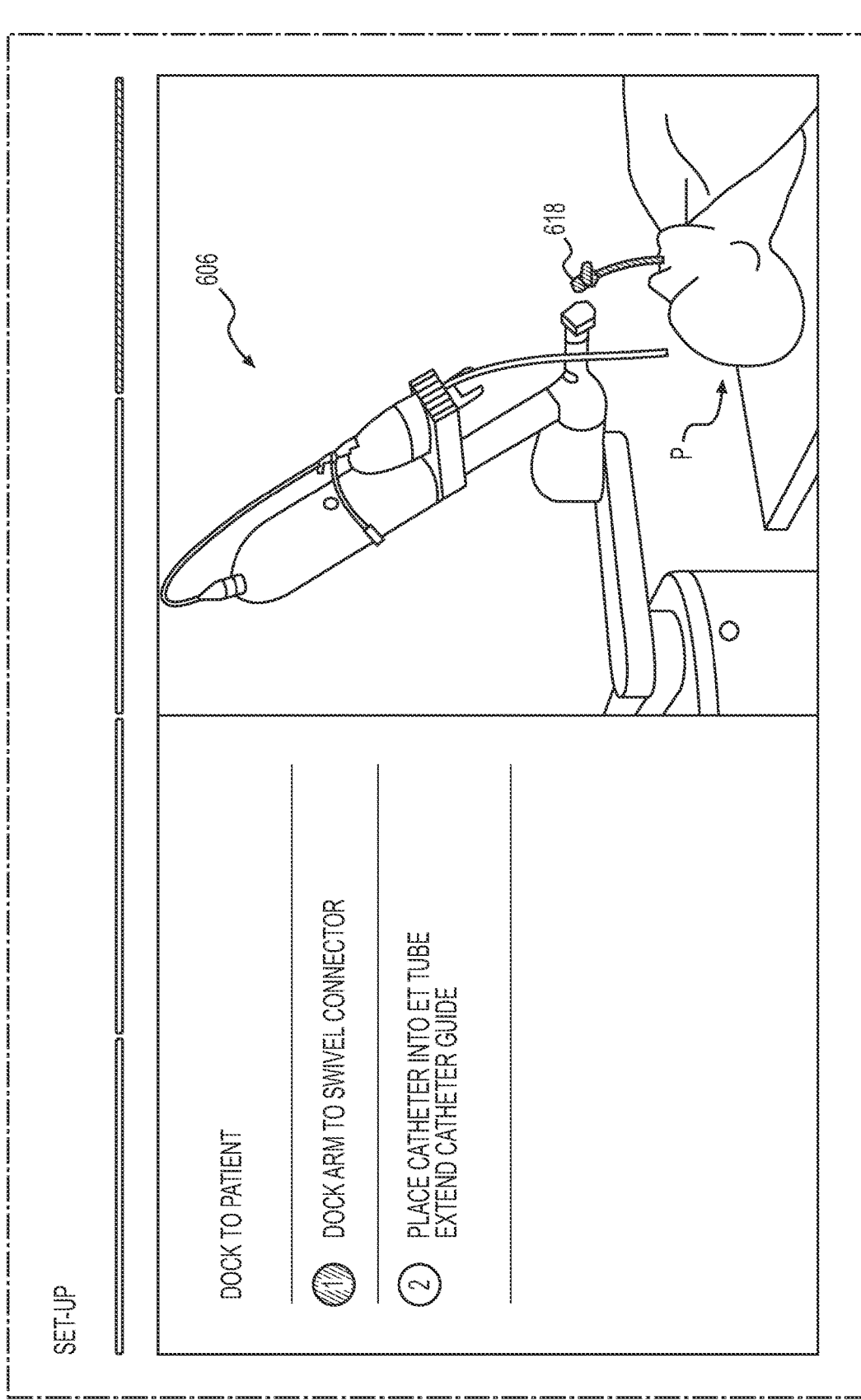
Figure 6H:
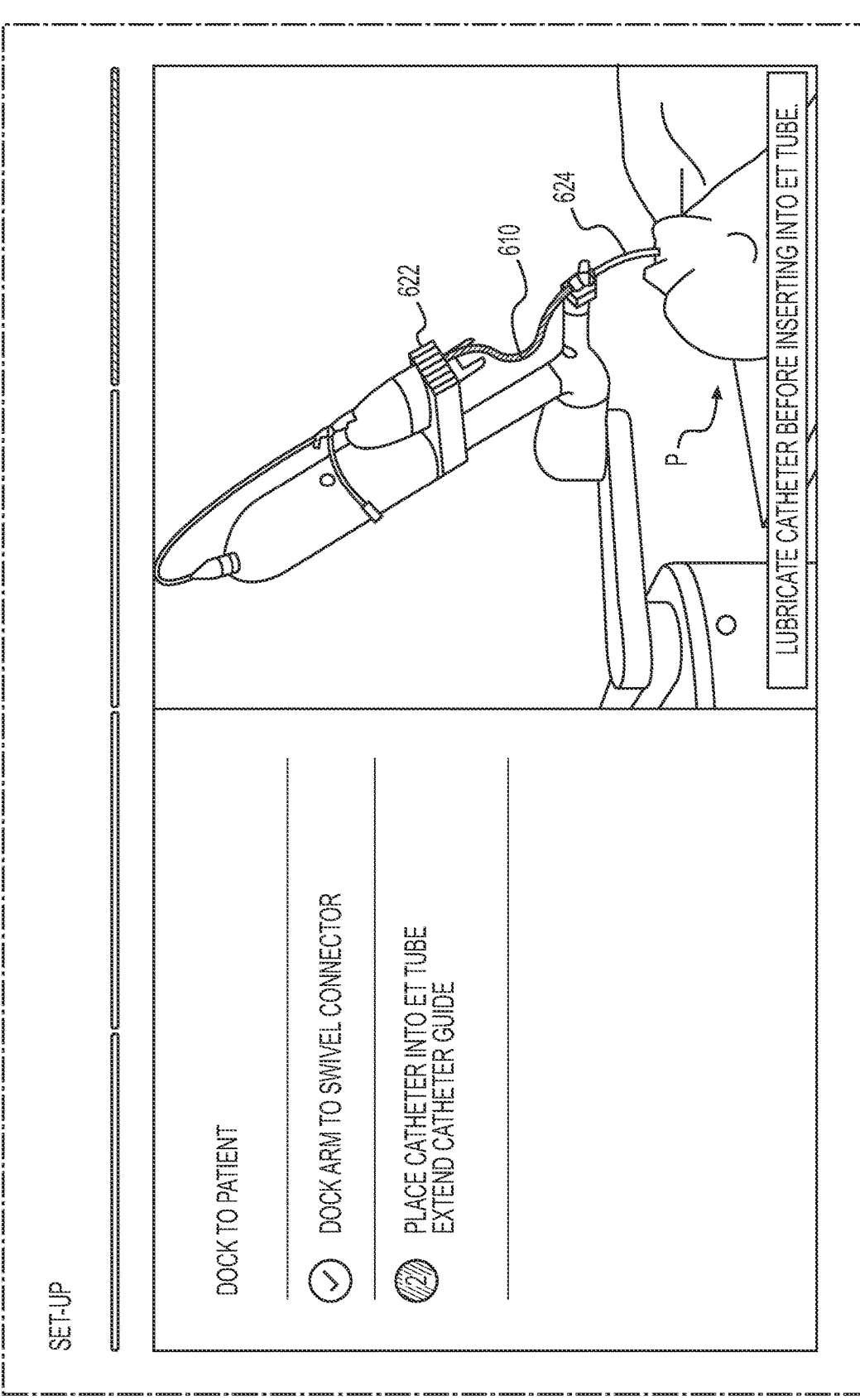
Figure 6I:
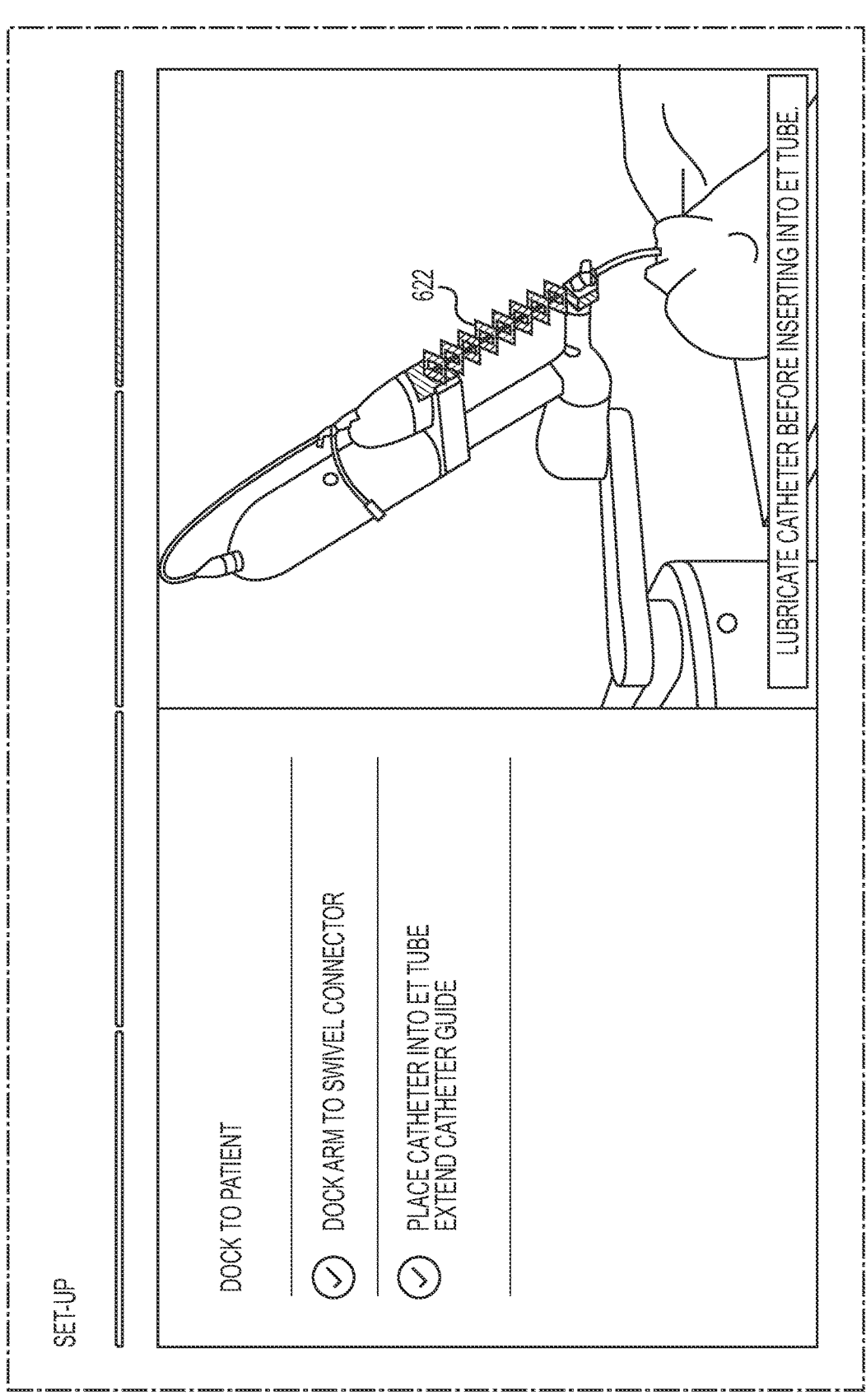
Figure 6J:
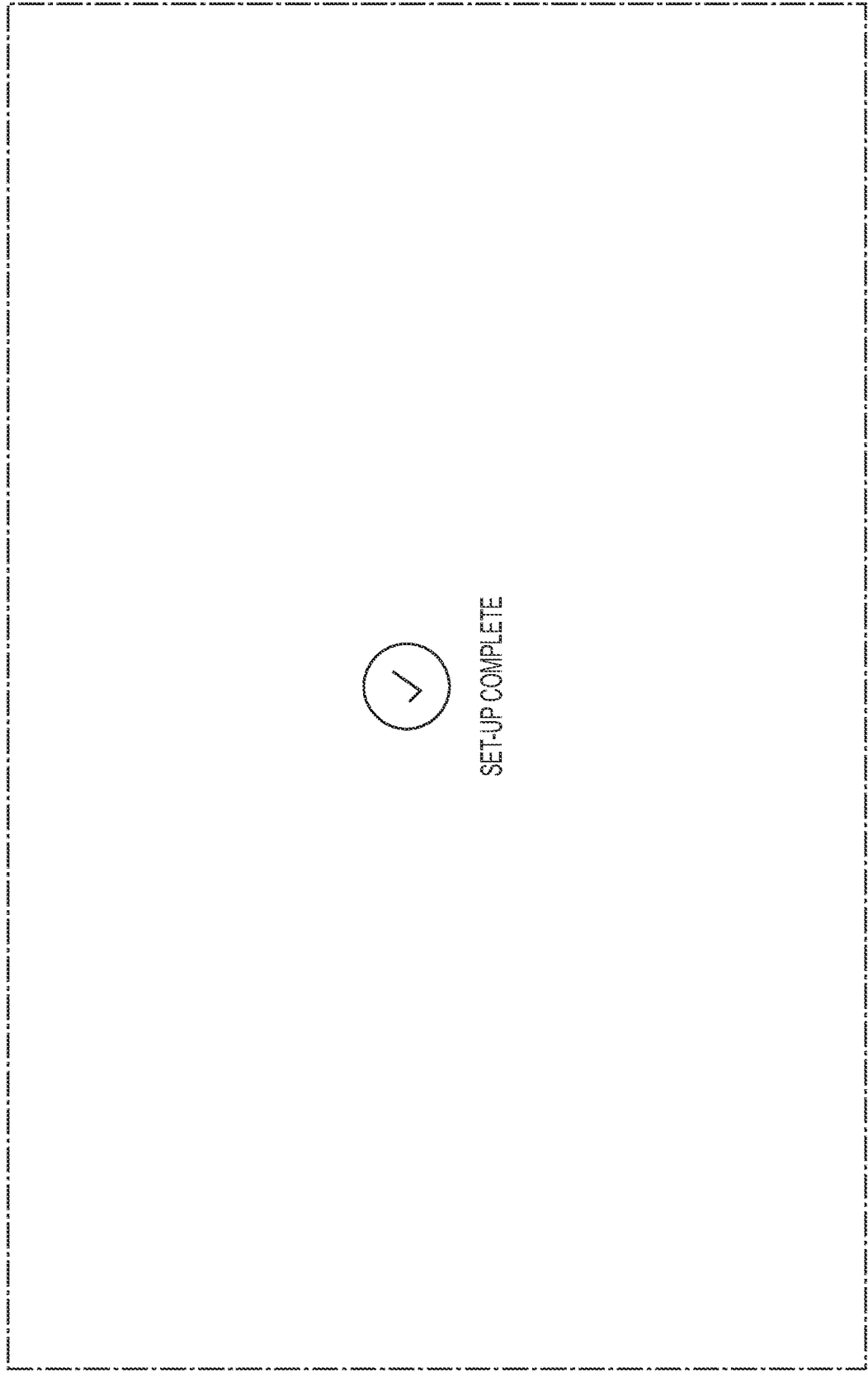

The next guided step for set-up, as shown in FIG. 6G, is docking the arm 606 to a medical device such as an endotracheal tube (ETT) which is coupled to a patient P ("Dock to Patient"). As shown in the visual representations of FIG. 6G, the first step is to dock the arm 606 to a device connector 618 (see e.g., distal end portion 304c of base 304 coupled to device connector 318, as shown and described with respect to FIGS. 3A and 3B). As shown in FIG. 6H, the next step of "Dock to Patient" is to place the catheter 610 into the endotracheal tube 624. As shown, a portion of the catheter 610 is visually emphasized in the diagram on the right side. An example of placing a catheter into an endotracheal tube is described with reference to FIG. 3A, discussing a device connector 318 and a patient medical device 320 such as an endotracheal tube with an elongate device 310a such as a catheter inserted into and running within the patient medical device 320. The endotracheal tube 624 is shown as inserted into the mouth of the patient P. The next step listed in the visual representation of FIG. 6H, immediately under "Place Catheter into ET tube" is to extend the catheter guide 622. An example of an extended catheter guide is shown by and described with reference to FIG. 3A, wherein an elongate device 310a such as a catheter runs through an extended "elongate device guide" 322. The catheter guide 322 extended into proper position is shown in detail in the visual representation of FIG. 6I. With the step of extending the catheter guide completed, then the "Dock to Patient" step of guided set-up is complete, and, as indicated by the check-marks next to the listed items (see listed items on left side), the set-up of the medical system is complete, which is visually indicated by the check-mark and "SET-UP COMPLETE" message in the visual representation of FIG. 6J.

FIGS. 7A-7H illustrate visual representations providing step-by-step guidance to a user such as an operator or other individual taking down a medical system after completion of a medical procedure, in accordance with some embodiments of the present disclosure. The medical system being taken down in accordance with the steps illustrated by FIGS. 7A-7H corresponds to the medical system 600 that was set up in accordance with the steps illustrated by FIGS. 6A-6J, and reference numbers in FIGS. 7A-7H that are the same as reference numbers in FIGS. 6A-6J refer to the same corresponding element(s). Alternatively, one or more of the steps illustrated by FIGS. 7A-7H may be applied to like components of a similar medical system without departing from the scope of the present disclosure.

Figure 7A:
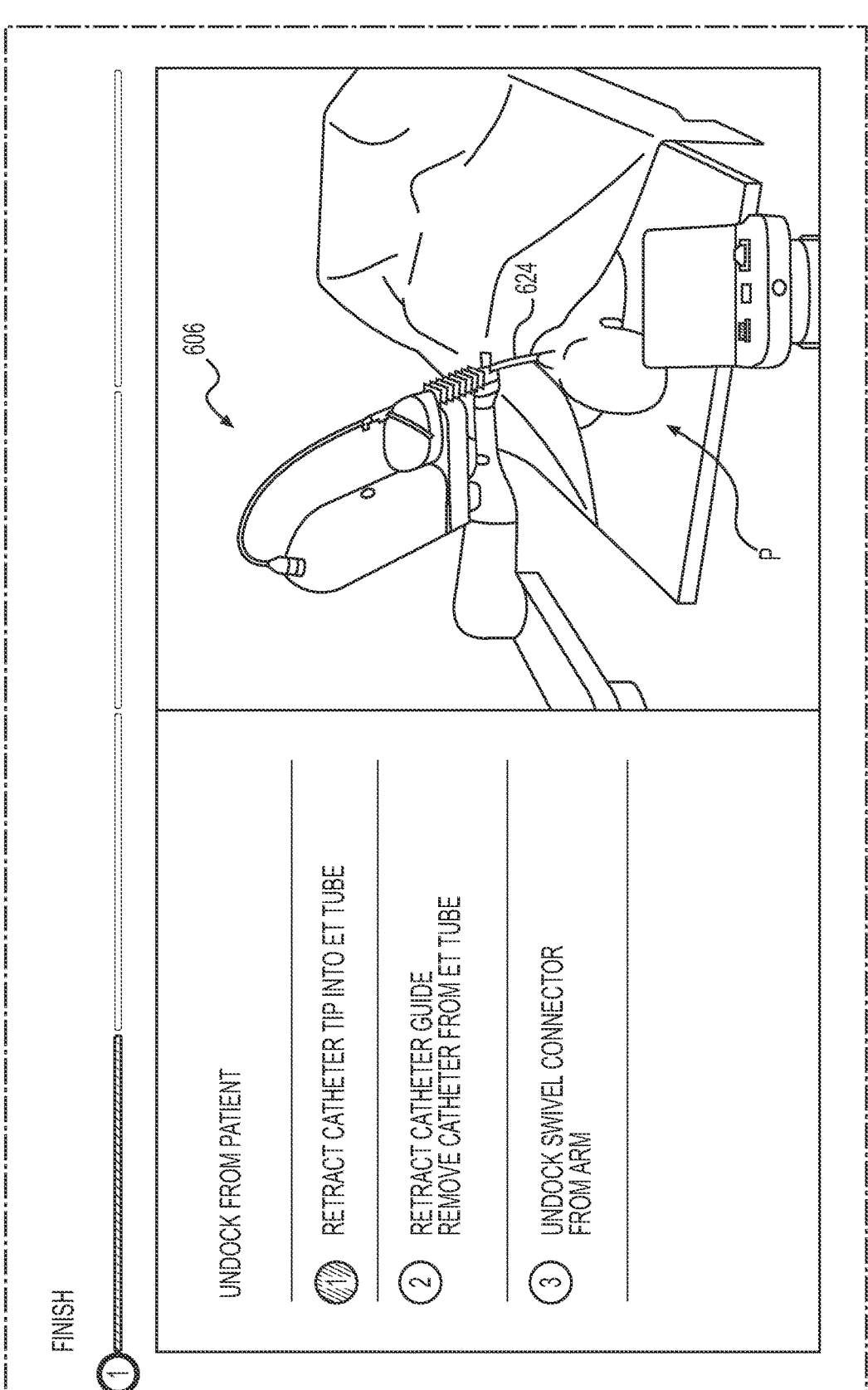
FIGS. 7A-7H illustrate an example of visual representations providing guidance for taking down a medical system in accordance with some embodiments of the present disclosure.
Figure 7B:
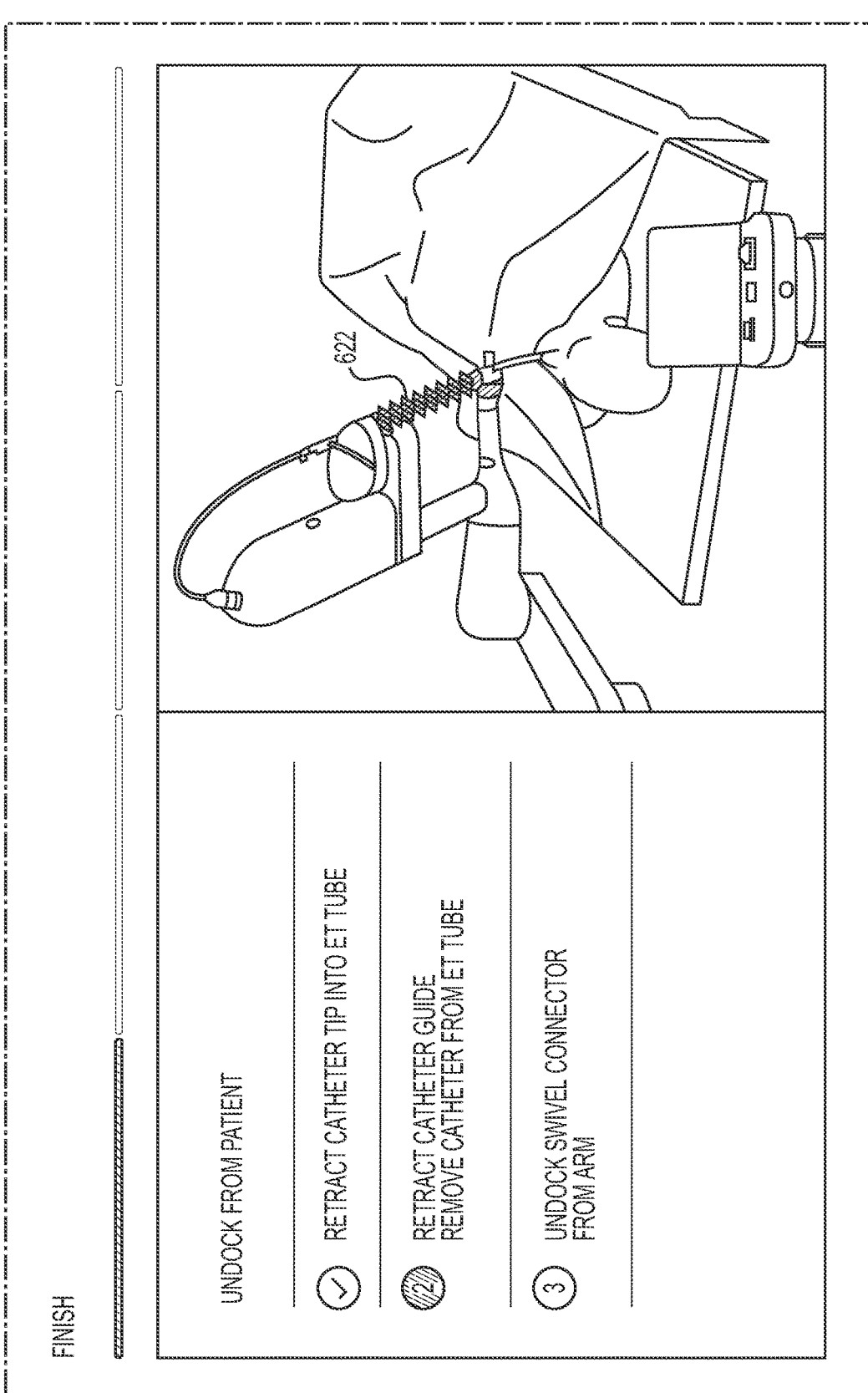
Figure 7C:
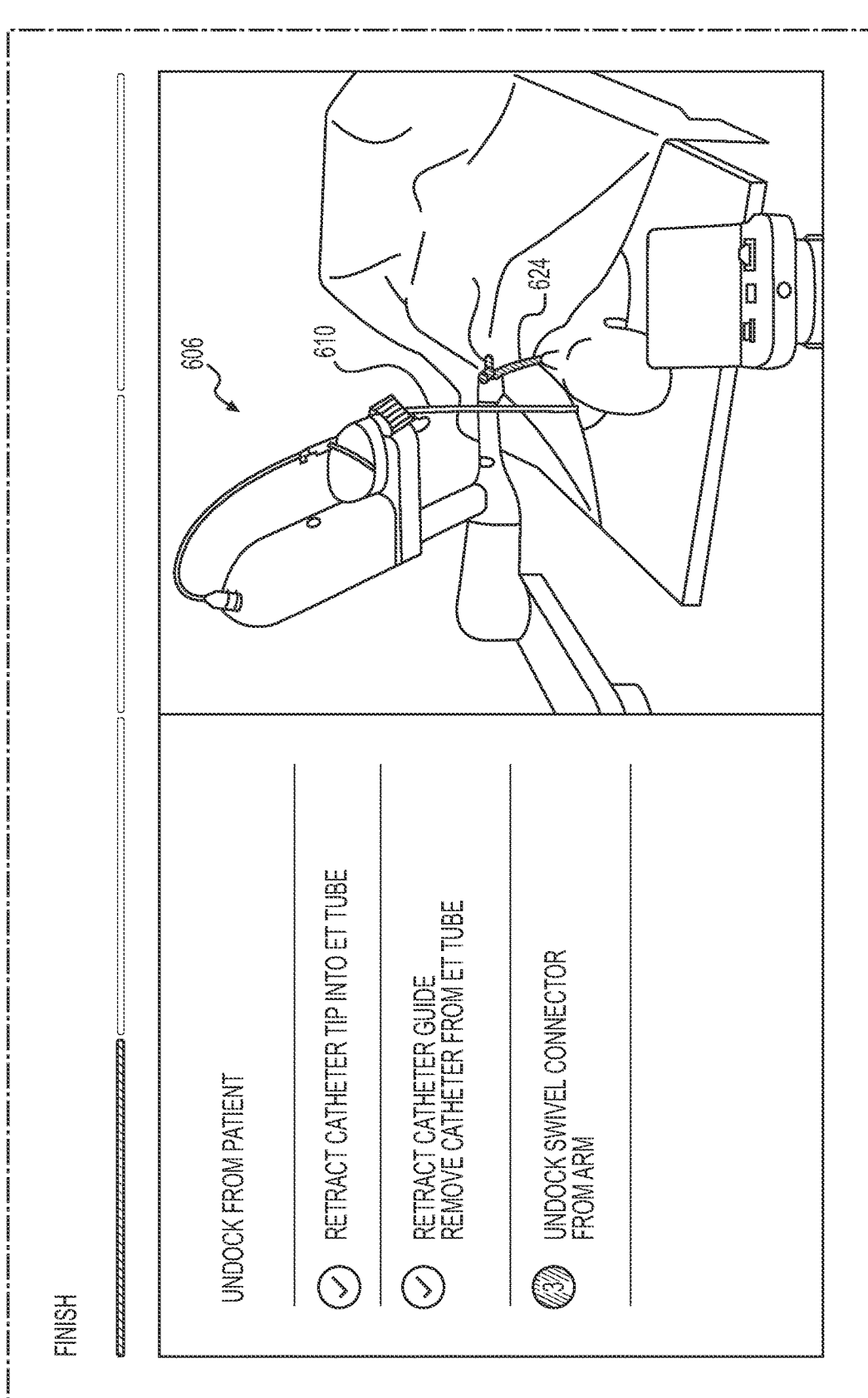
Figure 7D:
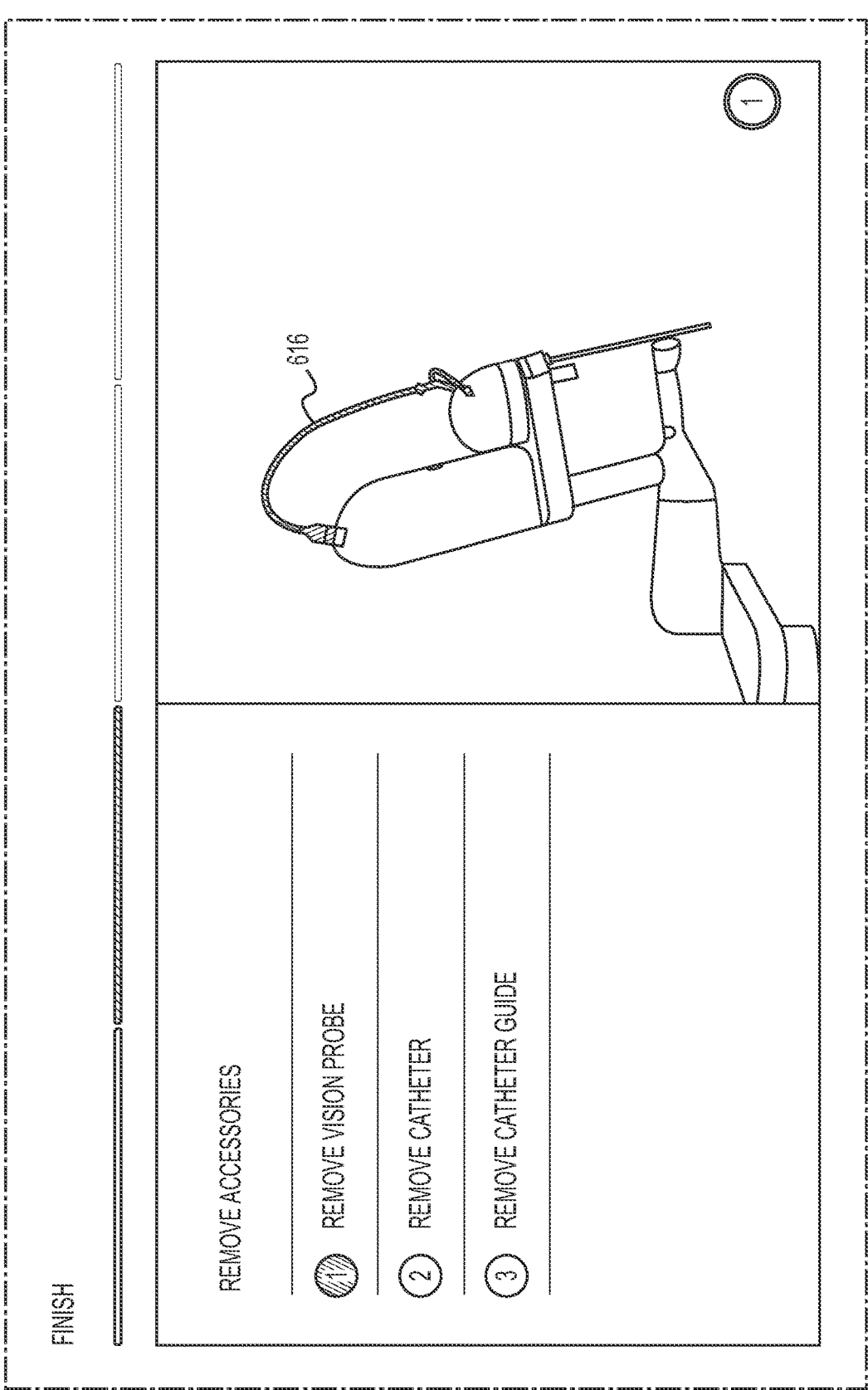
Figure 7E:
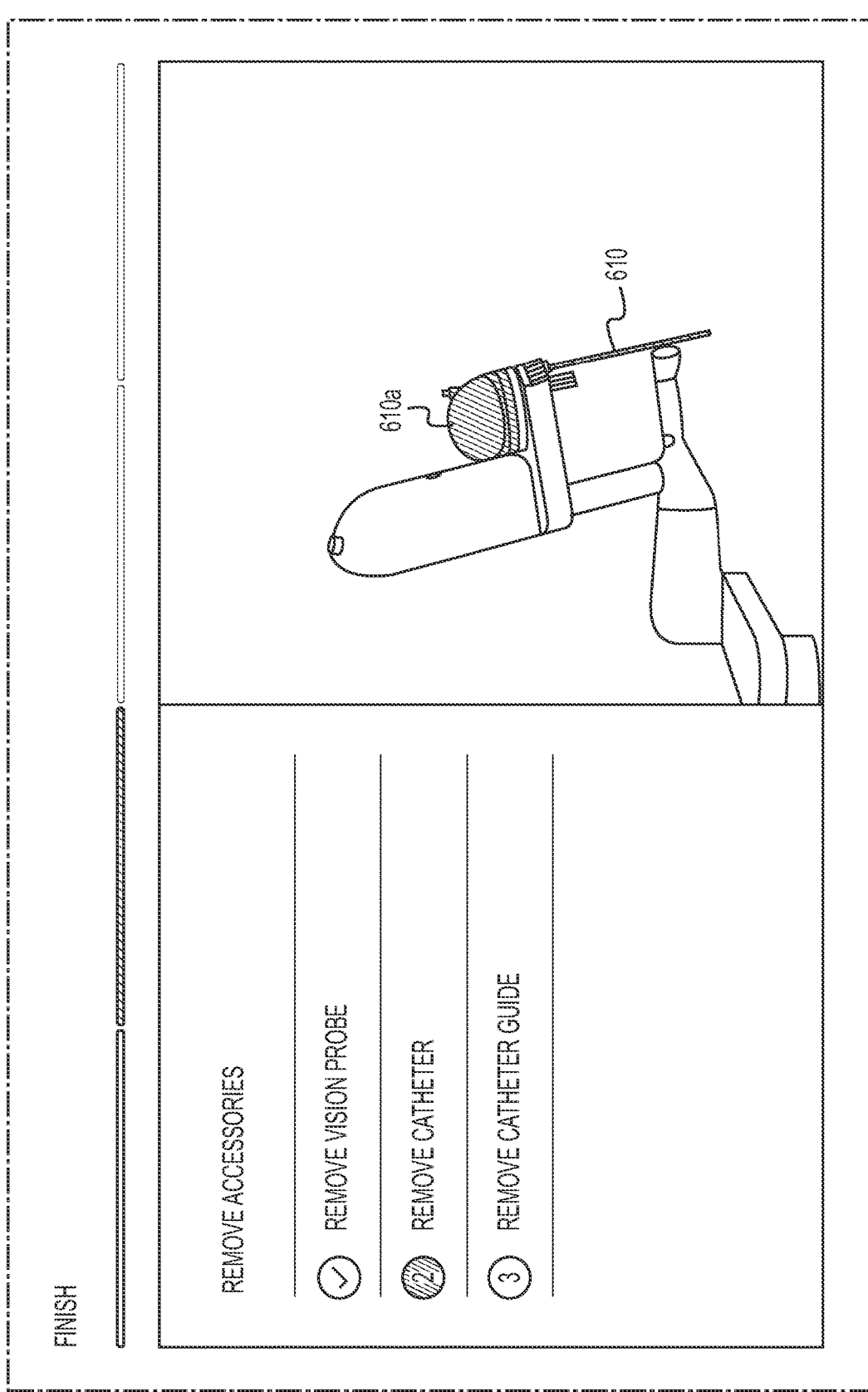
Figure 7F:
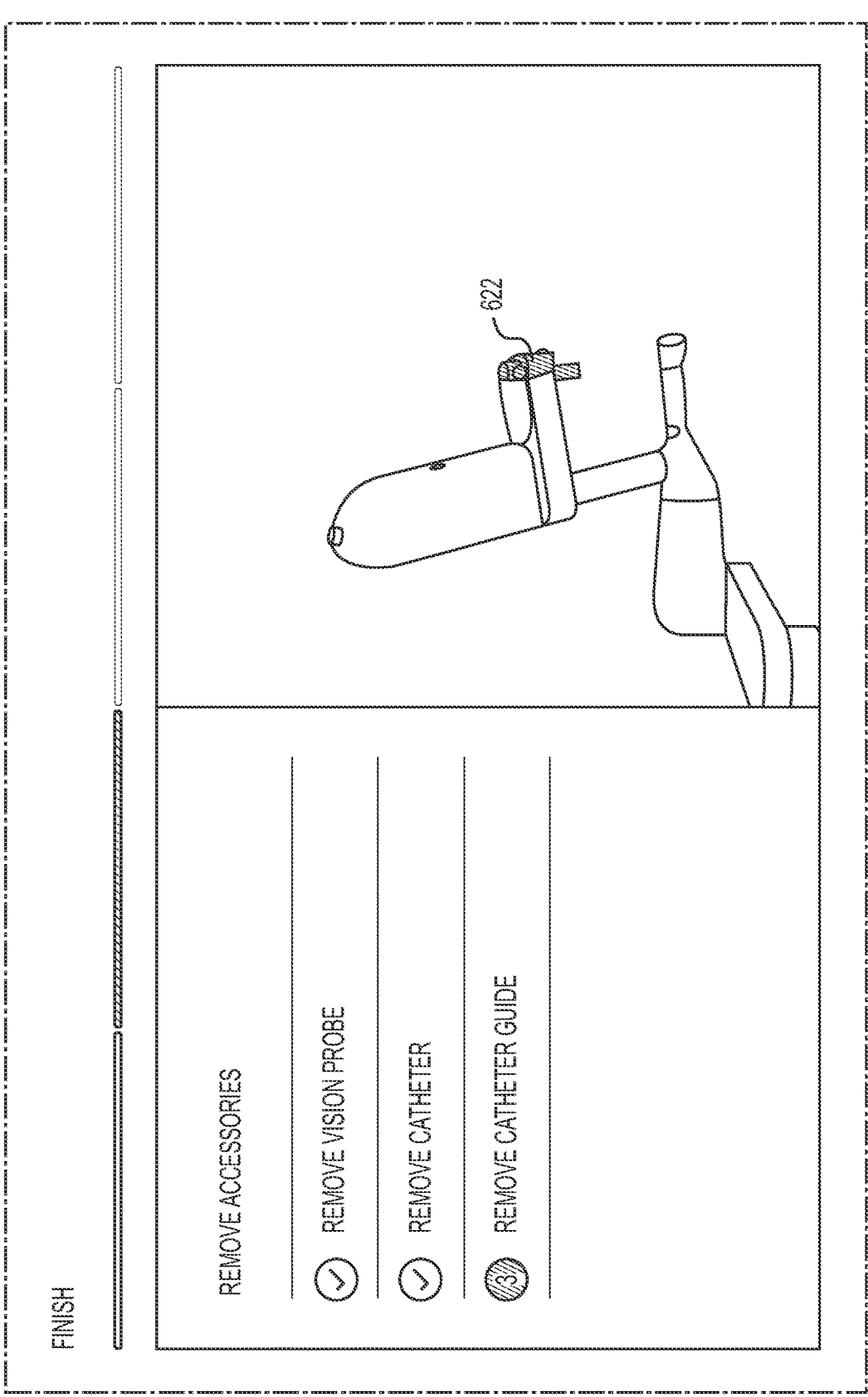

In some embodiments, the catheter 610 is navigated through patient anatomy during a medical procedure, positioning a distal tip of the catheter 610 at an anatomical target. Upon completion of the procedure, the catheter can be retracted from anatomy. The first guided step for tear down ("Undock from Patient") in accordance with one embodiment of the present disclosure, is to retract the catheter distal tip (see catheter 610 in FIG. 7C, for example) from patient anatomy of patient P, into the endotracheal tube 624, as indicated and shown in the visual representation of FIG. 7A. The next step, as shown in the visual representation of FIG. 7B, is to retract the catheter guide 622 (visually emphasized in the diagram) and to remove the catheter 610 from the endotracheal tube 624. As indicated by the visual representation of FIG. 7C, the next step is to undock the device connector 618 (visually emphasized) from the arm 606. Once the step of undocking the device connector 618 from the arm 606 is complete, then the three listed steps for "Undock from Patient" are complete. After undocking from the patient, the next guided steps of the tear down process are, as indicated in the visual representations of FIGS. 7D, 7E, and 7F, to remove accessories ("Remove Accessories"), which includes the listed steps of (in the listed order as shown): removing the vision probe 616 as shown in FIG. 7D, with the vision probe 616 visually emphasized; removing the catheter 610, as shown in FIG. 7E, with the catheter 610 and control assembly 610a (e.g., control assembly 310b, FIG. 3A) visually emphasized; and removing the catheter guide 622, as shown in FIG. 7F, with the catheter guide 622, in retracted form, visually emphasized.

Figure 7G:
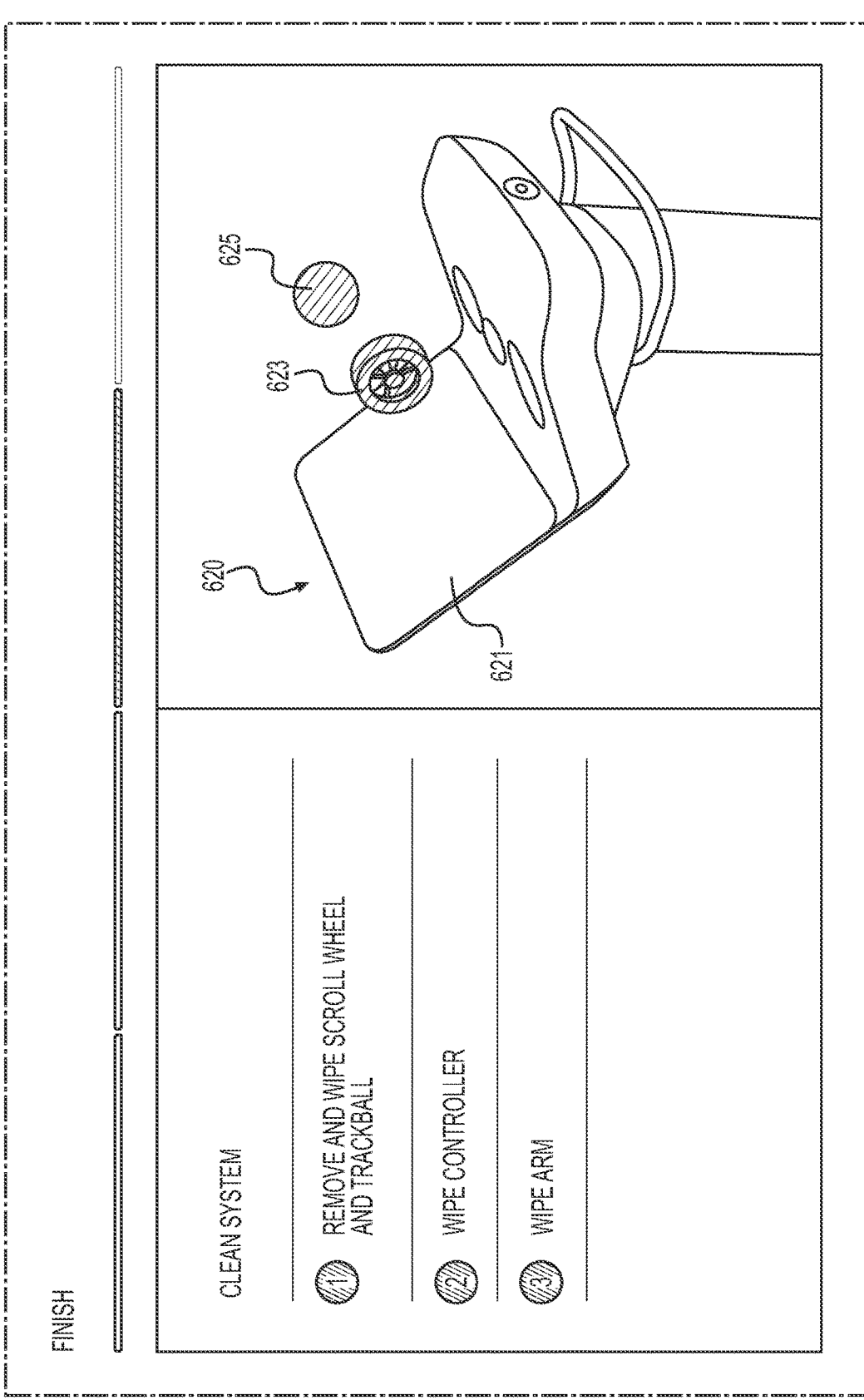

After the steps for "Remove Accessories" are complete, the next guided steps for tear down are for cleaning the system ("Clean System", visually represented in FIG. 7G). The first step of cleaning the system is to remove and wipe the scroll wheel 623 and trackball 625 (both visually emphasized in the diagram of FIG. 7G) of the controller 620 (e.g., master control 220, FIG. 2). As discussed above with respect to the master control 220 in FIG. 2, in some embodiments, the scroll wheel (623 in FIG. 7G) may be rolled forwards or backwards in order to control the advancement or retraction of a medical instrument such as a catheter with respect to patient anatomy, and the trackball (625 in FIG. 7G) may be rolled in various directions by an operator in order to steer the position of the distal end portion and/or distal tip of an elongate device such as a catheter. The next guided step for cleaning the system is to wipe (e.g., rub with a cleaning cloth and/or cleaning agent) remaining portions and surfaces (e.g., touchscreen) of the controller 620 and to clean the arm ("wipe arm") (see, e.g., arm 606 in FIG. 7A).

Figure 7H:
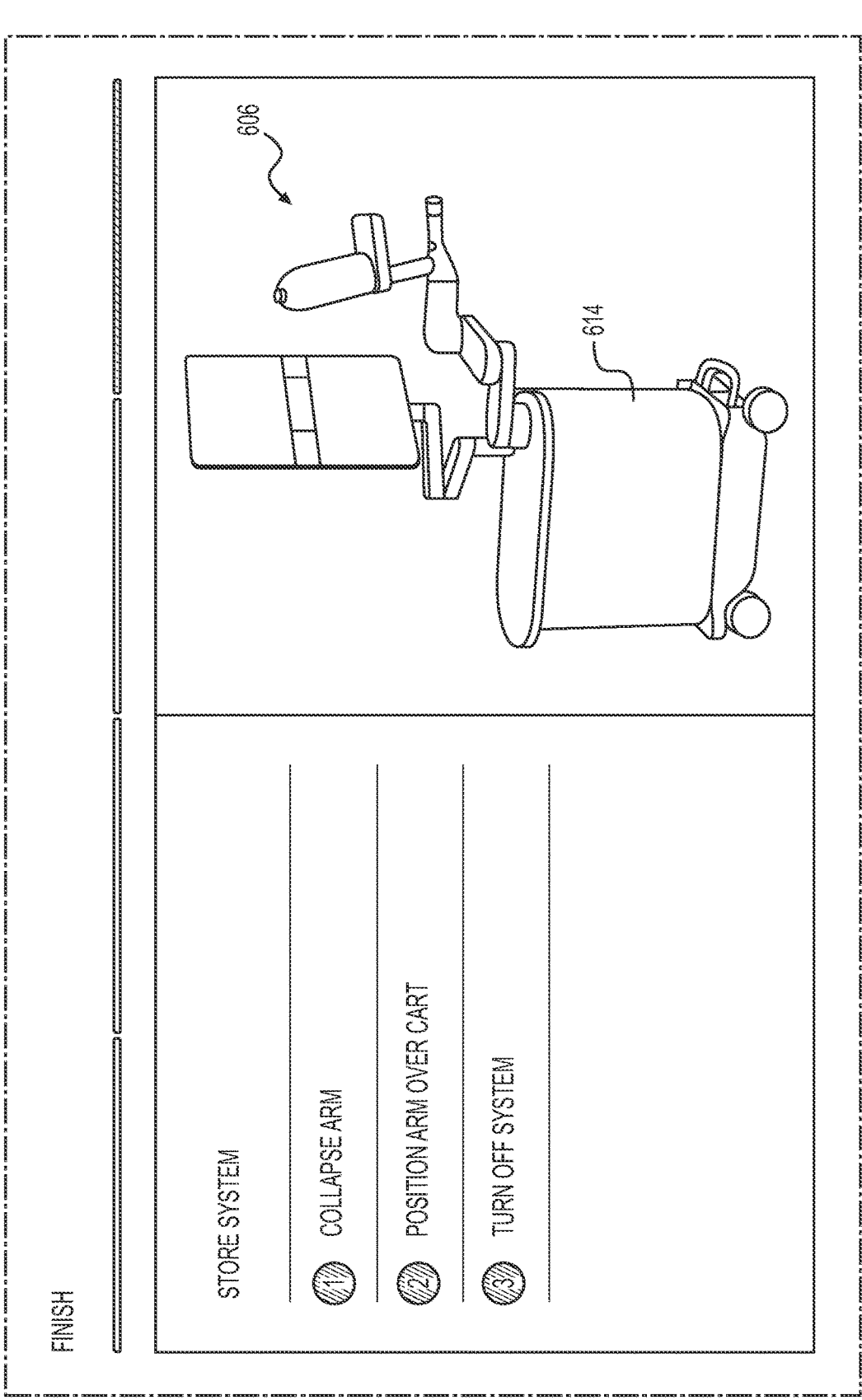

After the "Clean System" steps are complete, the next steps of the guided tear down are the "Store System" steps indicated in FIG. 7H, which include collapsing the arm 606, positioning the arm 606 over the cart 614 (e.g., system cart 214, FIG. 2), and then turning off the system. An example of a system in a stored configuration is shown in FIG. 2B and a corresponding description for placing the system into the stored configuration is provided in the discussion of FIG. 2B.

Figure 8A:
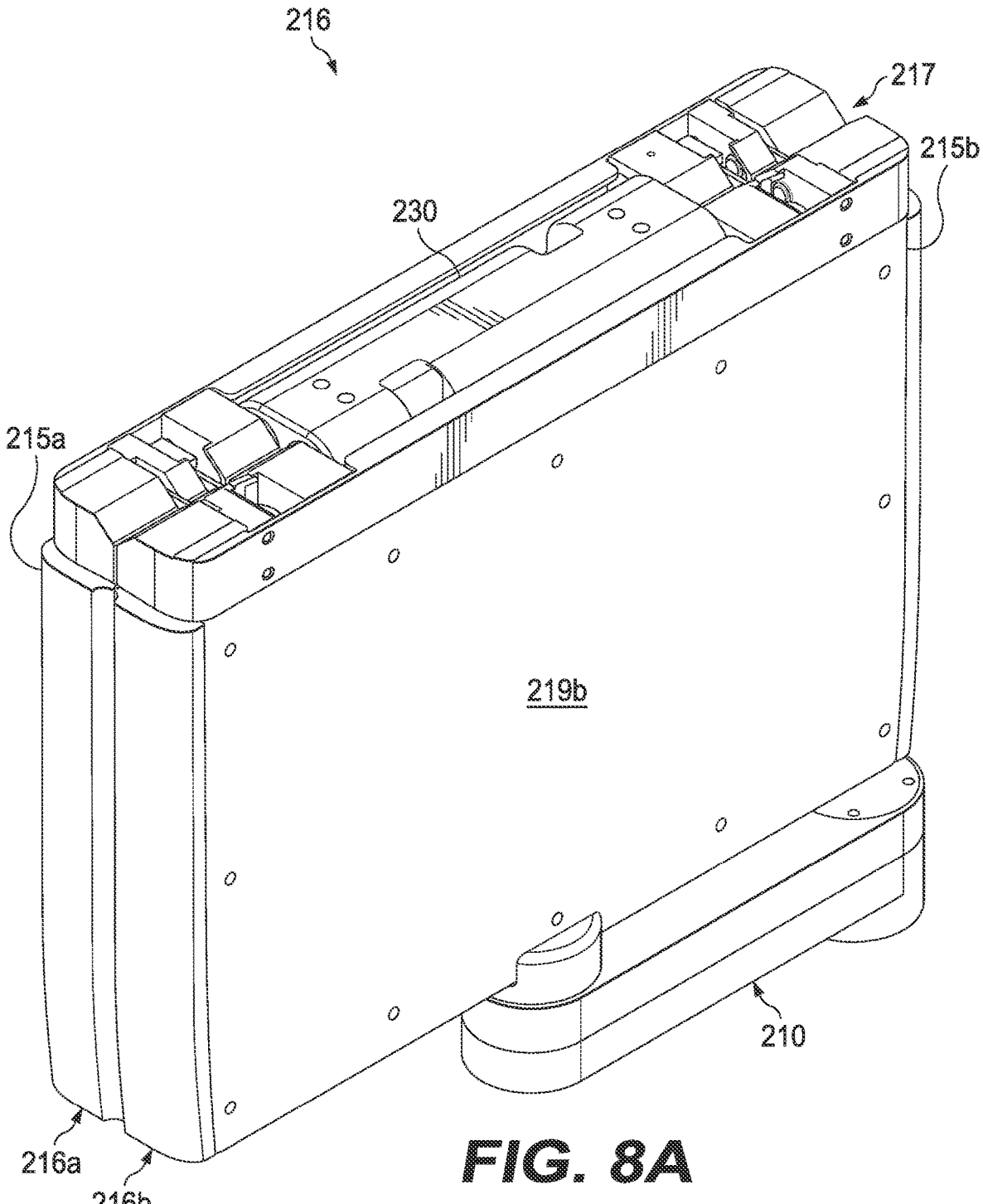
FIGS. 8A and 8B illustrate various aspects of a display system according to some embodiments.
Figures 8B, 8C:
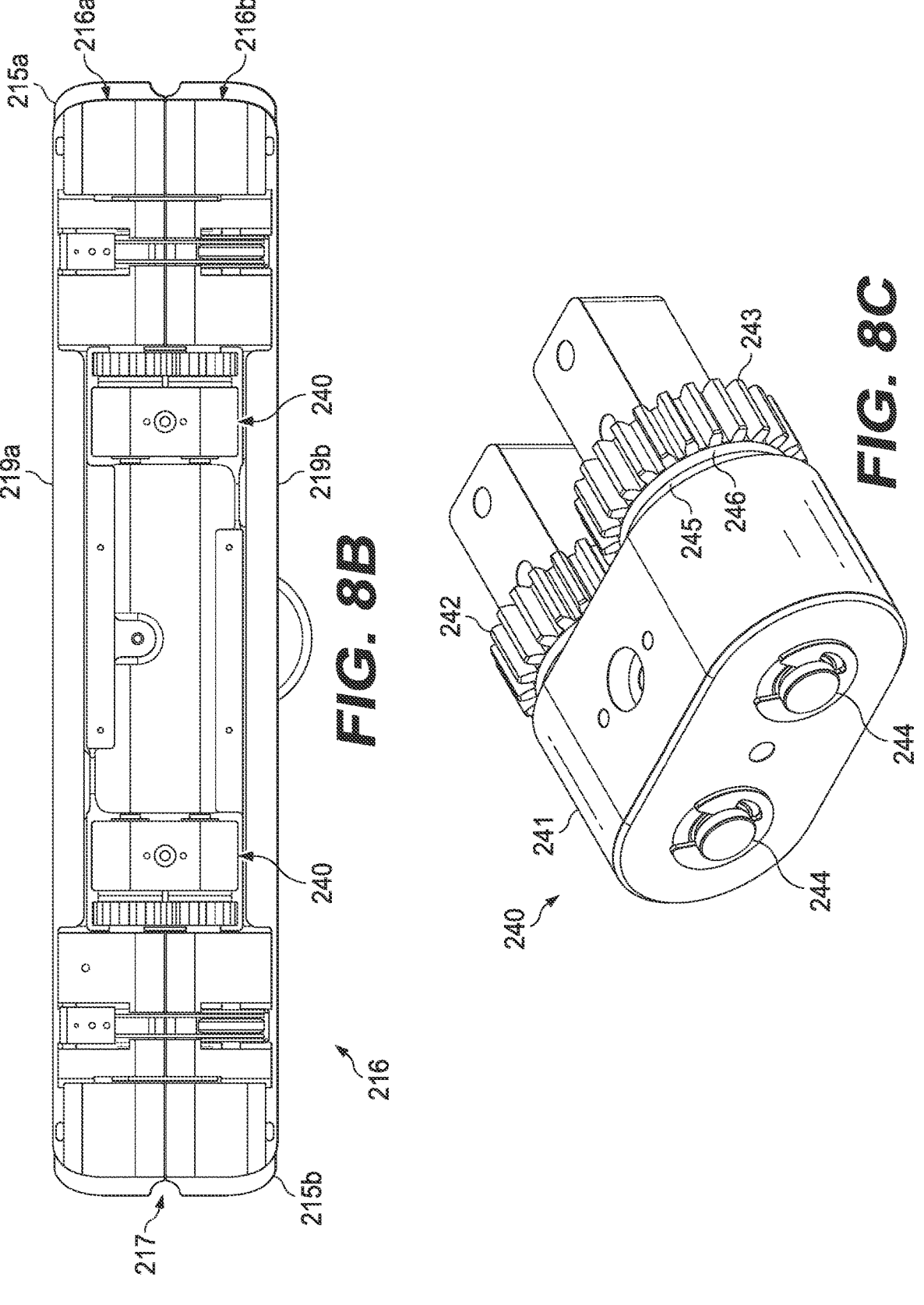
FIGS. 8C-8E illustrate various aspects of a gear hinge assembly according to some embodiments.
Figure 9A:
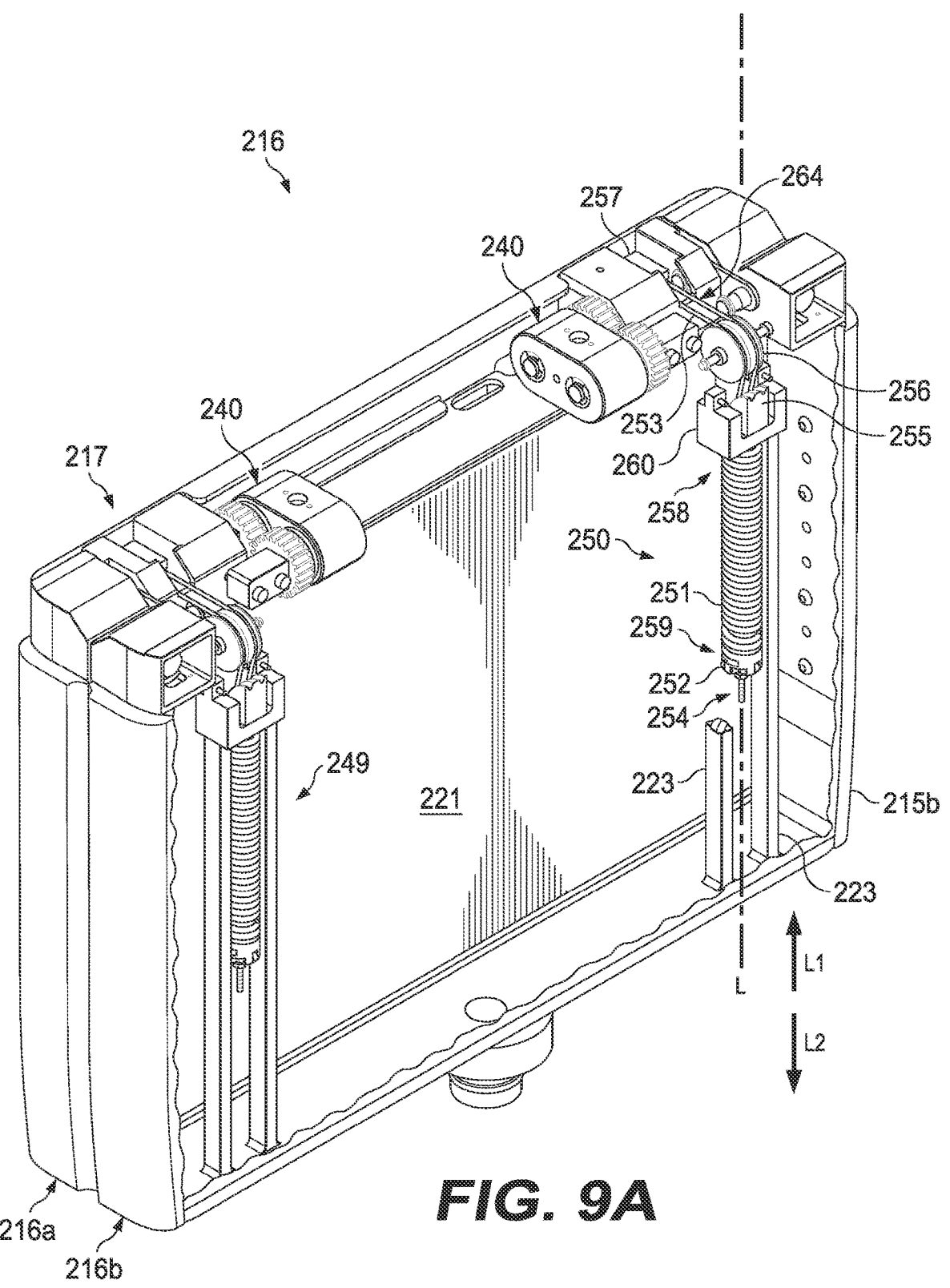
FIGS. 9A and 9B illustrate various aspects of a counterbalance system when a display system is in a closed configuration according to some embodiments.
Figure 9B:
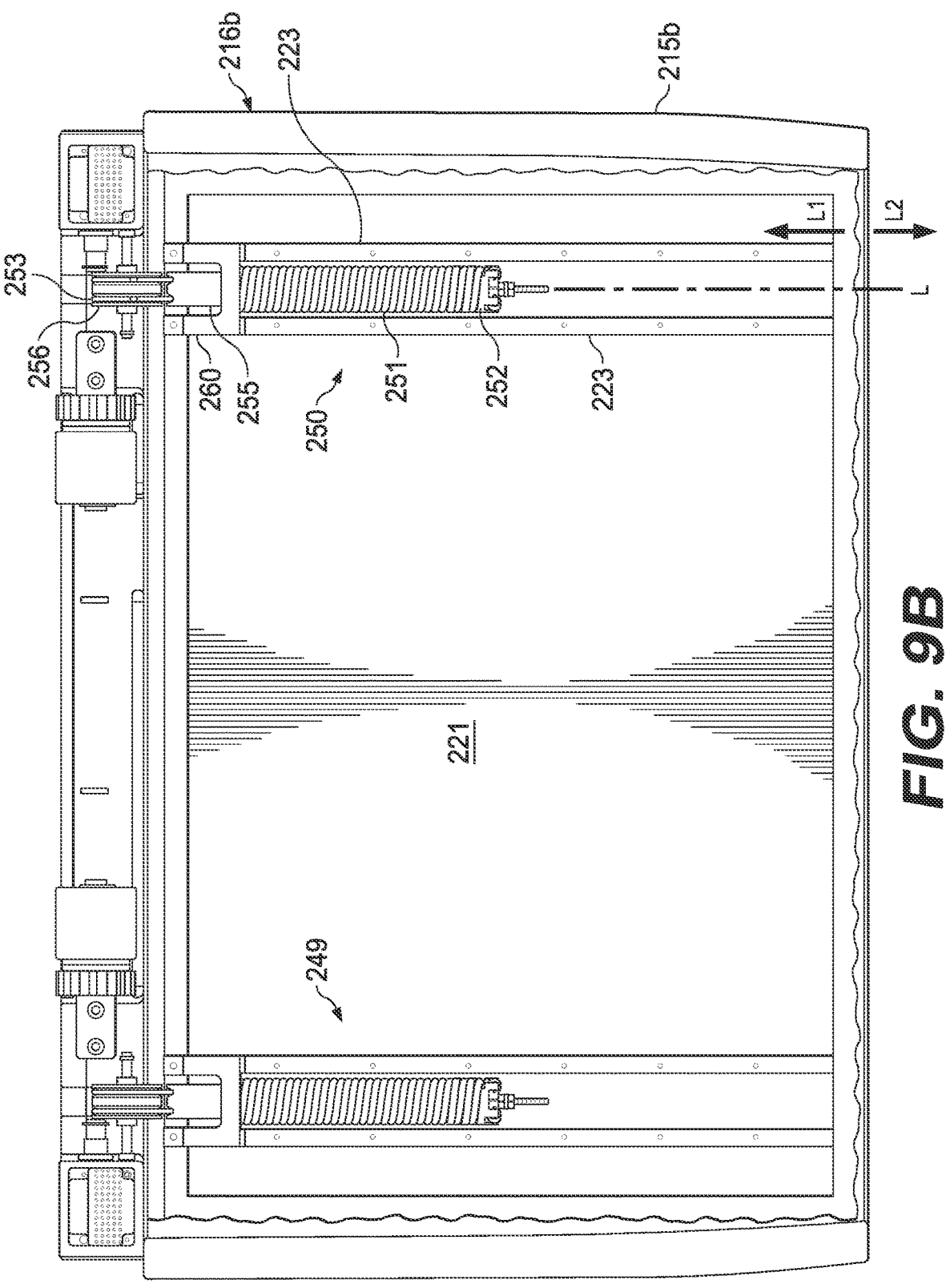

With reference to FIG. 2, the display system 216 includes the monitor support arm 210 and the display monitors 216a, 216b. As shown in FIG. 2, the display monitors 216a, 216b may be arranged in an open configuration or partially opened configuration in which the display screens of both monitors are visible to a user. The monitor 216a may be referred to as an upper monitor and/or a first member, and the monitor 216b may be referred to as a lower monitor and/or a second member. In a fully open configuration, the monitors 216a, 216b may be oriented at approximately 180 degrees from each other. In a partially open configuration, the monitors 216a, 216b may be oriented between 0 and 180 degrees from each other or between 180 and 360 degrees from each other in an extended position. Additionally, the relative range of motion of the monitors 216a, 216b may be between 0 and 360 degrees from each other. FIG. 8A shows the display system 216 in a collapsed or closed configuration according to some embodiments. In this embodiment, the monitors 216a, 216b are coupled together by a hinge mechanism 217. Each monitor 216a, 216b includes a housing 215a, 215b, respectively. As shown in FIGS. 8A and 8B, the housings 215a and 215b may include a back panel 219a and 219b, respectively. In the closed configuration, the monitors 216a, 216b are generally adjacent to each other and are generally in parallel alignment. FIGS. 9A and 9B illustrate the housings 215a and 215b as a cutaway hiding the back panel 219b for clarity. A display screen 221 is illustrated mounted to an inner facing surface of the housing 215b. A display screen (not shown in FIGS. 9A and 9B) can additionally be mounted on an inner facing surface of the housing 215a such that in the closed configuration, the display screens 221 of the monitors 216a, 216b may be facing each other. In some alternative embodiments, the display screens 221 can be mounted on outer surfaces of housings 215a and 215b, such that the display screens 221 may be facing away from each other. In further alternative embodiments, any number of display screens 221 from 1 to 4 display screens, for example, can be mounted on the housing 215a and/or the housing 215b on the inner and/or outer surface of the housing 215a and/or the housing 215b.

The display system 216 also includes a hinge cover 230. The hinge cover 230 covers and protects the one or more components of the hinge mechanism 217. The hinge cover 230 may also house cables (e.g., mechanical cables, electrical cables, etc.) and help route the cables to protect the cables from excess bending stress. Additionally, the hinge cover 230 may house other components of the display system 216, such as a monitor sensor, a tilt sensor, etc. The monitor 216b is coupled to the monitor support arm 210 and, therefore, may move with the monitor support arm 210 as the monitor support arm 210 moves (e.g., translates, rotates, etc.). Similarly, the monitor 216a is coupled to the monitor 216b and, therefore, may move with the monitor 216a as the monitor 216b moves (e.g., translates, rotates, etc.). In some examples, the monitor 216a rotates via the hinge mechanism 217 relative to the monitor 216b, which allows the monitor 216a to be positioned at a desired viewing angle or to be folded and stowed in a collapsed configuration against monitor 216b for storage. The monitors 216a, 216b may rotate via the hinge mechanism 217 to position the monitors in the closed configuration, the partially open configuration or the fully open configuration. In embodiments where the monitors 216a, 216b are in an open configuration (whether fully open or partially open), the monitor 216a is spaced from and/or positioned above the monitor 216b (see FIGS. 10, 11).

In some embodiments, the weight of the monitor 216a may bias the display system 216 toward the closed configuration. As described below, systems may be provided to apply forces (for example torques) that counteract the weight of the monitor 216a to allow the monitor to be moved to and maintained in the open or partially open configuration. Such systems may include a frictional gear hinge assembly and/or a counterbalance system.

FIG. 8B shows the closed configuration of the display system 216 with the hinge cover 230 removed. In this embodiment, the hinge mechanism 217 includes two gear hinge assemblies 240. As shown in FIG. 8B, each gear hinge assembly 240 is connected to both monitors 216a, 216b. The gear hinge assemblies 240 may provide a frictional force that contributes to a system stasis when the display system 216 is in an opened or partially opened configuration For example, when the monitor 216a is pivoted about the hinge mechanism 217 with respect to the monitor 216*b* into an open or partially opened configuration, the frictional force provided by the gear hinge assemblies helps prevent small, incidental movements (e.g., bumping one or both of the monitors 216*a*, 216*b*, touching one or both of the monitors 216*a*, 216*b*, etc.) from causing the orientation of the monitor 216*a* with respect to monitor 216*b* to change. Accordingly, in some embodiments, once the orientation of the monitors 216*a*, 216*b* is set, the orientation of the monitors with respect to each other will not change unless some affirmative action is taken to change the orientation. In alternative embodiments, the hinge mechanism 217 may include a single gear hinge assembly 240 or more than two gear hinge assemblies.

Figure 8D:
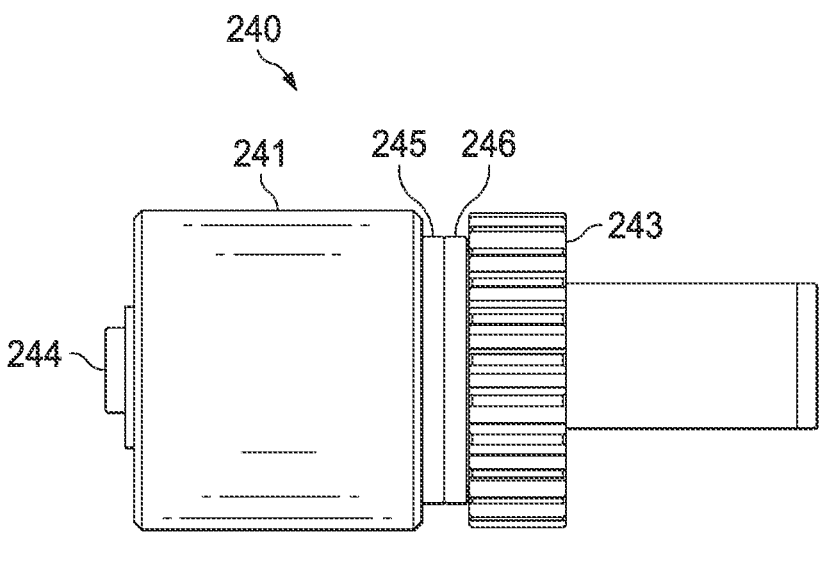
Figure 8E:
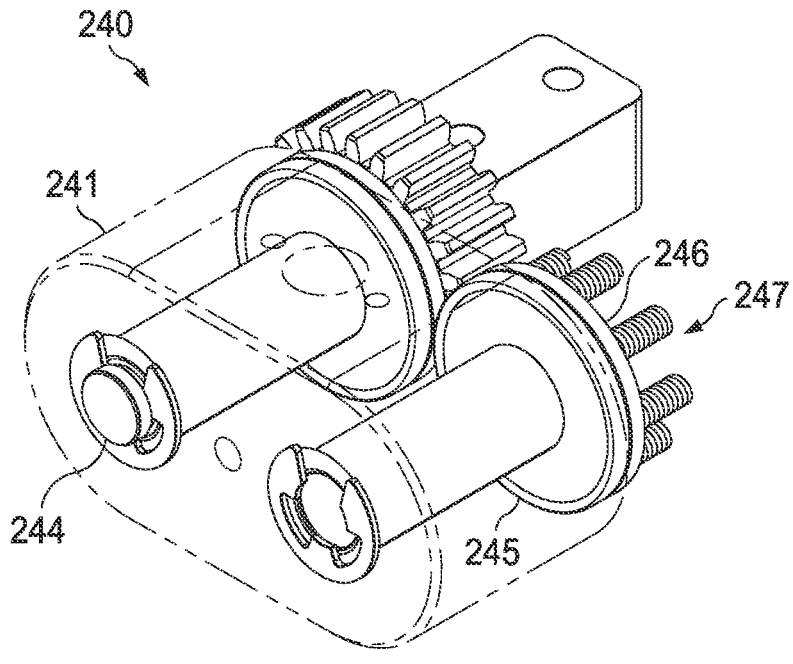

FIG. 8C illustrates a perspective view of the gear hinge assembly 240 according to some embodiments. FIG. 8D illustrates a side view of the gear hinge assembly 240 according to some embodiments. FIG. 8E illustrates a cutaway perspective view of the gear hinge assembly 240 according to some embodiments. The gear hinge assembly 240 includes a gear block 241, an upper gear 242, and a lower gear 243. The gear block 241 may also be referred to as a housing. The upper and lower gears 242, 243 are in a generally parallel alignment and are engaged so that at least one of the gears rotates with respect to the other as the monitors 216*a*, 216*b* are rotated relative to each other. The upper gear 242 may be housed in the upper monitor 216*a*, and the lower gear 243 may be housed in the lower monitor 216*b*. Each of the gears 242, 243 is coupled to the gear block 241 by a retaining member 244. A set of springs 247 extend within each of the gears 242, 243. For case of explanation, the following discussion will be made with reference to the lower gear 243 and the corresponding components of the gear hinge assembly 240. It is to be understood that the discussion similarly applies to the upper gear 242 and the corresponding components of the gear hinge assembly 240. The set of springs 247 (also referred to as biasing members) housed within the gear 243 engage a spring plate 246 that is positioned between the gear block 241 and the gear 243. The spring plate 246 (which may be referred to as a second friction member), is arranged coaxially with the gear 243 and the retaining member 244 (e.g., a retaining ring, a clip, a screw, and/or the like). A friction plate 245 (which may be referred to as a first friction member), extends between the gear block 241 and the spring plate 246. The friction plate 245 is arranged coaxially with the gear 243, the spring plate 246, and the retaining member 244. In some embodiments, the spring plate 246 is rotationally locked with the gear 243. In such embodiments, the spring plate 246 and the gear 243 rotate together. In some examples, the spring plate 246 and the gear 243 may be rotationally locked via a mechanical connection, an adhesive connection, etc. In other embodiments, the friction plate 245 is rotationally locked with the gear 243. In such embodiments, the friction plate 245 and the gear 243 rotate together. In some examples, the friction plate 245 and the gear 243 may be rotationally locked via a mechanical connection, an adhesive connection, etc. In some examples, the friction plate 245 is rotationally locked with the spring plate 246. In such examples, the friction plate 245 and the spring plate 246 rotate together. In some embodiments, the friction plate 245 and the spring plate 246 may be rotationally locked via a mechanical connection, an adhesive connection, etc. In further embodiments, the friction plate 245 may be rotationally locked with both the spring plate 246 and the gear 243. In several embodiments, the friction plate 245 is axially movable so that the springs

247 can expand to allow for any wear of the friction plate 245 that may occur over time.

The plurality of springs 247 provide a force against the spring plate 246. The force may be evenly distributed around the spring plate 246, or the force may be unevenly distributed around the spring plate 246 depending on the arrangement of the springs 247 within the lower gear 243. In some embodiments, each spring of the plurality of springs 247 is coupled to a corresponding screw. Each screw may be individually adjusted to adjust the force each spring provides against the spring plate 246. The force from the springs 247 is transferred from the spring plate 246 to the friction plate 245. The force is then transferred from the friction plate 245 to the gear block 241. The resulting friction force between the friction plate 245 and the gear block 241 provides a passive, constant friction to help hold the monitors 216*a*, 216*b* in an open or partially open configuration. In some embodiments, each gear hinge assembly 240 has a specific friction unique to each individual gear hinge assembly 240. The level of friction applied by the gear hinge assembly 240 to the display system 216 may be adjusted to fit the operator's preferences and/or to apply a sufficient amount of friction to account for the specifications (size, weight, etc.) of the monitors 216*a*, 216*b*. In some embodiments, these adjustments may be made during the manufacturing process, before the gear hinge assembly 240 is coupled to the monitors 216*a*, 216*b*. In other embodiments, the adjustments may be made after the gear hinge assembly 240 is coupled to the monitors 216*a*, 216*b*.

In some embodiments, the friction force may be adjusted by changing the rate of the springs 247 depending on the size and weight of the monitors 216*a*, 216*b*. In some embodiments, the plurality of springs 247 is arranged in a circular formation within the lower gear 243. In some examples, the individual springs may be equidistantly spaced in a circumferential direction around the lower gear 243. In other examples, the individual springs may be randomly spaced or spaced in a non-equidistant pattern in a circumferential direction around the lower gear 243. In still other instances, only one spring may be included in the lower gear 243. In such instances, the one spring may be concentric to the lower gear 243 such that the spring spans 360 degrees in a circumferential direction around the lower gear 243.

In several examples, the friction plate 245 may be made of a high-friction material. In some embodiments, the gear block 241 may also be made of a high-friction material. In further embodiments, the spring plate 246 may be made of a low-friction material. In alternative embodiments, both the friction plate 245 and the spring plate 246 may be made of a high-friction material.

In some embodiments, the weight of the monitor 216*a* may be so great that the frictional force needed in the gear hinge assemblies 240 to maintain the monitors in an open or partially open configuration would be so large that a user may be unable to easily overcome the frictional force to adjust the orientation of the monitors relative to each other. To prevent the monitor 216*a* from rotating about the hinge mechanism 217 when the display system 216 is in a partially open or open configuration and yet allow the monitor 216*a* to be rotatably adjusted with ease, the display system may include a counterbalance system 250 as shown in FIGS. 9A and 9B. With the counterbalance system 250, the display system 216 may be optimized to achieve a sufficiently high constant friction in the gear hinge assemblies 240 to maintain the monitors 216*a*, 216*b* in an open or partially open configuration while also allowing a user to adjust the orientation of the monitors 216*a*, 216*b* relative to each other without difficulty. As discussed in greater detail below, the friction in the gear hinge assemblies 240 coupled with counterbalance forces (which may be counterbalance torques) provided by a counterbalance system is used to achieve forces (e.g., torques) in the display system 216 that maintain a selected monitor orientation while allowing a user to easily overcome the friction to adjust the orientation. In this embodiment, the gear hinge assembly 240 may act as a constant brake (such as a passive brake) in the display system 216.

In alternative embodiments, the counterbalance system 250 applies a counterbalancing force to the display system 216 before the need for any frictional force. In some embodiments, the counterbalance force (e.g., a counterbalance torque) provided by the counterbalance system 250 may be similar to, but not equal to, a monitor force (e.g., a torque) that is present in the display system 216 when the monitors 216a, 216b are rotated relative to each other. Therefore, a difference between the counterbalance force and the monitor force may be present. In several embodiments, to compensate for this difference between the forces, a friction force, such as the friction force in the gear hinge assemblies 240, is applied to the display system 216. The friction force may be larger than the difference between the counterbalance force and the monitor force. As discussed above, the friction force in the gear hinge assemblies 240 may be adjusted to provide a desired friction force to the display system 216 depending on the difference between the counterbalance force and the monitor force. For example, if the difference between the counterbalance force and monitor force is relatively large, then the friction force will be relatively large. In another example, if the difference between the counterbalance force and monitor force is relatively small, then the friction force will be relatively small. The friction force may be adjusted to any desired amount such that the monitor force is substantially equal to the combination of the counterbalance force and the friction force.

Figure 10:
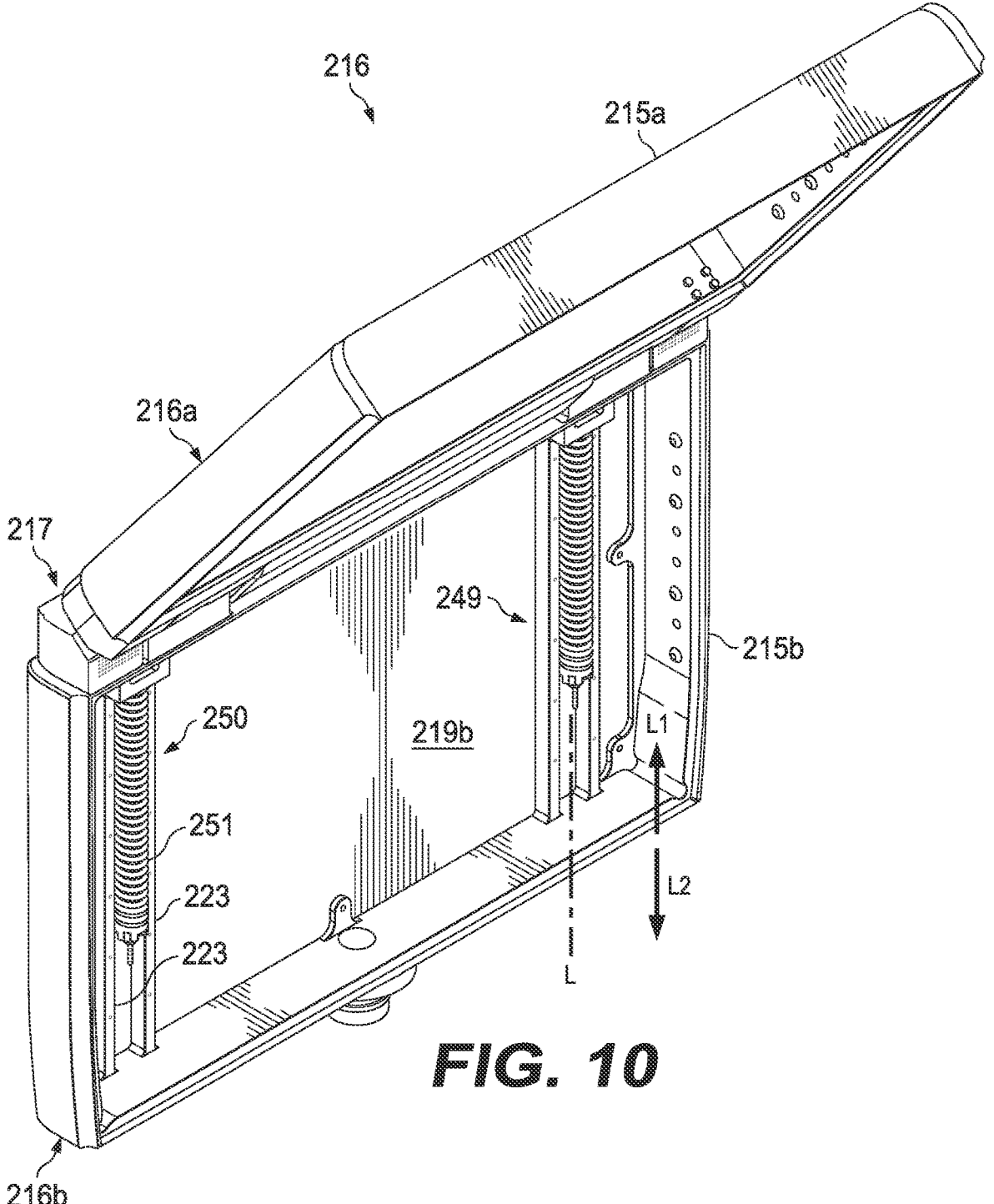
FIG. 10 illustrates various aspects of a counterbalance system when the display system is in a partially open configuration according to some embodiments.

FIGS. 9A and 9B show a counterbalance system 249 and a counterbalance system 250 when the display system 216 is in a closed configuration. In FIGS. 9A and 9B, the back panel 219b is cut away. In several embodiments, the counterbalance systems 249, 250 (which may also be referred to as counterbalance assemblies) are housed within the housing 215b. In the embodiment shown in FIGS. 9A and 9B, the display system 216 includes two counterbalance systems 249, 250 in the monitor 216b. In alternative embodiments, the monitor 216b may only include one counterbalance system 250. In other embodiments, the monitor 216b may include more than two counterbalance systems 250. In further alternative embodiments, one or more of the counterbalance systems 249, 250 may be included within the monitor 216a. Accordingly, one or more counterbalance systems 249, 250 may be included in one or both of the monitors 216a, 216b. In some embodiments, the display system 216 only includes one monitor, e.g., the monitor 216a. In such embodiments, the pivot point is about the hinge 217 (as illustrated in FIG. 10), and the monitor 216a rotates about a horizontal axis along a bottom horizontal edge of the monitor 216a. In other embodiments, the pivot point can be at a different location along the surface of the monitor 216a such that the monitor 216a can rotate about a horizontal axis at the center of the monitor 216a, a horizontal axis along a top horizontal edge, or any horizontal axis between the bottom horizontal edge and the top horizontal edge of the monitor 216a. In other embodiments, the axis of rotation is at an angle from horizontal. The one or more counterbalance systems 249, 250 may be included within the monitor 216a and the location of the one or more counterbalance systems 249, 250 is correspondingly variable based on the location of the pivot point of the monitor 216a. Alternatively, one or more counterbalance systems 249, 250 may be included within the support arm 210 or within another component of the system cart 214. The description that follows will describe the counterbalance system 250, but the same description applies to the counterbalance system 249.

The counterbalance system 250 includes a biasing member such as a spring 251, a spring termination 252 (which may also be a termination member), a cable 253, a preload adjustment assembly 254, a sector pulley 255, a pulley 256, and a hinge connector 257. In the counterbalance system 250, the spring 251 includes a proximal portion 258 and a distal portion 259. The proximal portion 258 is coupled to a block 260, and the distal portion 259 is coupled to the spring termination 252. The proximal portion 258 may be coupled to the block 260 with a mechanical connection, an adhesive connection, or any other suitable connection. The block 260 may be rigid and may be fixedly or integrally coupled to the monitor housing 215b such as to the back panel 219b. A pair of rails 223 may extend from the block 260 and may generally extend alongside the spring 251. The rails 223 may be fixed to or integrally formed with the back panel 219b.

The distal portion 259 of the spring 251 may be coupled to the spring termination 252. In several embodiments, the spring termination 252 is movable in a direction L1 or L2 generally parallel to a longitudinal axis L of the spring 251. As the orientation of monitor 216a is adjusted relative to the monitor 216b, the cable 253 is moved by the hinge connector 257, and the spring 251 is correspondingly compressed or stretched. As the spring 251 is compressed or stretched, the distal portion 259 of the spring 251 and the spring termination 252 move up (toward the hinge mechanism 217) and down (away from the hinge mechanism 217) within the monitor 216b along the axis L. The spring termination 252 moves up and down due to the movement of the cable 253, which pulls the spring termination 252 up and down.

A first end of the cable 253 is coupled to the spring termination 252. From the spring termination 252, the cable 253 extends through the spring 251 such that the spring 251 surrounds the cable 253. The cable 253 further extends across the sector pulley 255 which may be fixedly mounted to the housing 215b, such as to the back panel 219b. In some embodiments, the sector pulley 255 may be coupled to or may be positioned on the block 260. The cable 253 further extends around the pulley 256 which may be rotatably or fixedly coupled to the housing 215b. The cable 253 further loops across the hinge connector 257 and extends back around the pulley 256, across the sector pulley 255, and through the spring 251. The second end of the cable 253 is coupled to the spring termination 252. The hinge connector 257 is coupled to the monitor 216a, e.g., to the housing 215a.

As the monitor 216a is moved to the closed configuration from an open or partially open configuration, the hinge connector 257 rotates with the monitor 216a, relative to the monitor 216b, and away from the pulley 256. In several embodiments, as the hinge connector 257 rotates away from the pulley 256, the hinge connector 257 pulls the cable 253 in a direction away from the pulley 256. As the cable 253 is pulled by the hinge connector 257, the cable 253 travels around the pulley 256. In several embodiments, the pulley 256 rotates as the cable 253 travels around the pulley 256. The rotation of the pulley 256 reduces any friction forces between the cable 253 and the pulley 256. This reduction in friction force allows the counterbalance system 250 to smoothly apply a counterbalance force as the monitors 216a, 216b transition between the closed configuration and a fully open configuration.

Figure 9C:
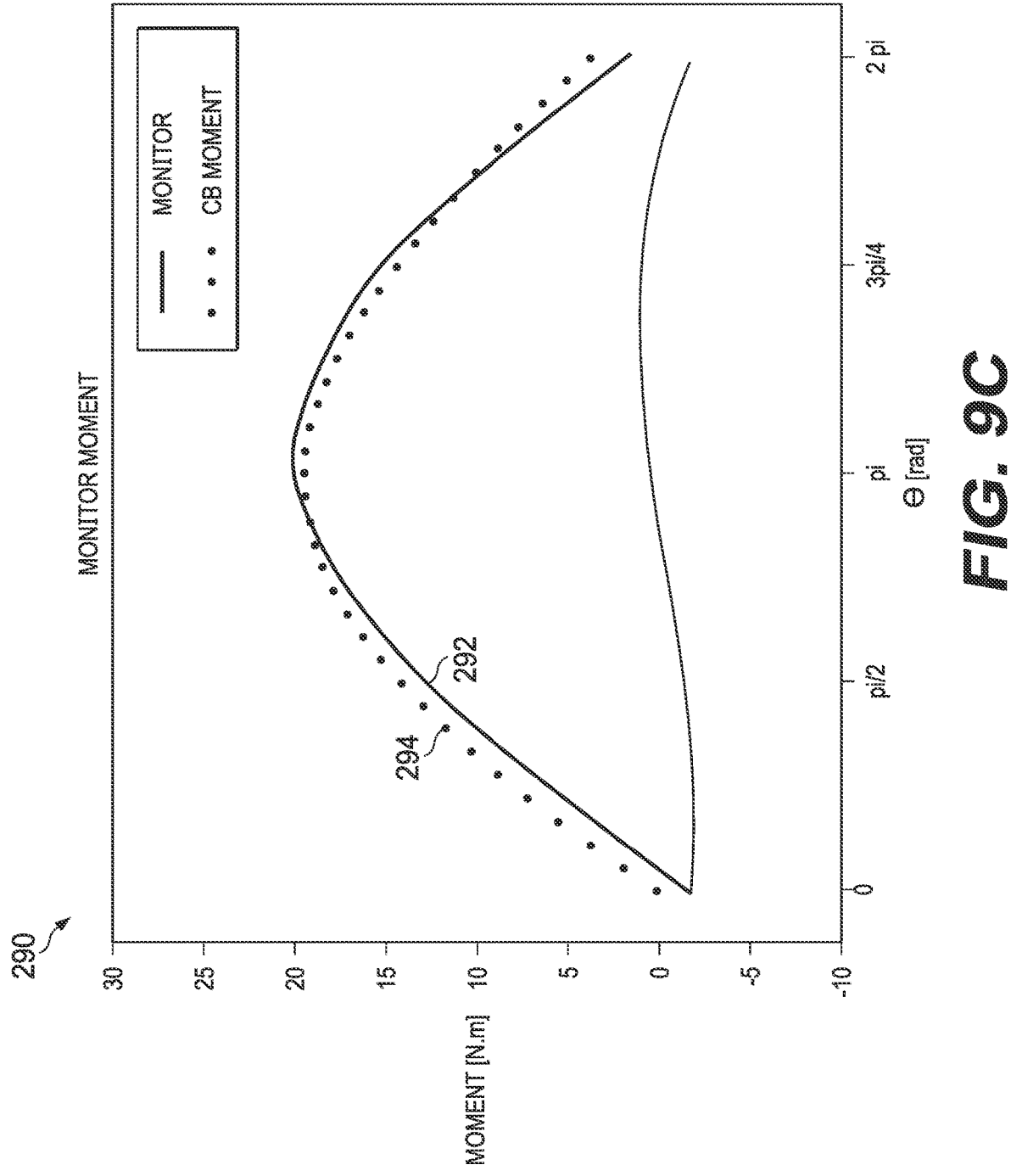
FIG. 9C is a graphical illustration of an applied moment and a counterbalance moment at various rotational positions of a monitor of a display system according to some embodiments.

FIG. 9C is a graphical illustration of an applied moment and a counterbalance moment at various rotational positions of the monitor 216a according to some embodiments. In some examples, when the monitors 216a, 216b transition from the closed configuration to an open configuration (which may be a partially open or fully open configuration), the monitor 216a rotates away from the monitor 216b, applying a varying degree of torque at the hinge mechanism 217 as the monitor 216a is rotated. In some embodiments, the applied torque at a point of rotation (e.g., the hinge mechanism 217) from the weight of the monitor 216a can be graphed as a half sine wave with increasing moment from a rotation angle of 0 degrees to a rotation angle of 90 degrees with the maximum moment at approximately 90 degrees. As the monitor 216a is further rotated from 90 degrees to 180 degrees, the moment continues to follow the sine wave, decreasing from the maximum moment to a minimum moment (e.g., 0 newton-meters). Thus, a counterbalance torque, provided by a counterbalance system (e.g., the counterbalance system 250), is required to follow a substantially similar sinusoidal graph of the applied monitor torque. In the embodiment of FIG. 9C, a graph 290 illustrates the applied moment at various rotational positions of the monitor 216a as a solid curve 292. The graph 290 further illustrates the required counterbalance moment at various rotational positions of the monitor 216a as a dotted curve 294.

Thus, in several embodiments, the required counterbalance force (e.g., a counterbalance torque) provided by the counterbalance system 250 is generally low when the monitor 216a first begins to rotate away from the monitor 216b from the closed configuration. As the monitor 216a continues to rotate away from the monitor 216b, the required counterbalance force increases. In some examples, the required counterbalance force reaches a maximum amount when the monitor 216a has rotated 90 degrees away from the monitor 216b. As the monitor 216a continues to rotate away from the monitor 216b (e.g., more than 90 degrees of rotation), the required counterbalance force begins to decrease from the maximum amount. When the monitor 216a rotates 180 degrees from the monitor 216b, the monitors 216a, 216b may be in a fully open configuration and the required counterbalance force is generally low. Therefore, the required counterbalance force transitions from a generally low force when the monitors 216a, 216b are in the closed configuration, to a maximum force when the monitor 216a has rotated 90 degrees relative to the monitor 216b, and then back to a generally low force when the monitors 216a, 216b are in the fully open configuration. In several embodiments, the transition of the required counterbalance force discussed above applies in the same manner when the monitors 216a, 216b are rotated from the fully open configuration to the closed configuration.

In some embodiments, the geometry and the sinusoidal nature of the counterbalance system 250 results in bias of the monitor 216a towards an open or closed configuration in a manner that the bias is greater as the monitor is closer to the open or closed configuration. In some examples, as illustrated in FIG. 9C, the counterbalance system 250 can be configured to provide a slightly higher counterbalance torque when closer to a fully closed (e.g., 0 degree) configuration and a fully open (e.g., 180 degree) configuration.

Thus, when at a configuration near a fully closed configuration, the counterbalance system 250 biases the monitor 216a towards a fully closed configuration. Furthermore, when at a near fully open configuration, the counterbalance system 250 biases the monitor 216a towards a fully open configuration. This provides assistance to an operator when the operator is attempting to open the monitor 216a and assistance to the operator when the operator is attempting to close the monitor 216a. The monitor 216a is also biased towards a fully closed configuration, which prevents undesired motion of the monitor 216a when the monitor 216a is unintentionally placed in a near fully closed configuration and prevents sagging of the monitor 216a when the monitor 216a is placed in a near fully open configuration. In other examples, when the monitor 216a is near a fully closed configuration, the counterbalance torque may be less than the monitor torque. In such examples, a net torque between the display system 216 and the counterbalance system 250 may bias the monitor 216a towards the fully closed configuration. In still other examples, when the monitor 216a is near a fully open configuration, the counterbalance torque may be higher than the monitor torque. In such examples, the net torque between the display system 216 and the counterbalance system 250 may bias the monitor 216a towards the fully open configuration.

In another embodiment, the monitor 216a can be rotated beyond 180 degrees and positioned in a mirrored fully closed configuration at 360 degrees or substantially close to 360 degrees. The applied torque of the monitor 216a and required counterbalance torque can be graphed as a half sine wave curve similar to the curve illustrated in FIG. 9C where maximum torque occurs at a rotational position of 270 degrees and minimum applied/required torques occur at 180 and 360 degrees.

In several embodiments, to apply the counterbalance force, the cable 253, coupled to the hinge connector 257, is pulled by the hinge connector 257 and consequently pulls the spring termination 252 in a direction L1 towards the proximal portion 258 of the spring 251, which compresses the spring 251. As the cable 253 is pulled in a direction L1, a compressive force is applied to the spring 251 by the spring termination 252. As the spring 251 is compressed, it provides an opposite force in the direction L2, creating a tension in the cable 253. The tensile force in the cable 253 generated by the reactive force of the compressed spring 251 at least partially counteracts the force from the weight of the monitor 216a to allow for a soft close or to otherwise prevent the monitor 216a from rotating quickly about the hinge mechanism 217 and falling on to the monitor 216b. When the display system 216 is in the closed configuration, the spring 251 is in a maximal compressed state, with greater compression than when the display system 216 is in the open or partially open configuration. In the maximal compressed state, the spring 251 may or may not be fully compressed.

Figure 11:
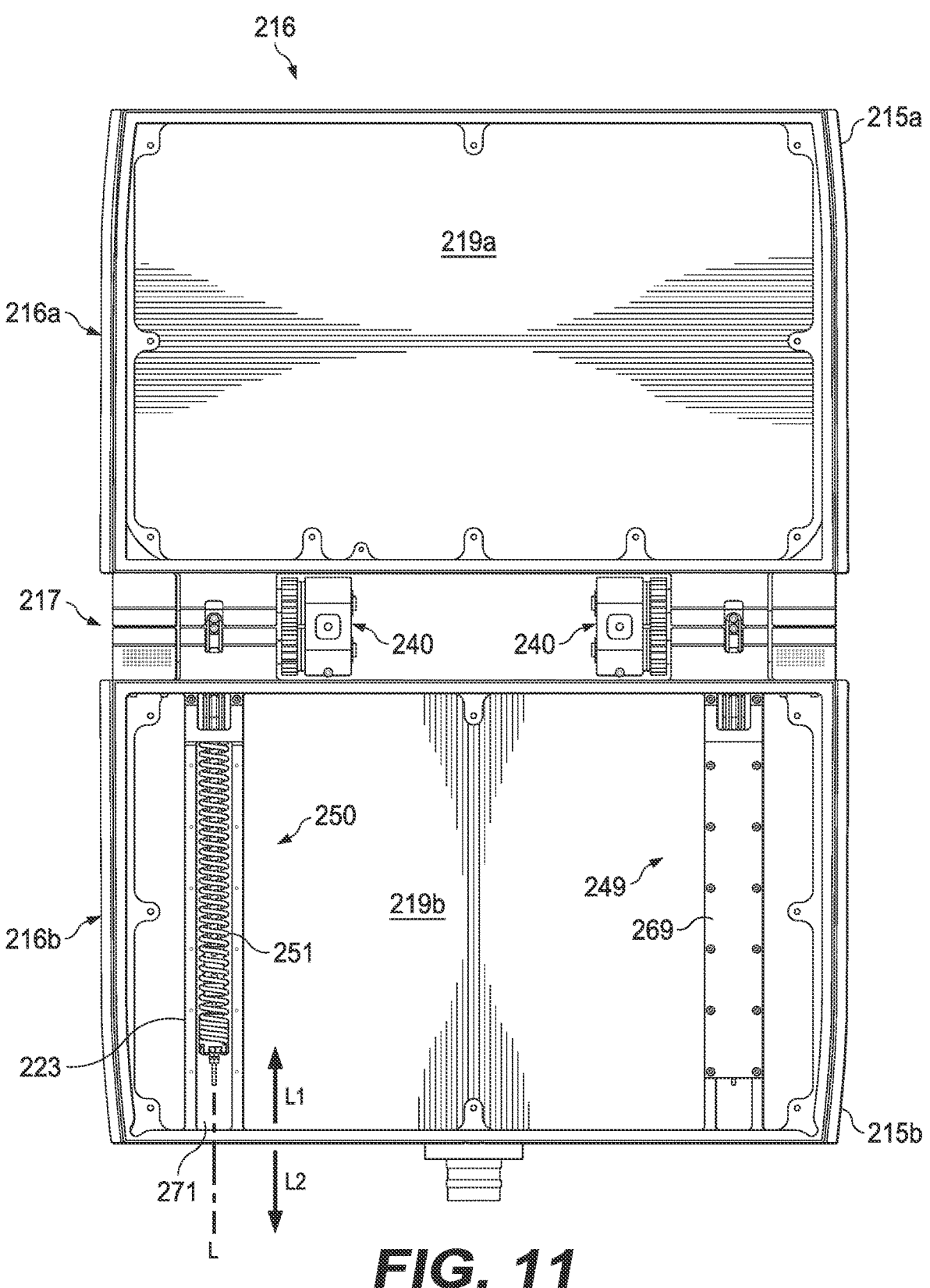
FIG. 11 illustrates various aspects of a counterbalance system when a display system is in an open configuration according to some embodiments.

FIG. 10 illustrates the display system 216 in a partially open configuration, and FIG. 11 illustrates the display system 216 in a fully open configuration. In both FIGS. 10 and 11, the display screen 221 is cut away so that the counterbalance systems 249, 250 are visible. As the display system 216 is moved into the partially open configuration from the closed configuration, the hinge connector 257 rotates with the monitor 216a, relative to the monitor 216b, and toward the pulley 256. The cable 253, coupled to the hinge connector 257, is carried by the hinge connector 257 and consequently begins releasing the tension placed on the spring termination 252 by moving the spring termination in the direction L2 along the axis L. The spring 251, biased toward an uncompressed or relaxed state, begins to uncompress as the movement of the cable 253 causes the spring termination 252 to move in the direction L2 along the axis L. As the spring termination 252 moves in the direction L2, the spring 251 begins to uncompress. Thus, as the monitor 216a rotates about the hinge mechanism 217, the spring 251 provides a force (which may also be a torque) to assist with overcoming the friction force in the hinge mechanism 217 and the force (which may also be a torque) from the weight of the monitor 216a, as the display system 216 moves into an open or partially open configuration. As discussed above, in several embodiments, the counterbalance system 250 provides a biasing force on the monitors 216a, 216b such that when the display system 216 is moved to the open or partially open configuration from the closed configuration, the monitors 216a, 216b are biased to open and move to the open or partially open configuration. In alternative embodiments, the counterbalance system 250 provides a biasing force on the monitors 216a, 216b such that when the display system 216 is moved to the partially open or closed configuration from the fully open configuration, the monitors 216a, 216b are biased to close and move to the partially open or closed configuration.

When the display system 216 is in the partially open configuration, the spring 251 is in a partially compressed state which is less compressed than when the display system 216 is in the closed configuration and more compressed than when the display system 216 is in the fully open configuration. When the display system 216 is in the fully open configuration, the spring 251 is in a minimal compressed state which is a less compressed state than when the display system 216 is in the closed configuration or the partially open configuration. In some embodiments, the spring 251 may be fully uncompressed or relaxed in the minimal compressed state, when the display system 216 is in the fully open configuration. Alternatively, due to pretension in the spring 251 for example, the spring 251 may maintain some amount of compression in the minimal compressed state when the display system 216 is in the fully open configuration.

As shown in FIG. 11, the counterbalance system 250 may be positioned within a channel 271 bounded by the back panel 219b and the rails 223. The channel 271 may be further bounded by a cover plate similar to the cover plate 269 shown covering the counterbalance system 249 according to some embodiments. The surfaces of the back panel 219b, the rails 223, and the cover plate that bound the channel 271 are the channel surface 270. In this embodiment, the channel 271 may form a rectangular prism. In some embodiments, the channel 271 may be formed by a cylindrical surface. The channel 271 may be any other suitable shape that accommodates the counterbalance system 250.

Figure 12:
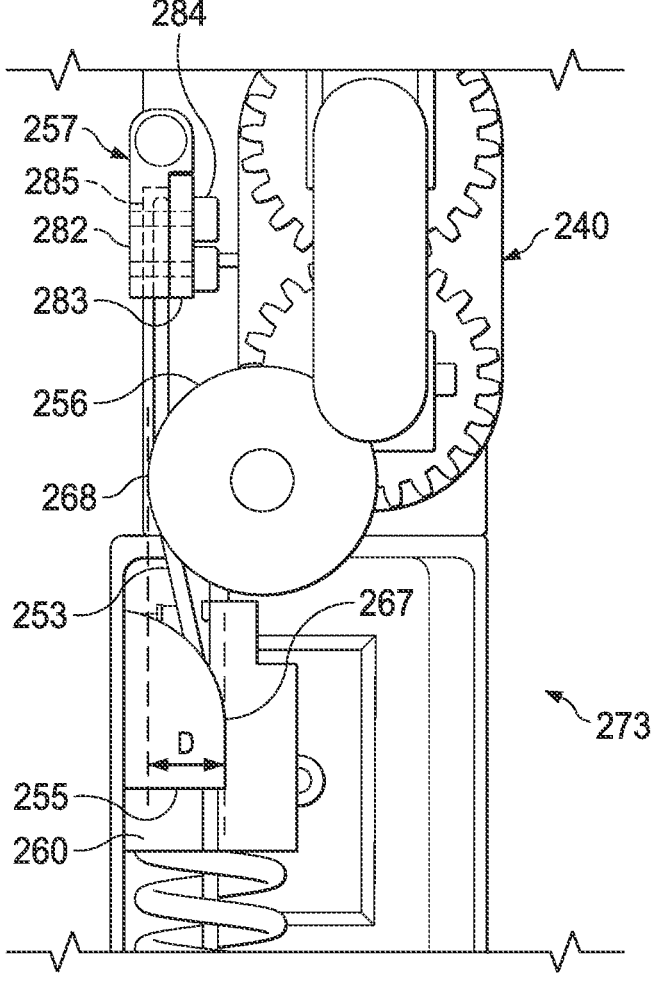
FIG. 12 illustrates a side view of a proximal end of a counterbalance assembly according to some embodiments.

FIG. 12 illustrates a side view of a proximal portion 273 of the counterbalance system 250 when the monitors 216a, 216b are in the fully open configuration according to some embodiments. The sector pulley 255 is positioned such that a leading edge 267 of the sector pulley 255 is offset by the distance D from a leading edge 268 of the pulley 256. This offset distance D allows the cable 253 to be tangent to the pulley 256 while the cable 253 is also substantially aligned with the longitudinal axis of the spring 251. The pulley 256 may also rotate relative to the housing 215b to help reduce friction on the tensioned cable 253, which can increase the life of the cable 253. In some embodiments, the hinge connector 257 includes a body portion 282, a cover 283, and at least one fastening member 284 (e.g., a screw) to couple the cover 283 to the body portion 282. During assembly of the display system 216, the cable 253 is positioned within a loop-shaped channel 285 in the body portion 282 and is held in place by the cover 283 and the fastening member 284.

As described above, the display system 216 may have a static force contributed by friction in the gear hinge assemblies 240 and a dynamic force contributed by the force from the spring 251 on the cable 253. As discussed above, the force provided by the counterbalance system 250 may be a counterbalance torque. Thus, the dynamic force may be a dynamic torque. The static and dynamic forces may be optimized to counterbalance the weight of the monitor 216a. The dynamic force contributed by the spring 251 may be selected based on the rate of the spring 251 and/or the pretension (e.g., a preload) in the spring 251. In some embodiments, the pretension in the spring 251 is resisted by the cable 253. FIGS. 13A-D illustrate a distal portion 276 of the counterbalance system 250 including a cable mount 266, the spring termination 252, and a preload adjustment assembly 254. The cable mount 266 includes a body portion 277, a cover 278, and at least one fastening member 279, such as a screw, to couple the cover 278 to the body portion 277. As shown in FIG. 13C, end portions 265a, 265b of the cable 253 include terminal members 288. The terminal members 288 may be attached (e.g., by crimping or soldering) or may be integrally formed with the end portions 265a, 265b. The terminal members 288 may be sized to fit within recesses 289 in the body portion 277. When the cover 278 is attached to the body portion 277 by the fastening member 279, the terminal members 288 may be captured between the body portion 277 and the cover 278 to prevent movement of the terminal members 288 relative to the body portion 277 when the cable 253 is subjected to a tensile load. In alternative embodiments, the cable 253 may be attached to the cable mount 266 with other types of fasteners including mechanical fasteners, solder, adhesives, or the like. In some embodiments, the cable 253 may extend through the body portion 277 of the cable mount 266. In some embodiments, the cable mount 266 may be a generally cylindrical shape. Such a shape may allow for the cable mount 266 to more easily travel within the spring 251. In alternative embodiments, the cable mount 266 may be a rectangular shape, a conical shape, or any other suitable shape. In alternative embodiments, the end portions 265a, 265b of the cable 253 may be coupled directly to the spring termination 252 or directly to the preload adjustment assembly 254.

Figure 13A:
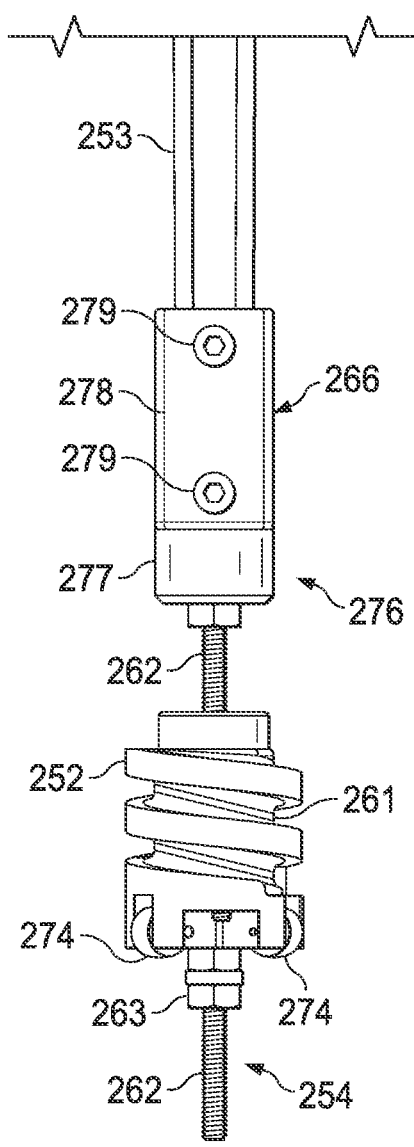
FIGS. 13A-13D illustrate various aspects of a distal end of a counterbalance assembly according to some embodiments.
Figure 13B:
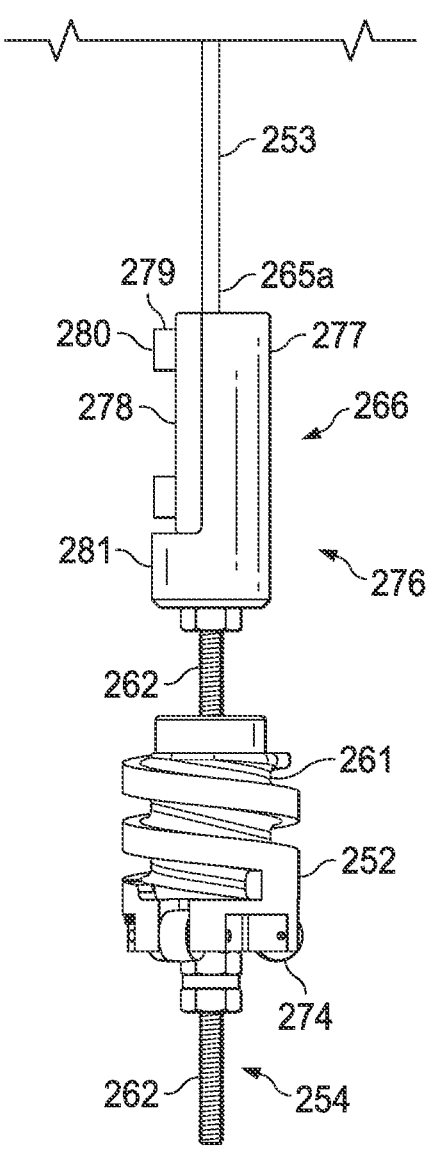
Figure 13C:
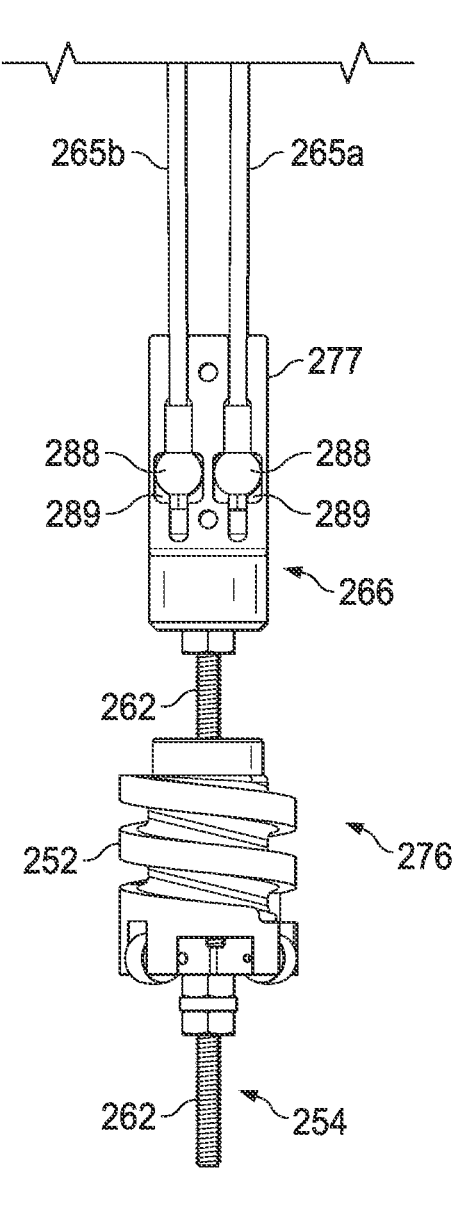

As shown in the embodiment of FIG. 13B, a back face 280 of each of the screws 279 terminates in a same plane as an outer surface 281 of the body portion 277 of the cable mount 266. This alignment may allow for the cable mount 266 to more easily travel within the spring 251. In alternative embodiments, the back face 280 of each of the screws 279 terminates in a different plane than the plane in which the outer surface 281 of the body portion 277 terminates. As one example, the back face 280 of each of the screws 279 may terminate in plane that is closer to the cover 278 than the plane in which the outer surface 281 of the body portion 277 terminates. As another example, the back face 280 of each of the screws 279 may terminate in plane that is farther from the cover 278 than the plane in which the outer surface 281 of the body portion 277 terminates.

Figure 13D:
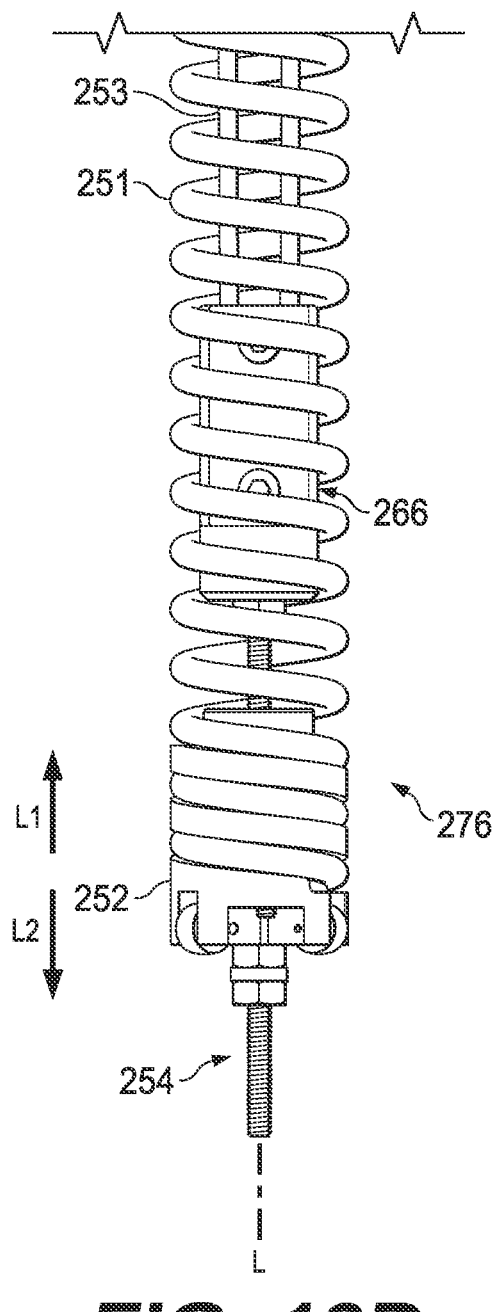

A threaded rod 262 (which may be referred to as an elongate member) is coupled to and extends from the body portion 277 of the cable mount 266 in a direction opposite of the cable 253. The spring termination 252 is mounted to the threaded rod 262. For example, the spring termination 252 may be threadedly coupled to the threaded rod 262 such that the position of the spring termination 252 may be adjusted by being rotated up or down the threaded rod 262. The spring termination 252 may be adjusted to alter pretension in the spring 251 to account for tolerances in length of the spring and/or cable, as well as to allow for adjustments to the rate of the spring 251. The spring termination 252 includes a helical groove 261. The helical groove 261 may be sized and shaped to receive the spring 251 as shown in FIG. 13D. The spring 251 may be coupled to the spring termination 252 at any rotational position within the helical groove 261 depending on the desired rate of the spring 251 to optimize the dynamic force from the spring. The desired rate of the spring 251 may be different depending on the size and weight of the monitor 216a, for example. Additionally, in some embodiments, once the spring 251 is coupled to the spring termination 252, the spring termination 252 may be rotated to further adjust the rate of the spring 251. Such adjustments may be made to fine tune the rate of the spring 251, which may be necessary when the specifications of a stock spring, for example, do not match with the desired specifications for the particular counterbalance system 250 in which the spring 251 is being used. In some embodiments, the distal portion 259 of the spring 251 may be coupled to the spring termination 252 with a mechanical connection, an adhesive connection, or any other suitable connection. In some embodiments, one counterbalance system (e.g., the counterbalance system 250) may be suited for one spring (e.g., the spring 251), and another counterbalance system may be suited for another spring depending on the components of the counterbalance assemblies.

The spring termination 252 includes a plurality of rollers 274. In some embodiments, the spring termination 252 includes two, three, four, or more than four rollers 274. The rollers 274 may be equidistantly spaced around the circumference of the spring termination 252. As one example, the spring termination 252 may include three rollers 274 each spaced 120 degrees apart around the circumference of the spring termination 252. As another example, the spring termination 252 may include two rollers 274 each spaced 180 degrees apart around the circumference of the spring termination 252. In some examples, the counterbalance system 250 may be positioned within the channel 271 and the rollers 274 of the spring termination 252 may contact the channel surface 270 and roll along the channel surface 270 as the spring termination 252 moves up and down when the monitor 216a is rotated relative to the monitor 216b to open or close the display system 216. The rollers 274 being in contact with the channel surface 270 may reduce friction and allow for more fluid movement of the spring termination 252 and of the counterbalance system 250 as a whole. The rollers 274 may also prevent the spring termination 252 and/or other components of the counterbalance system 250 from directly contacting the channel surface 270 as the components of the counterbalance system 250 change positions. This protects the components of the counterbalance system 250 and the channel surface 270 from unnecessary wear. In some embodiments, the spring 251 may buckle within channel 271 as the spring 251 moves up and down. Thus, the spring 251 may contact the channel surface 270. In such embodiments, the rollers 274 reduce friction between the spring 251 and the channel surface 270 as the spring 251 contacts the channel surface 270.

Pretension on the spring 251 may also contribute to the dynamic force provided by the spring 251. FIGS. 13A-D illustrates the preload adjustment assembly 254 which includes a distal portion of the threaded rod 262 and a coupling member such as the threaded nut 263. The threaded nut 263 is sized and shaped to threadedly couple with the threaded rod 262, and the threaded nut 263 is rotatable relative to the threaded rod 262. The preload adjustment assembly 254 may be used to adjust a tension on the spring 251, which is substantially the same as the tensile load provided to the cable 253, to account for different sizes and weights of the monitors 216a, 216b, for example. In this embodiment, the threaded nut 263 may be rotated relative to the threaded rod 262 to move the nut in a direction L1 or L2 to adjust the preload of the spring 251. Depending on the direction of rotation, such rotation may apply or remove tension from the spring 251 as desired. Such adjustments may be made to fine tune the preload of the spring 251, which may be necessary when the specifications of a stock spring, for example, do not match with the desired specifications for the particular counterbalance system 250. Additionally, the adjustments may be made to account for tolerances of the length of the spring 251 and/or the cable 253, as well as adjustments made to the rate of the spring 251 through rotation of the spring termination 252. In some embodiments, the adjustments to the spring 251 may be made to fine tune the force in the cable 253.

FIG. 13D illustrates a front view of the distal portion 272 of the counterbalance system 250. As discussed above, the cable mount 266 and the cable 253 are surrounded by the spring 251. This allows the cable 253 and cable mount 266 to travel up and down within the spring 251 as the monitors 216a, 216b rotate relative to one another. Such a compact configuration for the counterbalance system 250 can help save space within the monitor 216b, which may help reduce production costs and may help reduce the overall size and weight of the upper and lower monitors 216a, 216b. Additionally, in embodiments where a longer spring may be needed, the spring 251 and the cable 253 may be positioned within the housing 215b at any angle to help reduce the size of the upper and lower monitors 216a, 216b. For example, the spring 251 and the cable 253 may be positioned at an angle relative to a wall of the housing 215b. The spring 251 and the cable 253 may also be positioned horizontally within the housing 215b. In some embodiments, the spring 251 may be an extension spring. This may allow the length of the spring 251 to be increased, as needed.

Figure 14:
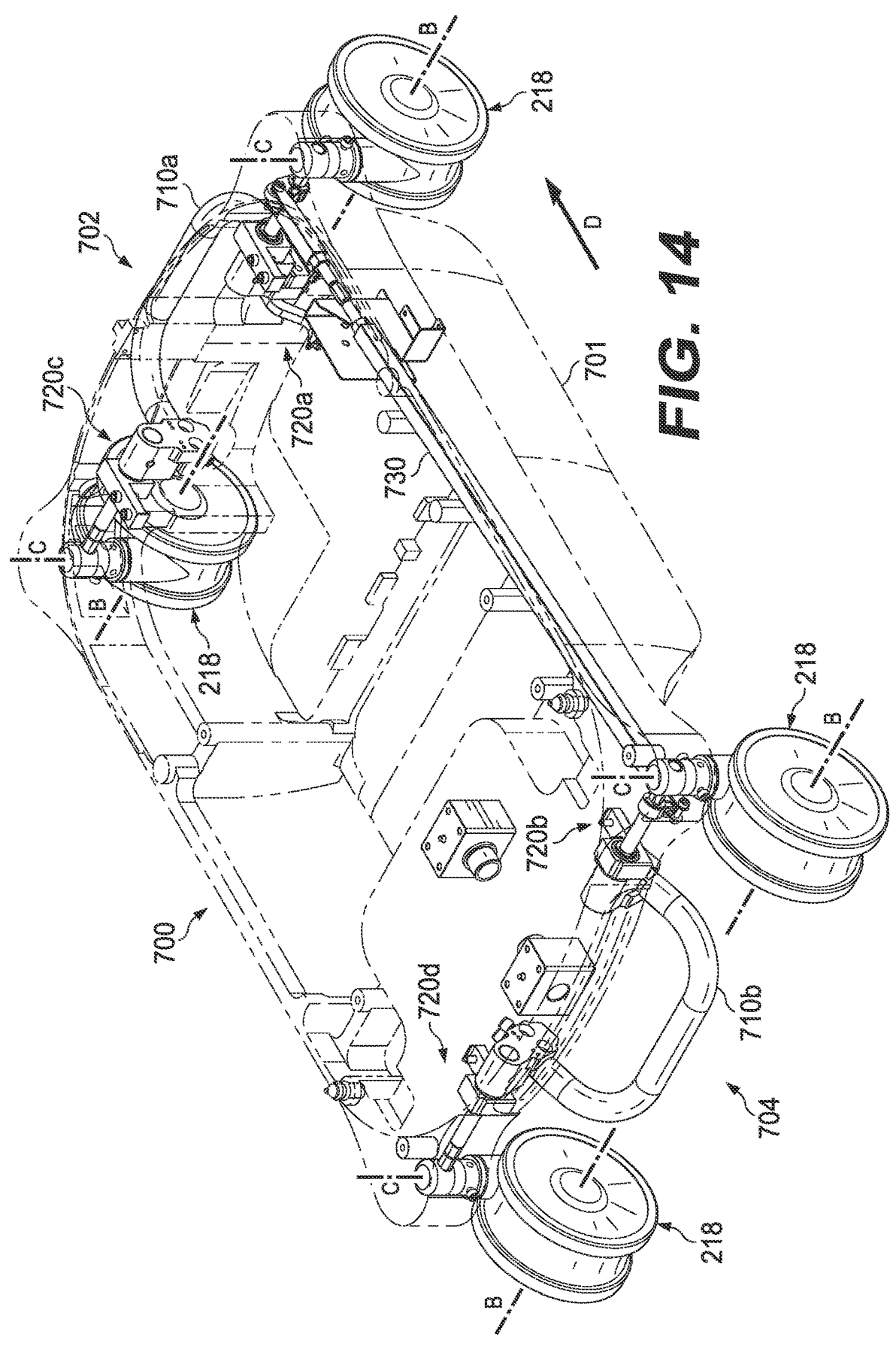
FIG. 14 illustrates various aspects of a brake assembly of a system cart according to some embodiments.

With reference to FIG. 2, the system cart 214 is mounted on a set of wheels 218 (also referred to as wheel assemblies). The cart 214 may have an unbraked configuration in which the cart 214 may be movable to a desired location relative to an operating table (e.g., operating table T) and a patient (e.g., patient P). In the unbraked configuration, the wheels 218 may be rotatable about an axis B parallel to the ground and/or pivotable, about an axis C perpendicular to the ground, allowing translational and rotational movement of the cart 214. The cart 214 may also have a braked configuration in which the wheels 218, and therefore the cart 214, are locked so that rotational and pivoting movement is restricted, and the cart 214 remains in a stationary position. FIG. 14 illustrates a cart base 700 of the cart 214. The cart base 700 is coupled to the wheel assemblies 218 and includes a front end 702 and a back end 704. In this embodiment, the cart base 700 includes a housing 701, two pedals 710a, 710b and brake assemblies 720a-720d corresponding to each wheel assembly 218. The brake assemblies 720b and 720d correspond to the pedal 710b and are located at the back end 704 of the cart base 700. The brake assemblies 720a and 720c correspond to the pedal 710a and are located at the front end 702 of the cart base 700. As seen in FIG. 14, each wheel assembly 218 may be rotatable about its own axis B parallel to the ground and/or may be pivotable about its own axis C perpendicular to the ground, allowing translational and rotational movement of the cart 214.

Figure 15A:
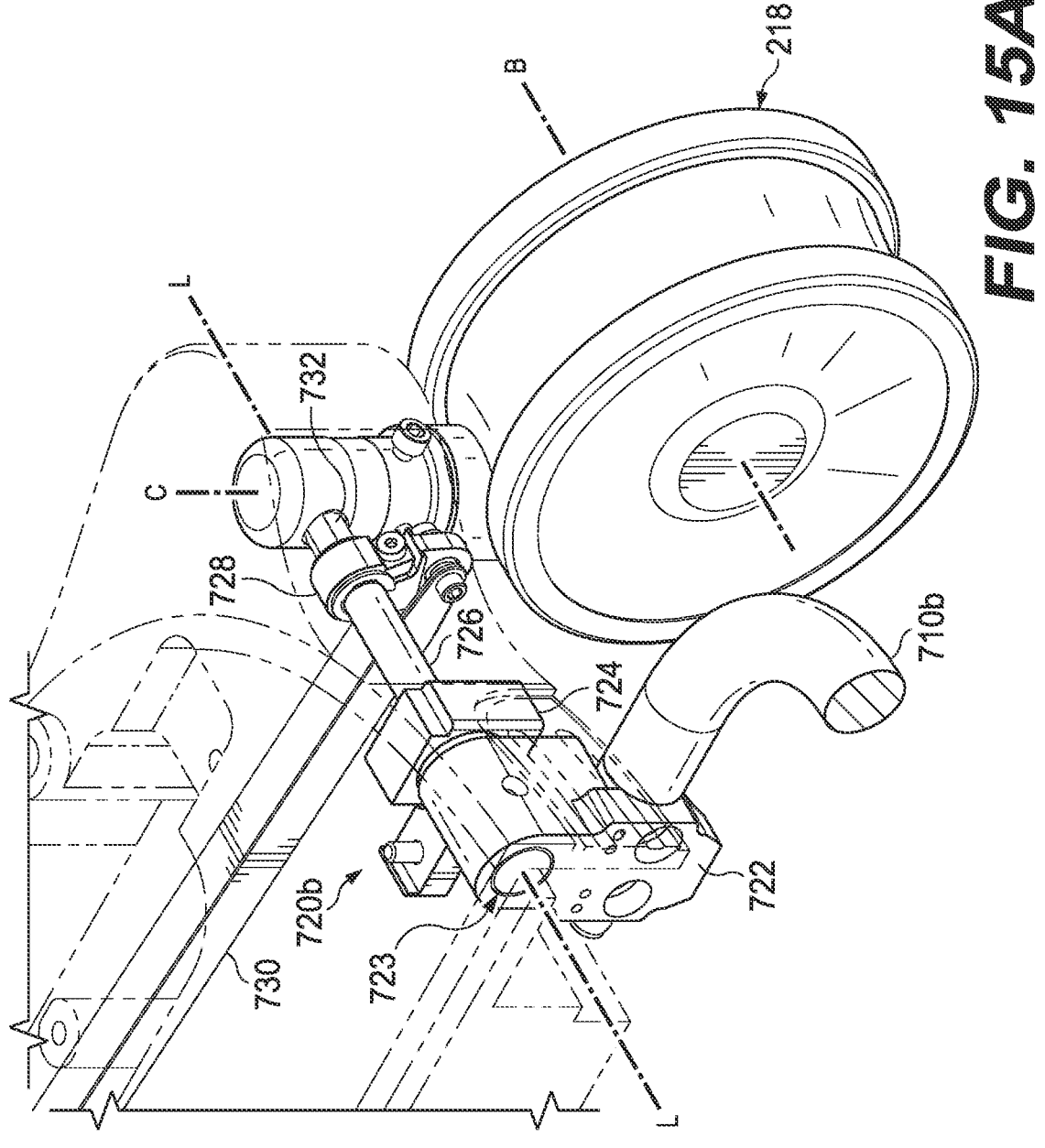
FIG. 15A illustrates various aspects of a brake assembly in an unbraked configuration according to some embodiments.

FIG. 15A illustrates the brake assembly 720*b* corresponding to one of the wheel assemblies 218 at the back end 704 of the cart base 700. While the following discussion refers to a single brake assembly 720*b* corresponding to a single wheel assembly 218, it is to be understood that this discussion may apply to other brake assemblies that may be present in the cart base 700. As shown in FIG. 15A, the brake assembly 720*b* is in an unbraked configuration. Thus, the cart 214 may be movable to a desired location relative to the operating table T and the patient P. In the unbraked configuration, the pedal 710*b* is not depressed.

As shown in the embodiment of FIG. 15A, the brake assembly 720*b* may include a pedal connector 722 mechanically coupled to the pedal 710*b*. In some embodiments, the pedal connector 722 is integrally formed with the pedal 710*b*. In other embodiments, the pedal connector 722 is removably coupled to the pedal 710*b*. The brake assembly 720*b* may further include a stabilizing member 724 rigidly coupled to or integrally formed with the cart base housing 701. As shown in FIG. 15A, the brake assembly may further include a shaft 726 extending along a longitudinal axis L. In this embodiment, the shaft 726 extends through a passage 723 in the pedal connector 722 and a passage (not shown) in the stabilizing member 724. The shaft 726 may be fixedly coupled to the pedal connector 722 such that when the pedal connector pivots about the longitudinal axis L of the shaft 726, the shaft 726 also rotates about its longitudinal axis L. The shaft 726 extends through and rotates relative to the stabilizing member 724 but remains translationally fixed relative to the base housing 701 by the stabilizing member 724.

In this embodiment, the brake assembly 720*b* further includes a coupling member 728 fixedly coupled at one end to the shaft 726 and rotatably coupled at another end to a synchronization shaft 730 that extends to the brake assembly 720*a* at the front end 702 of the cart base 700. The brake assembly 720*b* further includes a shaft 732 fixedly coupled at one end to the coupling member 728 and rotatably coupled at another end to the wheel assembly 218. The shaft 732 may be integrally formed with the shaft 726 or may be connected to the shaft 726 by the coupling member 728 so that rotational motion of the shaft 726 about the longitudinal axis L causes rotational motion of the shaft 732 about the longitudinal axis L.

Figure 15B:
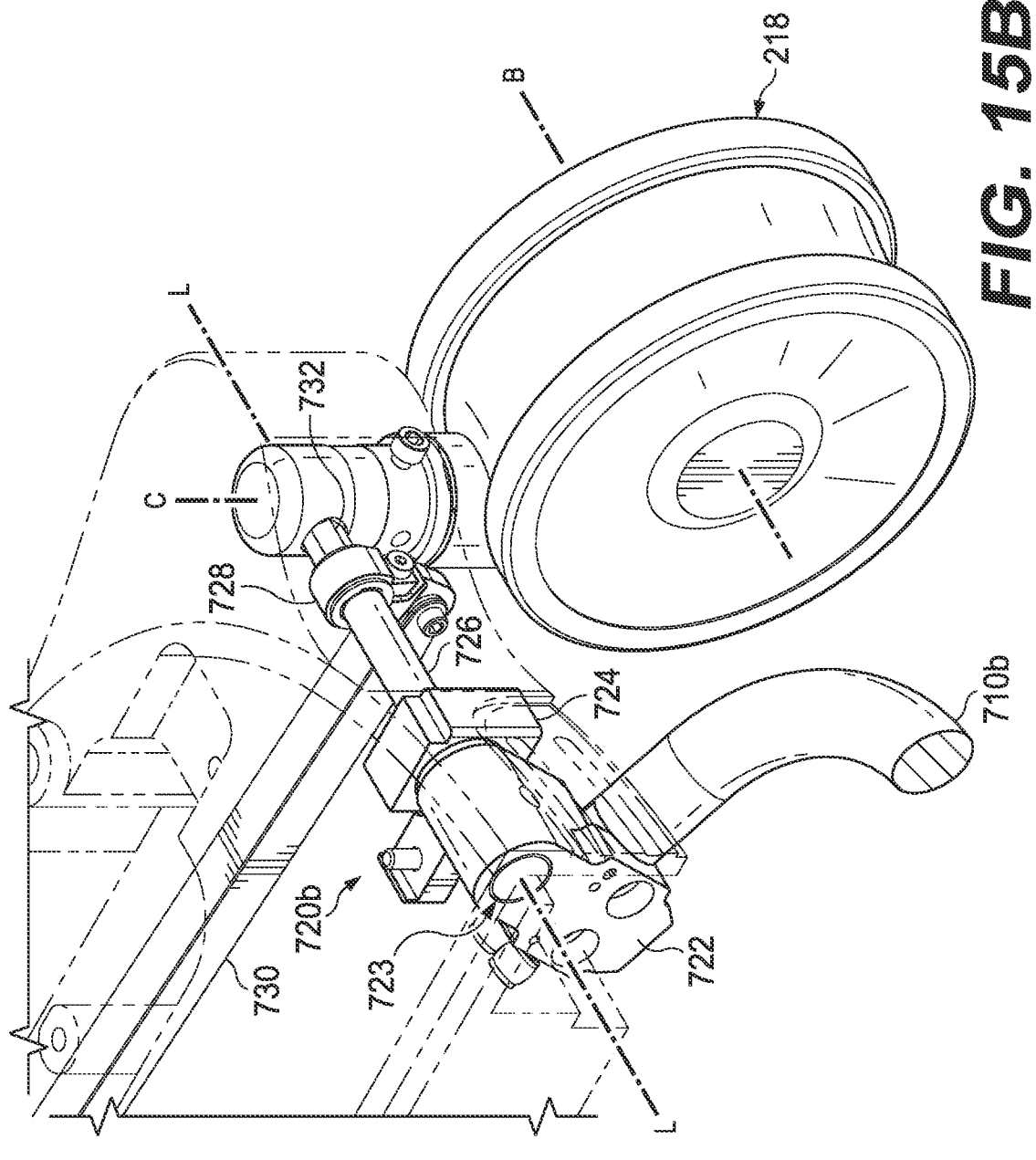
FIG. 15B illustrates various aspects of a brake assembly in a braked configuration according to some embodiments.

To transition the brake assembly 720*b* from the unbraked configuration to the braked configuration, an operator depresses (e.g., steps on) one of the pedals 710*a*, 710*b*. The following discussion will be made with reference to the pedal 710*b*. It is to be understood that this discussion also applies to the pedal 710*a*. When the pedal 710*b* is depressed, the pedal 710*b* moves in a downward direction. In this embodiment, when the pedal 710*b* is depressed, the pedal connector 722 pivots about the longitudinal axis L, causing rotation of the shaft 726. Rotation of the shaft 726 causes the coupling member 728 and the shaft 732 to rotate about the longitudinal axis L. In this embodiment, rotation of the shaft 732 engages a braking mechanism within the wheel assembly 218, causing the wheel assembly 218 to be braked and thereby preventing rotation of the wheel assembly 218 about axis B (e.g., wheel rotation) and/or axis C (e.g., wheel swivel). Rotation of the coupling member 728 also causes translational motion of the synchronization shaft 730, causing a corresponding braking action at the connected brake assembly 720*b* at the front end 702 of the cart base 700. FIG. 15B shows the brake assembly 720*b* in a braked configuration with the wheel assemblies 218 locked to prevent rotation about the axes B and/or C. Thus, the cart 214 remains in a stationary position.

In some embodiments, the pedals 710*a*, 710*b* are mechanically synchronized. Because the pedals 710*a*, 710*b* are coupled to the brake assemblies 720*a*-720*d*, all of the brake assemblies 720*a*-720*d* of the cart 214 are also mechanically synchronized. Thus, depressing one of the pedals 710*a* or 710*b* causes all of the brake assemblies 720*a*-720*d* to become engaged, which causes the wheel assemblies 218 to be braked, thereby preventing movement of all the wheel assemblies 218. In this embodiment, when the pedal 710*b* is not depressed, the pedal 710*a* is also not depressed because the pedals 710*a*, 710*b* are mechanically synchronized. Therefore, when one pedal moves (either up or down), the other pedal correspondingly moves up or down in the same manner as the first pedal. This mechanical synchronization between the pedals 710*a*, 710*b* allows for an operator of the cart 214 to depress both pedals 710*a*, 710*b* (and thereby engage the brake assemblies 720*a*-720*b*) by only stepping on one pedal. In some examples, the synchronization shaft 730 provides for the mechanical synchronization between the pedals 710*a*, 710*b*. In some embodiments, as shown in FIG. 14, one end of the synchronization shaft 730 is rotatably coupled to the coupling member 728 of the brake assembly 720*b* corresponding to the wheel assembly 218 at the back end 704 of the cart base 700, and the other end of the synchronization shaft 730 is rotatably coupled to a coupling member 728 of a brake assembly 720*a* corresponding to a wheel assembly 218 at the front end 702 of the cart base 700. While the synchronization shaft 730 is shown as coupled to the brake assemblies 720*a* and 720*b* in FIG. 14, the synchronization shaft 730 may alternatively be coupled to the brake assemblies 720*c* and 720*d*.

In some embodiments, when the pedal 710*b* is depressed, the depression of the pedal 710*b* engages the brake assembly 720*b* and the brake assembly 720*d*. As discussed above, depression of the pedal 710*b* results in the coupling member 728 of each brake assembly 720*b*, 720*d* pivoting about the longitudinal axis L. When the coupling member 728 of the brake assembly 720*b* pivots about the longitudinal axis L, the coupling member 728 causes the synchronization shaft 730 to move in a direction D (see FIG. 14). The direction D may be generally perpendicular to the longitudinal axis L. When the synchronization shaft 730 moves in the direction D, the coupling member 728 of the brake assembly 720*a* correspondingly moves in the direction D because the coupling member 728 of the brake assembly 720*a* is rotatably coupled to the synchronization shaft 730. Additionally, the coupling member 728 of the brake assembly 720*a* pivots about the longitudinal axis L. The rotation of the coupling member 728 causes the shaft 732 of the brake assembly 720*a* to rotate, which causes the wheel assembly 218 corresponding to the brake assembly 720*a* at the front end 702 of the cart 204 to be braked. Additionally, the rotation of the coupling member 728 causes the shaft 726 of the brake assembly 720*a* to rotate about its own longitudinal axis L. The rotation of the shaft 726 results in pivoting of the pedal connector 722 of the brake assembly 720*a*, which then results in the pedal 710*a* becoming depressed. The depression of the pedal 710*a* engages the brake assembly 720*c*, which might not be directly coupled to the synchronization shaft 730. Accordingly, the depression of one pedal may cause all of the brake assemblies 720*a*-720*d* of the cart base 700 to become engaged. In this way, the brake assemblies 720*a*-720*d* are synchronized such that all of the brake assemblies 720*a*-720*d* may be engaged at the same time with a single pedal press.

In some embodiments, when the pedal 710*b*, for example, is depressed, the pedal 710*b* may be locked in the depressed position until the pedal 710*b* is actuated again. This further actuation may include an additional pedal press, or it may include pulling the pedal up. In alternative embodiments, the pedal 710*b*, for example, must be actively depressed to maintain engagement of the brake assemblies 720. For example, an operator must constantly hold the pedal 710*b* in the depressed state to ensure that the brake assemblies 720 remain engaged.

In other embodiments, the cart base 700 may include a single pedal. In further alternative embodiments, the cart base 700 may include one brake assembly 720 corresponding to a single one of the two wheel assemblies 218 at the front end 702 of the cart base 700 and one brake assembly 720 corresponding to a single one of the two wheel assemblies 218 at the back end 704 of the cart base 700. In still other embodiments, the cart base 700 may include brake assemblies on the front end 702 wheels of the cart base 700 and no brake assemblies on the back end 704 wheels. In other examples, the cart base 700 may include brake assemblies on the back end 704 wheels of the cart base 700 and no brake assemblies on the front end 702 wheels. Additionally, in some alternative embodiments, in the unbraked configuration, the pedal 710*b* is depressed.

Figure 16:
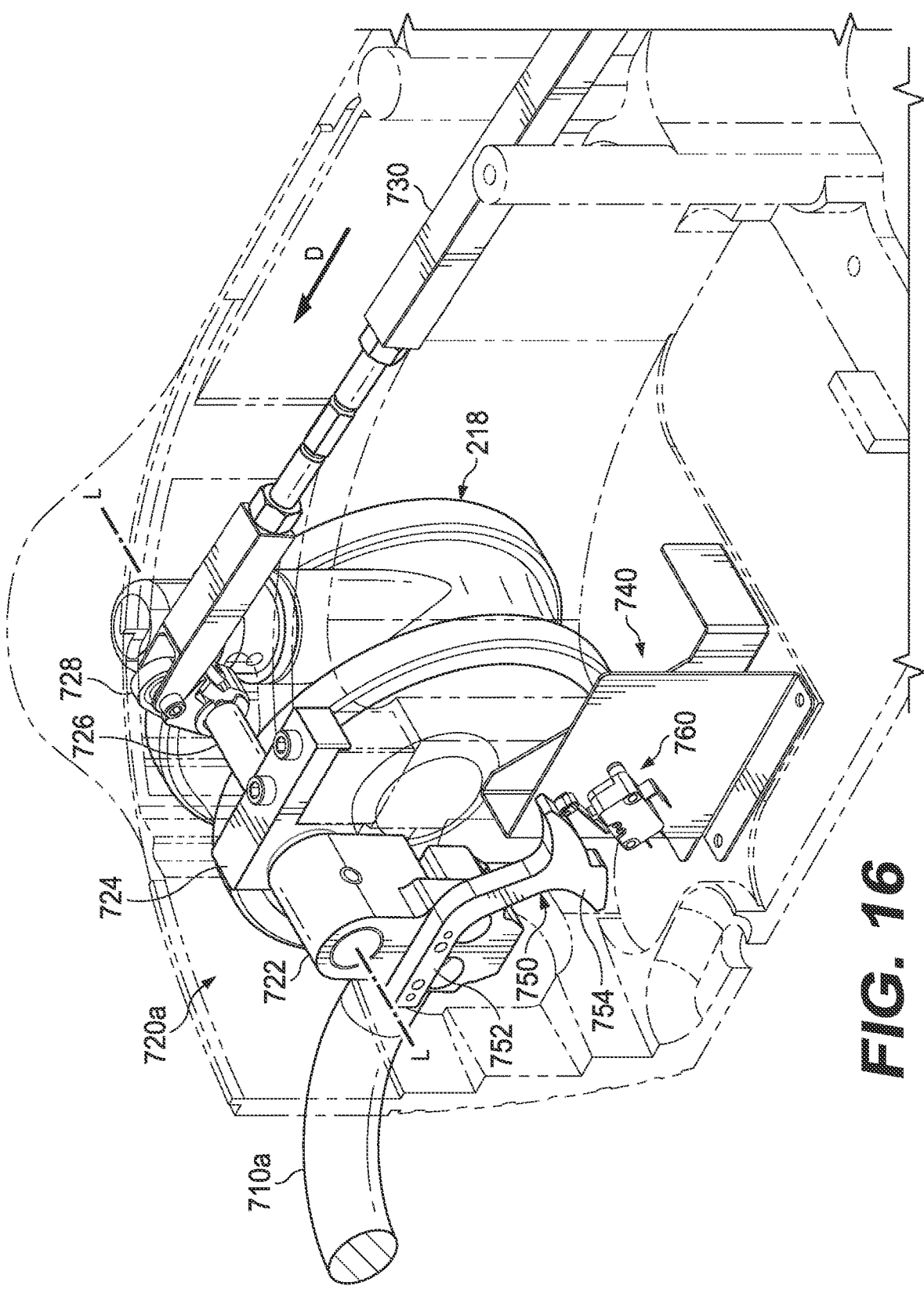
FIG. 16 illustrates various aspects of a brake assembly with a sensor assembly according to some embodiments.

FIG. 16 shows a brake assembly 720*a* corresponding to a wheel assembly 218 at the front end 702 of the cart base 700. The brake assembly 720*a* may include all the components of the brake assembly 720*b* discussed above with respect to FIGS. 15A-15B. The brake assembly 720*a* shown in the embodiment of FIG. 16 also includes a sensor assembly 740. In some embodiments, the sensor assembly 740 includes an activation member 750 and a brake sensor 760. In some embodiments, the brake sensor 760 includes a control system 762, a trigger 764, and a lever 766.

The activation member 750 includes a proximal portion 752 and a distal portion 754. The proximal portion 752 may be fixedly coupled to the pedal connector 722. Thus, when the pedal 710*a* is depressed and the pedal connector 722 rotates, the activation member 750 rotates as well. In some embodiments, the proximal portion 752 of the activation member 750 may be integrally formed with the pedal connector 722. In other embodiments, the proximal portion 752 of the activation member 750 may be removably coupled to the pedal connector 722. The distal portion 754 of the activation member 750 may contact the brake sensor 760. In the embodiment shown in FIG. 16, the brake assembly 720*a* includes the sensor assembly 740. In alternative embodiments, any one or more of the brake assemblies 720*a*-720*d* may include a sensor assembly 740.

Figure 17A:
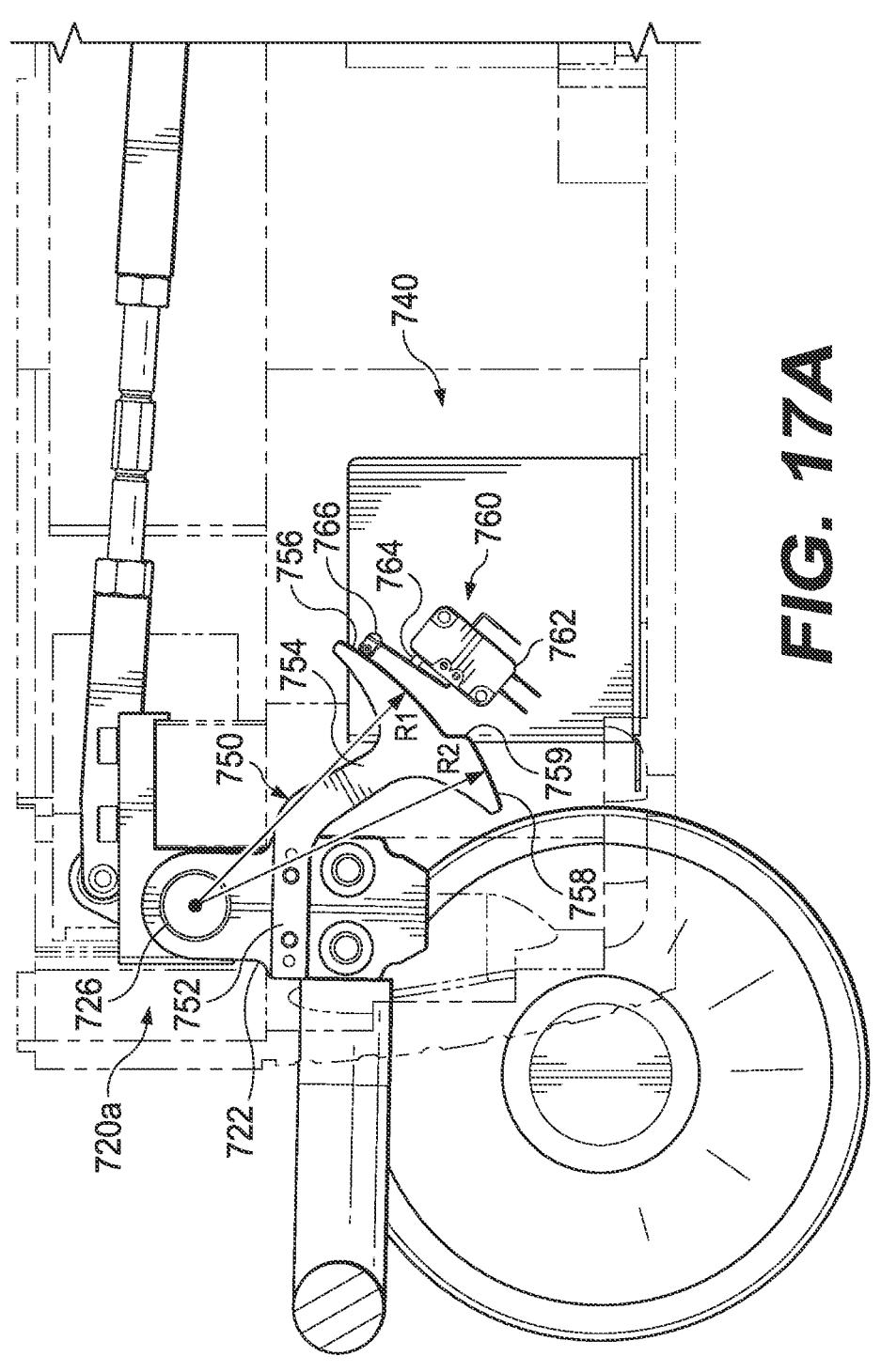
FIG. 17A illustrates various aspects of a brake assembly with a sensor assembly when the brake assembly is in an unbraked configuration according to some embodiments.

FIG. 17A is a side view of the brake assembly 720*a* and the sensor assembly 740 shown in FIG. 16. As shown in the embodiment of FIG. 17A, the distal portion 754 of the activation member 750 includes an upper portion 756 and a lower portion 758. The upper portion 756 and the lower portion 758 may be connected by a lip 759. In embodiments where the longitudinal axis L of the shaft 726 is the center point of a circle, as shown in FIG. 17A, the upper portion 756 of the distal portion 754 of the activation member 750 may include a length (e.g., radius R1), which indicates a distance between the longitudinal axis L and the upper portion 756. The lower portion 758 of the distal portion 754 of the activation member 750 may include a length (e.g., radius R2), which indicates a distance between the longitudinal axis L and the lower portion 758. As seen in the embodiment of FIG. 17A, the radius R2 is greater than the radius R1. Therefore, the lower portion 758 is farther from the longitudinal axis L than the upper portion 756. When the activation member 750 rotates (which may occur when the pedal 710*a* or 710*b* is depressed), the upper and lower portions 756, 758 of the distal portion 754 of the activation member 750 may each interact with the brake sensor 760.

Figure 17B:
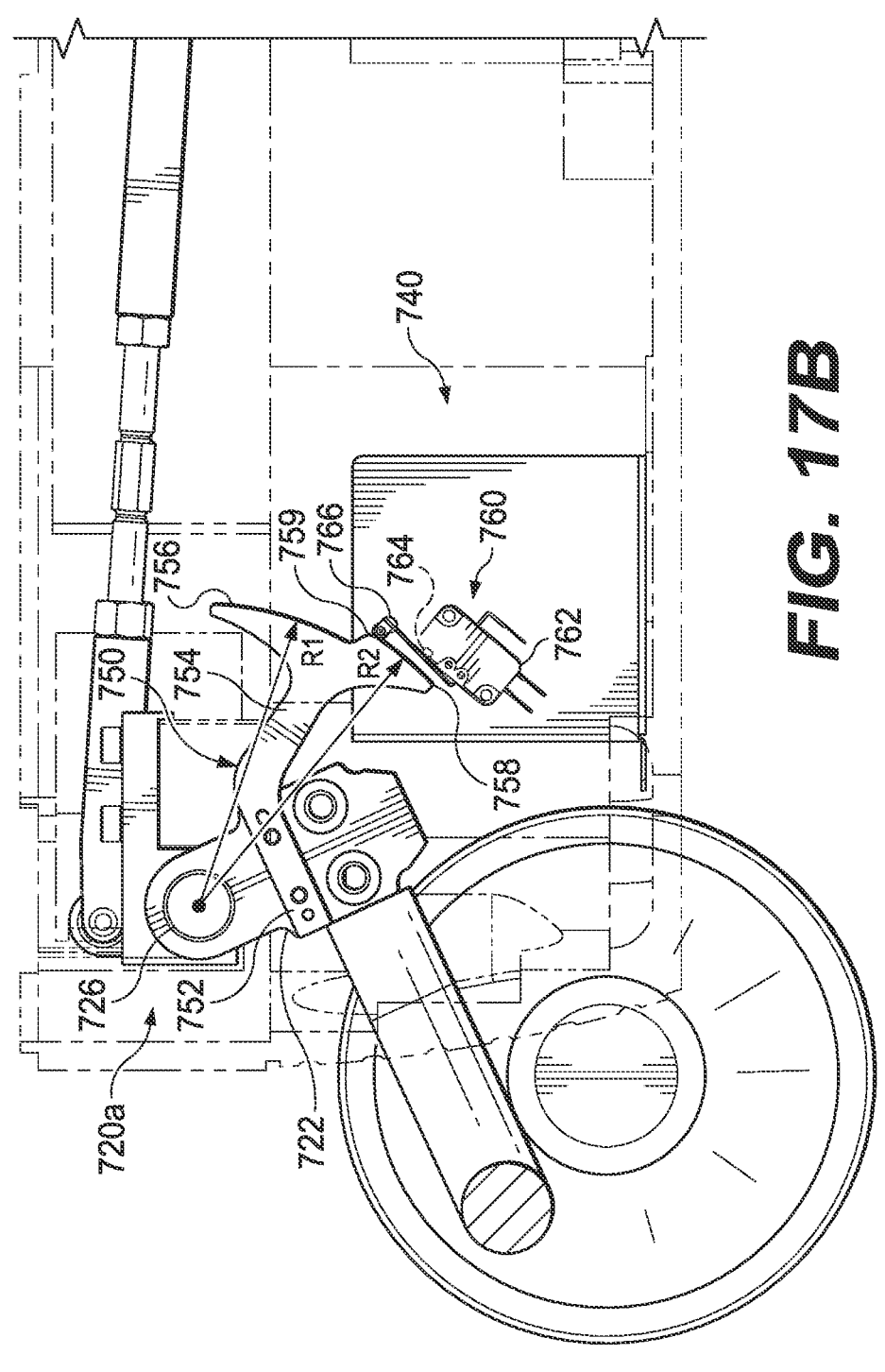
FIG. 17B illustrates various aspects of a brake assembly with a sensor assembly when the brake assembly is in a braked configuration according to some embodiments.

As shown in FIG. 17A, in the unbraked configuration, the lever 766 is in contact with the upper portion 756 of the distal portion 754 of the activation member 750. As the pedal 710*a* is depressed, the activation member 750 rotates. During the rotation, the lever 766 remains in contact with the upper portion 756 until the lip 759 contacts the lever 766. As the activation member 750 continues to rotate, the lever 766 travels over the lip 759 and comes into contact with the lower portion 758 of the distal portion 754. FIG. 17B shows the cart 214 in the braked configuration, which coincides with the lever 766 contacting the lower portion 758. As seen in the embodiment of FIG. 17B, when the lever 766 is in contact with the lower portion 758, the lever 766 moves toward the trigger 764, thereby depressing the trigger 764. This depression of the trigger 764 is a result of the radius R2 of the lower portion 758 being larger than the radius R1 of the upper portion 756. When the trigger 764 is depressed, the control system 762 then receives a signal that the cart 214 is braked. The control system 762 may then transmit that signal to the control system 112 to inform the control system 112 that the cart 214 is braked. After the control system 112 confirms that the cart 214 is braked, one or more operators (e.g., a surgeon, clinician, nurse, etc.) may proceed with the medical procedure to be performed on the patient P.

The discussion above with respect to FIGS. 17A-17B was made with reference to the upper portion 756 having a radius R1 and being in contact with the lever 766 when the cart is in the unbraked configuration. In alternative embodiments, the upper portion 756 may include the radius R2, and the lower portion 758 may include the radius R1. In such alternative embodiments, the control system 762 may determine that the cart 214 is in the unbraked configuration when the trigger 764 is depressed (e.g., when the lever 766 is in contact with the upper portion 756). As the activation member 750 rotates when the pedal 710*a* is depressed, the lever 766 remains in contact with the upper portion 756 until the lever 766 travels down the lip 759 and comes into contact with the lower portion 758, which includes radius R1. When the lever 766 travels down the lip from the upper portion 756 to the lower portion 758, the trigger 764 moves from a depressed state to a non-depressed state. When the trigger 764 is in the non-depressed state, the control system 762 may determine that the cart 214 is in the braked configuration. The control system 762 may then transmit a signal to the control system 112 indicating that the cart 214 is braked.

While certain illustrative embodiments of the invention have been described and shown in the accompanying drawings, it is to be understood that such embodiments are merely illustrative of and not restrictive on the broad invention, and that the embodiments of the invention not be limited to the specific constructions and arrangements shown and described, since various other modifications may occur to those ordinarily skilled in the art.

Various aspects of the subject matter described herein are set forth in the following numbered examples.

Example 1: A system comprises a hinged assembly including a first member coupled by a hinge to a second member; and a counterbalance assembly to counterbalance a weight of the first member as the first member rotates relative to the second member about the hinge, the counterbalance assembly comprising: a spring extending within the second member; a termination member coupled to the spring, the termination member configured to control a rate of the spring; a cable coupled to the termination member and to the hinge; and a preload adjustment assembly coupled to the cable and configured to control a preload of the spring.

Example 2: The system of example 1, wherein the termination member includes a helical groove, and wherein a configuration of the spring within the helical groove determines the rate of the spring.

Example 3: The system of example 1, wherein the preload adjustment assembly comprises: an elongate member extending through the termination member; and a coupling member configured to receive a rotational input relative to the elongate member to control the preload of the spring.

Example 4: The system of example 3, wherein the counterbalance assembly further comprises a cable mount, wherein the cable is coupled to the termination member via the cable mount.

Example 5: The system of example 4, wherein the elongate member is coupled to the cable mount.

Example 6: The system of example 1, wherein the counterbalance assembly further comprises a cable mount positioned between the cable and the termination member, the cable mount including a proximal portion and a distal portion.

Example 7: The system of example 6, wherein the cable is coupled to the proximal portion of the cable mount, and the preload adjustment assembly is coupled to the distal portion of the cable mount.

Example 8: The system of example 1, wherein the hinge comprises a gear hinge assembly.

Example 9: The system of example 8, wherein the gear hinge assembly comprises: a housing; a first gear mounted in the first member; and a second gear mounted in the second member, wherein the first gear is coupled to the second gear.

Example 10: The system of example 9, wherein the gear hinge assembly further comprises: a first friction member configured to contact the housing; a second friction member coupled to the first friction member; and a plurality of biasing members, wherein the plurality of biasing members biases the second friction member toward the first friction member to impart a friction force between the first friction member and the housing.

Example 11: The system of example 10, wherein the friction force is configured to facilitate manipulation of the first member and the second member.

Example 12: The system of example 10, wherein the friction force is configured to compensate for a difference between a counterbalance force provided by the counterbalance assembly and a force provided by the weight of the first member.

Example 13: A counterbalance system to counterbalance a weight of a first member as the first member rotates relative to a second member about a hinge, the counterbalance system comprising: a spring extending within the second member; a termination member coupled to the spring, the termination member configured to control a rate of the spring; a cable coupled to the termination member and to the hinge; and a preload adjustment assembly coupled to the cable and configured to control a preload of the spring.

Example 14: The counterbalance system of example 13, wherein the termination member includes a helical groove, and wherein a configuration of the spring within the helical groove determines the rate of the spring.

Example 15: The counterbalance system of example 13, wherein the preload adjustment assembly comprises: an elongate member extending through the termination member; and a coupling member configured to receive a rotational input relative to the elongate member to control the preload of the spring.

Example 16: The counterbalance system of example 15, wherein the counterbalance system further comprises a cable mount, wherein the cable is coupled to the termination member via the cable mount.

Example 17: The counterbalance system of example 16, wherein the elongate member is coupled to the cable mount.

Example 18: The counterbalance system of example 13, wherein the counterbalance system further comprises a cable mount positioned between the cable and the termination member, the cable mount including a proximal portion and a distal portion.

Example 19: The counterbalance system of example 18, wherein the cable is coupled to the proximal portion of the cable mount, and the preload adjustment assembly is coupled to the distal portion of the cable mount.

Example 20: The counterbalance system of example 13, wherein the hinge comprises a gear hinge assembly.

Example 21: The counterbalance system of example 20, wherein the gear hinge assembly comprises: a housing; a first gear mounted in the first member; and a second gear mounted in the second member, wherein the first gear is coupled to the second gear.

Example 22: The counterbalance system of example 21, wherein the gear hinge assembly further comprises: a first friction member configured to contact the housing; a second friction member coupled to the first friction member; and a plurality of biasing members, wherein the plurality of biasing members biases the second friction member toward the first friction member to impart a friction force between the first friction member and the housing.

Example 23: The counterbalance system of example 22, wherein the friction force is configured to facilitate manipulation of the first member and the second member.

Example 24: A medical system comprises an instrument manipulator configured to control a pose of a medical instrument with respect to patient anatomy; a support structure configured to control a pose of the instrument manipulator; a hinged assembly including a first member coupled by a hinge to a second member; and a counterbalance assembly to counterbalance a weight of the first member as the first member rotates relative to the second member about the hinge, the counterbalance assembly comprising: a spring; a termination member coupled to the spring and configured to control a rate of the spring; a cable coupled to the termination member; and a preload adjustment assembly coupled to the cable and configured to control a preload of the spring.

Example 25: The system of example 24, wherein: the spring extends within the second member; and the cable is coupled to the hinge.

Example 26: The system of example 24, wherein the termination member includes a helical groove, and wherein a configuration of the spring within the helical groove determines the rate of the spring.

Example 27: The system of example 24, wherein the preload adjustment assembly comprises: an elongate member extending through the termination member; and a coupling member configured to receive a rotational input relative to the elongate member to control the preload of the spring.

Example 28: The system of example 27, wherein the counterbalance assembly further comprises a cable mount, wherein the cable is coupled to the termination member via the cable mount.

Example 29: The system of example 28, wherein the elongate member is coupled to the cable mount.

Example 30: The system of example 24, wherein the counterbalance assembly further comprises a cable mount positioned between the cable and the termination member, the cable mount including a proximal portion and a distal portion.

Example 31: The system of example 30, wherein the cable is coupled to the proximal portion of the cable mount, and the preload adjustment assembly is coupled to the distal portion of the cable mount.

Example 32: The system of example 24, wherein the hinge comprises a gear hinge assembly.

Example 33: The system of example 32, wherein the gear hinge assembly comprises: a housing; a first gear mounted in the first member; and a second gear mounted in the second member, wherein the first gear is coupled to the second gear.

Example 34: The system of example 33, wherein the gear hinge assembly further comprises: a first friction member configured to contact the housing; a second friction member coupled to the first friction member; and a plurality of biasing members, wherein the plurality of biasing members biases the second friction member toward the first friction member to impart a friction force between the first friction member and the housing.

Example 35: The system of example 34, wherein the friction force is configured to facilitate manipulation of the first member and the second member.

Example 36: A method for controlling a position of a medical instrument coupled to a carriage, the method comprising: translating an insertion stage along a linear axis along a base; and simultaneously translating the carriage along the linear axis to provide telescoping of the carriage and insertion stage using a drive belt, the drive belt being fixed to the base and engaged with a pulley, the pulley being coupled to the insertion stage, and the carriage being fixed to the drive belt using a connecting element, wherein driving the drive belt moves the carriage along the linear axis to advance or retract the medical instrument.

Example 37: The method of example 36, further comprising receiving an input from an input device, wherein the input device is located on at least one of the carriage, the insertion stage, or the base.

Example 38: The method of example 37, wherein the drive belt is driven by a drive motor and the drive motor is actuated based on the input.

Example 39: The method of example 37, wherein the input provides for manual translation of the carriage, wherein the manual translation drives the drive belt.

Example 40: The method of any of examples 36-38, wherein the medical instrument comprises a flexible elongate device and the method further comprises driving, by a plurality of actuators, a plurality of pull wires to steer the flexible elongate device.

Example 41: The method of example 40, comprising manipulating, by at least some of the pull wires, a position of a distal end portion of the flexible elongate device.

Example 42: The method of any of examples 36-38, wherein the method further comprises rotating an instrument manipulator about a rotation axis defined along a length of an arm portion of a support structure, wherein the instrument manipulator comprises the carriage, the insertion stage, and the base.

Example 43: The method of example 42, further comprising: receiving data for determining a shape of a distal end portion of the medical instrument when the distal end portion of the medical instrument is positioned adjacent an anatomical opening of a patient; comparing the determined shape of the distal end portion of the medical instrument with a threshold shape value; and rotating the instrument manipulator based on the comparison.

Example 44: The method of example 43, wherein the distal end portion of the medical instrument is positioned within a medical insertion device, wherein the insertion device is configured to aid insertion of the medical instrument into the anatomical opening of the patient.

Example 45: The method of example 43, further comprising, displaying a visual indicator providing guidance for rotating the instrument manipulator based on the comparison.

Example 46: The method of example 43, further comprising automatically rotating the instrument manipulator based on the comparison.

Example 47: A method for controlling a pose of an instrument manipulator supporting a medical instrument, the method comprising: receiving data for determining a shape of a length of the medical instrument; comparing the shape of the length of the medical instrument with a threshold value; determining if the shape of the length of the medical instrument is beyond the threshold value; and adjusting a position of the instrument manipulator based on the determination.

Example 48: The method of example 47, further comprising providing an indicator to guide a user during the adjusting of the position of the instrument manipulator, to alter the shape of the length of the medical instrument within the threshold value.

Example 49: The method of example 48, wherein adjusting the position of the instrument manipulator includes adjusting an orientation of the instrument manipulator.

Example 50: The method of example 48, wherein the indicator is at least one of a visual indicator or an audible indicator.

Example 51: The method of example 47, wherein the threshold value is a maximum bend value.

Example 52: The method of example 47, wherein the adjusting of the pose of the instrument manipulator comprises altering a configuration of a support structure carrying the instrument manipulator, wherein the support structure includes a plurality of links and at least one joint.

Example 53: The method of example 52, further comprising receiving an input from an input device to provide rotation of the at least one joint for altering the configuration of the support structure.

Example 54: The method of example 53, further comprising unlocking the at least one joint based on the input to allow the support structure to be manually positioned.

Example 55: The method of example 53, further comprising driving the at least one joint using a motor, based on the input to allow the support structure to be positioned.

Example 56: The method of example 47, wherein the data for determining the shape of the length of the medical instrument is received when the length of the medical instrument is positioned within a medical device coupled to an anatomical opening of a patient.

What is claimed is:

1. A medical instrument system comprising:
an instrument manipulator configured to control a pose of a medical instrument with respect to a patient anatomy, the medical instrument including a sensor;

a support structure configured to control a pose of the instrument manipulator; and a control system including a processor, the control system configured to:

receive, from the sensor of the medical instrument, data for determining a shape of a length of the medical instrument;

compare the shape of the length of the medical instrument with a threshold value;

determine if the shape of the length of the medical instrument is beyond the threshold value; and provide instructions for adjusting a position of the instrument manipulator based on the determination.

2. The system of claim 1, wherein the sensor is configured to sense the shape of the length of the medical instrument.

3. The system of claim 2, wherein the sensor includes at least one of a fiber shape sensor or a plurality of electromagnetic (EM) sensors.

4. The system of claim 1, wherein the support structure comprises a plurality of sensors to determine the pose of the instrument manipulator.

5. The system of claim 1, further comprising a display for providing the instructions to a user, wherein the instructions include an indicator providing guidance for adjusting the pose of the instrument manipulator relative to the patient anatomy, and wherein adjusting the pose of the instrument manipulator includes adjusting the position of the instrument manipulator or adjusting an orientation of the instrument manipulator.

6. The system of claim 1, wherein the instructions for adjusting the position of the instrument manipulator include instructions for automatically adjusting the support structure.

7. The system of claim 6, wherein the instructions for automatically adjusting the support structure include instructions for automatically adjusting a position of the support structure or automatically adjusting an orientation of the support structure.

8. The system of claim 1, wherein the support structure comprises a set of links and joints, wherein the set includes at least one link and at least one joint.

9. The system of claim 8, further comprising an input device, wherein a configuration of the set of links and joints is adjusted based on input from the input device.

10. The system of claim 9, wherein the input device is positioned on the instrument manipulator.

11. The system of claim 10, wherein the input device includes at least one of a button or a switch.

12. The system of claim 8, wherein the support structure includes at least one motor for control of the at least one joint.

13. The system of claim 8, wherein the set of links and joints includes at least one brake for control of the at least one joint.

14. The system of claim 1, wherein the instrument manipulator comprises:

an instrument carriage comprising a medical instrument connector configured to engage the medical instrument, the instrument carriage configured to move linearly along a linear axis to advance or retract the medical instrument with respect to the patient anatomy; and an insertion stage engaged with the instrument carriage and aligned with the instrument carriage along the linear axis, wherein the insertion stage and the instrument carriage are configured to move in a telescoping motion.

15. The system of claim 14, wherein the insertion stage and the instrument carriage are configured to telescope along the linear axis.

16. The system of claim 14, wherein the insertion stage includes a drive assembly comprising a drive belt and a drive motor configured to drive the drive belt.

17. The system of claim 16, wherein the instrument manipulator further comprises:

a connecting element having a distal end fixedly coupled to the drive belt and a proximal end fixed to the instrument carriage.

18. The system of claim 16, wherein the medical instrument comprises a flexible elongate device.

19. The system of claim 1, wherein the instructions for adjusting the position of the instrument manipulator include instructions for rotating the instrument manipulator.

20. The system of claim 19, wherein the instrument manipulator is configured to rotate about a rotation axis defined along a length of an arm portion of the support structure.

* * * * *